United States Patent
Liu

(10) Patent No.: US 9,989,533 B2
(45) Date of Patent: Jun. 5, 2018

(54) ANTI-TNF INDUCED APOPTOSIS (ATIA) DIAGNOSTIC MARKERS AND THERAPIES

(75) Inventor: Zhenggang Liu, Germantown, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days. days.

(21) Appl. No.: 13/322,863

(22) PCT Filed: May 27, 2010

(86) PCT No.: PCT/US2010/036394
§ 371 (c)(1),
(2), (4) Date: Nov. 28, 2011

(87) PCT Pub. No.: WO2010/138709
PCT Pub. Date: Dec. 2, 2010

(65) Prior Publication Data
US 2012/0082660 A1    Apr. 5, 2012

Related U.S. Application Data

(60) Provisional application No. 61/182,072, filed on May 28, 2009.

(51) Int. Cl.
*G01N 33/53* (2006.01)
*G01N 33/574* (2006.01)
(Continued)

(52) U.S. Cl.
CPC ... *G01N 33/57407* (2013.01); *C07K 14/4747* (2013.01); *C07K 14/82* (2013.01); *G01N 2800/52* (2013.01); *G01N 2800/56* (2013.01)

(58) Field of Classification Search
None
See application file for complete search history.

(56) References Cited

U.S. PATENT DOCUMENTS 4,816,567 A    3/1989  Cabilly et al.
4,939,239 A    7/1990  Matsuhashi et al.
(Continued)

FOREIGN PATENT DOCUMENTS

WO    WO 1995/0251116    9/1995
WO    01/46418 A1        6/2001
(Continued)

OTHER PUBLICATIONS

J. Massague, TGF-Beta signal transduction, Annu. Rev. Biochem. 67:753,91, 1998.*
(Continued)

*Primary Examiner* — Claire Kaufman
(74) *Attorney, Agent, or Firm* — Bryan D. Zerhusen; Locke Lord LLP

(57) ABSTRACT

The invention features diagnostic and therapeutic methods and compositions featuring Anti-TNF Induced Apoptosis (ATIA). ATIA is useful as a diagnostic marker for cancer, in particular for glioblastoma. ATIA is also a therapeutic target in diseases such as cancer. The invention encompasses combination therapies where knockdown of ATIA is used in combination with other treatment. The invention also features kits for use in the diagnostic and therapeutic methods.

12 Claims, 19 Drawing Sheets

(51) Int. Cl.
    C07K 14/47    (2006.01)
    C07K 14/82    (2006.01)

(56) References Cited

U.S. PATENT DOCUMENTS

| | | | |
|---|---|---|---|
| 5,223,409 A | 6/1993 | Ladner et al. |
| 5,225,539 A | 7/1993 | Winter |
| 5,530,101 A | 6/1996 | Queen et al. |
| 5,585,089 A | 12/1996 | Queen et al. |
| 5,605,793 A | 2/1997 | Stemmer et al. |
| 5,693,762 A | 12/1997 | Torri et al. |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,837,832 A | 11/1998 | Chee et al. |
| 5,859,205 A | 1/1999 | Adair et al. |
| 6,436,665 B1 | 8/2002 | Kuimelis et al. |

FOREIGN PATENT DOCUMENTS

| | | |
|---|---|---|
| WO | 2009/014565 A2 | 1/2009 |
| WO | 2010/045714 A1 | 4/2010 |

OTHER PUBLICATIONS

Griffith et al., TRAIL gene therapy: From preclinical development to clinical application, Curr. Gene Ther. 9(10):9-19, Feb. 2009, [retrieved as Author manuscript available in PMC Aug. 17, 2009].*
Mason et al., Canadian recommentations for the treatment of glioblastoma multiforme, Curr. Oncol. 14(3):110-117, Jun. 2007.*
Yuichi Ikeda, et al. "Vasorin, a transforming growth factor beta-binding protein expressed in vascular smooth muscle cells, modulates the aterial response to injury in vivo", Proceedings of the National Academy of Sciences of the United States of America, vol. 101, No. 29, Jul. 20, 2004.
Adilia Hormigo et a., "YKL-40 and matrix metalloproteinase-9 as potential serum biomarkers for patients with high-grade gliomas", Clinical Cancer Research: An Official Journal of the American Association for Cancer Research Oct. 1, 2006 LNKD-PUBMED: 17029073, vol. 12, No. 9, Oct. 1, 2006.
John F. Reavey-Cantwell, et al. "The prognostic value of tumor markers in patients with gliblastoma multiforme: analysis of 32 patients and review of the literature" Journal of Neuro-Oncology Dec. 2001 LMKD-PUBMED:11859975, vol. 55, No. 3, Dec. 2001.
Akira S. & Takeda K. (2004) "Toll-like receptor signaling", Nat. Rev. Immunol. 4, 499-511.
Ashkenazi, A., (1998) "Death receptors: signaling and modulation", Science 281, 1305-1308.
Baeuerle, P.A. and Baltimore, D. (1996). "NF-KB: ten years after", Cell 87, 13-20.
Baldwin A.S., "Control of oncogenesis and cancer therapy resistance by the transcription factor NFKB", (2001). J. Clin. Invest. 107, 241-246.
Baud, V., "Signal transduction by tumor necrosis factor and its relatives", Trends Cell Biol. 11, 372-7 (2001).
Beutler, B. (1988), "Tumor necrosis, cachexia, shock, and inflammation: A common mediator", Ann. Rev. Biochem. 57, 505-518.
Bodmer, J.L., (1997) "TRAMP, a novel apoptosis-mediating receptor with sequence homology to tumor necrosis factor receptor 1 and Fas(Apo-1/CD95)", Immunity 6, 79-88.
Boldin, M.P.,(1995). "A novel protein that interacts with the death domain of Ras/APO1 contains a sequence motif related to the death domain", J. Biol. Chem. 270, 7795-7798.
Carlo-Stella et al. "Targeting TRAIL agonistic receptors for cancer therapy", Clin Cancer Res. Apr. 15, 2007;13(8):2313-7.
Carell et al., "A Novel Procedure for the Synthesis of Libraries Containing Small Organic Molecules", Angew. Chem. Int. Ed. Engl. 33:2059-2061, (1994).
Carswell, E.A., (1975) "An endotoxin-induced serum factor that causes necrosis of tumors", Proc Natl Acad Sci USA 72, 3666-3670.
Chaudhary, P.M., (1997) "Death receptor 5, a new member of the TNFR family, and DR4 induce FADD-dependent apoptosis and activate the NF-kappaB pathway", Immunity 7, 821-830.
Chen, G.. "TNF-R1 signaling: a beautiful pathway", Science 296, 1634-1635 (2002).
Chinnaiyan, A.M., (1995) "FADD, a novel death domain-containing protein, interacts with the death domain of Fas and initiates apoptosis", Cell 81, 505-512.
Chinnaiyan, A.M., (1996), "Signal transduction by DR3, a death domain-containing receptor related to TNFR-1 and CD95", Science 274, 990-992.
Cho et al., "An unnatural biopolymer", Science 261:1303-1305, (1993).
Cichowski K, (2001) "NH tumor suppressor gene function: narrowing the GAP", Cell 104, 593-604.
Coulson, E.J., (1999) "p75 neurotrophin receptor-mediated neuronal death is promoted by Bcl-2 and prevented by Bcl-xL", J Biol Chem 274, 16387-16391.
Coussens, L.M. & Werb Z. (2002) Inflammation and cancer. Nature 420, 860-867.
Cull, et al.,Screening for Receptor Ligands Using Large Libraries of Peptides Linked to the C Terminus of the *lac* Repressor, Proc. Natl. Acad. Sci. USA vol. 89, pp. 1865-1869, Mar. 1992.
Cwirla, et al. Peptides on Phage: A Vast Library of Peptides for Identifying Ligands, Proc. Natl. Acad. Sci. vol. 87, pp. 6378-6382, Aug. 1990.
Decker, K. (1974) "Galactosamine hepatitis: key role of the nucleotide deficiency period in the pathogenesis of cell injury and cell death", Rev. Physiol. Biochem. Pharmaco. 71: 77-106.
Derosa, D.C., (2008) "Tumor-derived death receptor 6 modulates dendritic cell development", Cancer Immunol Immunother 57,777-787.
Devin, A. (2003) "The role of the death domain kinase RIP in tumor-nerosis-factor-induced activation of mitogen-activated protein kinases", EMBO reports, 4, 623-627.
Devin, A., (2000) "The distinct roles of TRAF2 and RIP in IKK activation by TNF-R1: TRAF2 recruits IKK to TNF-R1 while RIP mediates IKK activation", Immunity 12, 419-429.
Devlin, et al., Random Peptide Libraries: A Source of Specific Protein Binding Molecules, Science vol. 249, pp. 404-406, (1990).
DeWitt et al., "Diversions": An Approach to Nonpeptide, nonoligomeric Chemical Diversity, Proc. Natl. Acad. Sci. USA. vol. 90, pp. 6909-6913, (1993).
Ding It, (2001) "Astrocyte-specific expression of activated p21-ras results in malignant astrocytoma formation in a transgenic mouse model of human gliomas", Cancer Res. 61, 3826-36.
El Yazidi-Belkoura, I., (2003) "Tumor necrosis factor receptor-associated death domain protein is involved in the neurotrophin receptor-mediated antiapoptotic activity of nerve growth factor in breast cancer cells", J Biol Chem 278, 16952-16956.
Erb et al., Recursive Deconvolution of Combinatorial Chemical Libraries, Proc. Natl. Acad. Sci. USA vol. 91, pp. 11422-11426, Nov. 1994.
Felici, et al., Selection of Antibody Ligands from a Large Library of Oligopeptides Expressed on a Multivalent Exposition Vector, J. Mol. Biol. vol. 222, pp. 301-310, (1991).
Fodor et al., Multiplexed Biochemical Assays with Biological Chips, Nature vol. 364, pp. 555-556, Aug. 1993.
Gallop et al., Applications of Combinatorial Technologies to Drug Discovery. 1. Background and Peptide Combinatorial Libraries, J. Med. Chem. vol. 37, No. 9, pp. 1233-1251, (1994).
Ge, et al., "UPA, a universal protein array system for quantitative detection of protein-protein, protein-DNA, protein-RNA and protein-ligand interactions", Nucleic Acids Res. 28:e3.i-e3.vii, 2000.
Hansen JM, (2006) "Mitochondrial thioredoxin-2 has a key role in determining tumor necrosis factor-alpha-induced reactive oxygen species generation, Nf-kappaB activation, and apoptosis", Toxicol Sci. 91, 643-50.
Hansson, et al., Evolution of Differential Substrates Specificities in Mu Class Glutathione Transferases Probed by DNA Shuffling, J. Mol. Biol. vol. 287, pp. 265-276 (1999).

(56) References Cited

OTHER PUBLICATIONS

Harayama, S., Artificial Evolution by DNA Shuffling, Trends Biotechnol., vol. 16(2), pp. 76-82, (1998).
Heller et al., Discovery and Analysis of Inflammatory Disease-Related Genes Using cDNA Microarrays, Proc. Natl. Acad. Sci. vol. 94, pp. 2150-2155, Mar. 1997.
Holler, N, (2000) "Fas triggers an alternative, caspase-8-independent cell death pathway using the kinase RIP as effector molecule", Nat. Immunol. 1, 489-95.
Houghten, et al., The Use of Synthetic Peptide Combinatorial Libraries for the Identification of Bioactive Peptides, Biotechniques vol. 13, No. 3, pp. 412-421, (1992).
Hsu, H., (1995) "The TNF receptor 1-associated protein TRADD signals cell death and NF-B activation", Cell 81, 495-504.
Hsu, H., (1996a) "TRADD-TRAF2 and TRADD-FADD interactions define two distinct TNF receptor-1 signal transduction pathways", Cell 84, 299-308.
Hsu, H., (1996b) "TNF-dependent recruitment of the protein kinase RIP to the TNF receptor-1 signaling complex", Immunity 4, 387-396.
Huang B., (2008) "TLR signaling by tumor and immune cells: a double-edged sword", Oncogene 27, 218-224.
Iwasaki A. & Medzhitov R. (2004) Toll-like receptor control of the adaptive immune responses. Nat Immunol. 5, 987-995.
Janknecht et al., Rapid and Efficient Purification of Native Histidine-Tagged Protein Expressed by Recombinant Vaccinia Virus, Proc. Natl. Acad. Sci. USA, vol. 88, pp. 8972-8976, Oct. 1991.
Jin, Z. (2006) "Distinct signaling pathways in TRAIL—versus tumor necrosis factor-induced apoptosis", Mol Cell Biol. 26, 8136-48.
Karin M., "NFKB in cancer: from innocent bystander to major culprit", (2002). Nat. Rev. Cancer 2, 301-310.
Karin, M., (1997) "AP-1 function and regulation", Curr. Opin. Cell Biol. 9, 240-246.
Kasof, G.M., (2001) Tumor necrosis factor-alpha induces the expression of DR6, a member of the TNF receptor family, through activation of NF-kappaB. Oncogene 20, 7965-7975.
Kelliher, M.A., (1998) the death domain kinase RIP mediates the TNF-induced NF-kappaB signal. Immunity 8, 297-303.
Kim, Y., (2007) TNF-Induced Activation of the Nox1 NADPH Oxidase and Its Role in the Induction of Necrotic Cell Death. Mol. Cell. 26, 675-687.
Kischkel, F.C., (2000) Apo2L/TRAIL—dependent recruitment of endogenous FADD and caspase-8 to death receptors 4 and 5. Immunity 12, 611-620.
Kitson, J., (1996) A death-domain-containing receptor that mediates apoptosis. Nature 384, 372-375.
Kreuz S, (2001) NF-kappaB inducers upregulate cFLIP, a cycloheximide-sensitive inhibitor of death receptor signaling. Mol Cell Biol. 21, 3964-73.
Lam, K., Application of Combination Library Methods in Cancer Research and Drug Discovery, Anticancer Drug Design, 2, pp. 145-167, Apr. 1997.
Lam, et al., A New Type of Synthetic Peptide Library for Identifying Ligand-Binding Activity, Nature vol. 354, pp. 82-84, Nov. 1991.
Lavrik, I., (2005) Death receptor signaling. J Cell Sci 118, 265-267.
Lewis, M., Tartaglia, (1991) Cloning and expression of cDNAs for two distinct murine tumor necrosis factor receptors demonstrate one receptor is species specific. Proc. Natl. Acad. Sci. USA 88, 2830-2834.
Li Q. NFKB regulation in the immune system. (2002). Nat. Rev. Immunol. 2, 725-734.
Liepinsh, E., (1997) NMR structure of the death domain of the p75 neurotrophin receptor. EMBO J 16, 4999-5005.
Lin A. & Karin M. NFKB in cancer: a marked target. (2003). Semin. Can. Biol. 13, 107-114.
Lin Y, (2003) TRAF2 exerts its antiapoptotic effect by regulating the expression of Kruppel-like factor LKLF. Mol Cell Biol. 23, 5849-56.
Lin Y., (2004) Tumor necrosis factor-induced nonapoptotic cell death requires receptor-interacting protein-mediated cellular reactive oxygen species accumulation. J. Biol. Chem. 279, 10822-10828.
Lin, Y., (2000) The death domain kinase RIP is essential for TRAIL (Apo2L)-induced activation of IkappaB kinase and c-Jun N-terminal kinase. Mol Cell Biol 20, 6638-6645.
Liu, H.T., (1999) In vivo interaction of nucleophosmin/B23 and protein C23 during cell cycle progression in HeLa cells. Cancer Letters, 144, 45-54.
Liu, J., (2001) Enhanced CD4+ T cell proliferation and Th2 cytokine production in DR6-deficient mice. Immunity 15, 23-34.
Liu, Z.G, (1996) Dissection of TNF receptor 1 effector functions: JNK activation is not linked to apoptosis while NF-KB activation prevents cell death. Cell 87, 565-576.
Liu, ZG. (2001) Cellular responses to Tumor Necrosis Factor (TNF). Current Issues in Molecular Biology 3, 79-90.
Llovet J.M., (2003) Hepatocellular carcinoma. Lancet 362, 1907-1917.
Lockhart, et al., Expression Monitoring by Hybridization to High-Density Oligonucleotide Arrays, Nature Biotech. vol. 14, pp. 1675-1680, Dec. 1996.
Locksley, R. M., The TNF and TNF receptor superfamilies: integrating mammalian biology. Cell 104, 487-501 (2001).
Lorenzo et al., PCR Methods for the Introduction of Mutations in Genes Cloned and Expressed in Vaccinia Virus, BioTechniques vol. 24, No. 2 pp. 308-313, (1998).
MacBeath et al., Printing Proteins as Microarrays for High-Throughput Function Determination, Science vol. 289, pp. 1760-1763, Sep. 2000.
Maeda S., (2005) IKKI3 couples hepatocyte death to cytokine-driven compensatory proliferation that promotes chemical hepatocarcinogenesis. Cell 121, 977-990.
Marsh, D.G., Preparation and Properties of 'Allergoids' Derived from Native Pollen Allergens by Mild Formalin Treatment, 1971, Int. Arch. Of Allergy and Appl. Immunol. vol. 41, pp. 199-215 (1971).
Marsters, S.A., (1996) Apo-3, a new member of the tumor necrosis factor receptor family, contains a death domain and activates apoptosis and NF-kappa B. Curr Biol 6, 1669-1676.
Masutani H, (2005) The thioredoxin system in retroviral infection and apoptosis. Cell Death Differ. 12 Suppl 1, 991-998.
Mauad TH, (1994) Mice with homozygous disruption of the mdr2 P-glycoprotein gene. A novel animal model for studies of nonsuppurative inflammatory cholangitis and hepatocarcinogenesis. Am. J. Pathol. 145, 1237-1245.
Merrifield, R.B., Solid Phase Peptide Synthesis. I. The Synthesis of a Tetrapeptide, J. Am. Chem. Soc., 85: pp. 2149-2154, Jul. 1963.
Meurette, 0., (2007) TRAIL induces receptor-interacting protein 1-dependent and caspase-dependent necrosis-like cell death under acidic extracellular conditions. Cancer Res 67, 218-226.
Micheau, 0. & Tschopp, J. Induction of TNF receptor I-mediated apoptosis via two sequential signaling complexes. Cell 114, 181-190 (2003).
Migone, T.S., (2002) TL1A is a TNF-like ligand for DR3 and TR6/DcR3 and functions as a T cell costimulator. Immunity 16, 479-492.
Moore R.J., (1999) Mice deficient in tumor necrosis factor-a are resistant to skin carcinogenesis. Nat. Med. 5, 828-831.
Mueller M.M. (2006) Inflammation in epithelial skin tumors: old stories and new ideas. Eur. J. Can. 42,735-744.
Nagata, S. (1995) THE Fas death factor. Science 267, 1449-1456.
Nagata, S. (1997) Apoptosis by death factor. Cell 88, 355-365.
Nonn L, (2003) The absence of mitochondrial thioredoxin 2 causes massive apoptosis, exencephaly, and early embryonic lethality in homozygous mice. Mol Cell Biol. 23, 916-922.
Nykjaer, A., (2005) p75NTR—live or let die. Curr Opin Neurobiol 15, 49-57.
Otto, D. and Unsicker, K., "Basic FGF Reverses Chemical and Morphological Deficits in the Nigrostriatal System of MPTP-Treated Mice, " J. Neurosci. 10: 1912-1921 (1990).

(56) References Cited

OTHER PUBLICATIONS

Otto, D. et al., "Basic Fibroblast Growth Factor and Nerve Growth Factor Administered in Gel Foam Rescue Medial Septal Neurons after Fimbria Fornix Transection", J. Neurosci. Res. 22: 83-91 (1989).
Pan, G., (1998) Identification and functional characterization of DR6, a novel death domain-containing TNF receptor. FEBS Lett 431, 351-356.
Papadakis, K.A., (2005) Dominant role for TL1A/DR3 pathway in IL-12 plus IL-18—induced IFN-gamma production by peripheral blood and mucosal CCR9+ T lymphocytes. J Immunol 174, 4985-4990.
Park, S.M., (2005) Nonapoptotic functions of Fadd—binding death receptors and their signaling molecules. Curr Opin Cell Biol 17, 610-616.
Patten et al., Applications of DNA Shuffling to Pharmaceuticals and Vaccines, Curr. Opinion Biotechnol, 8:724-733 (1997).
Peter, M.E. (2000) The TRAIL DISCussion: It is FADD and caspase-8! Cell Death Differ 7, 759-760.
Peter, M.E., (2003) The CD95(APO-1/Fas) DISC and beyond. Cell Death Differ 10, 26-35.
Pikarsky E, (2004) NF-KB functions as a tumor promoter in inflammation-associated cancer. Nature 431, 461-466.
Reilly KM, (2000) NFL;Trp53 mutant mice develop glioblastoma with evidence of strain-specific effects. Nat Genet. 26, 109-13.
Roberge, et al., A Strategy for a Convergent Synthesis of N-Linked Glycopeptides on a Solid Support, Science, vol. 269, pp. 202-204, Jul. 1995.
Rothe, M., (1994) A novel family of putative signal transducers associated with the cytoplasmic domain of the 75 kDa tumor necrosis factor receptor. Cell 78, 681-692.
Rothe, M., (1995) TRAF2-mediated activation of NF-KB by TNF receptor 2 and CD40. Science 269, 1424-1427.
Schena, et al. Parallel Human Genome Analysis: Microarray-based Expression Monitoring of 1000 Genes, Proc. Natl. Acad. Sci. USA, vol. 93, pp. 10614-10619, Oct. 1996.
Schmidt, C.S., (2003) Enhanced B cell expansion, survival, and humoral responses by targeting death receptor 6. J Exp Med 197, 51-62.
Schneider, P., (1997) TRAIL receptors 1 (DR4) and 2 (DR5) signal FADD-dependent apoptosis and activate NF-kappaB. Immunity 7, 831-836.
Scott, et al., Searching for Peptide Ligands with an Epitope Library, Science vol. 249, pp. 386-390, Jul. 1990.
Screaton, G.R., (1997) LARD: a new lymphoid-specific death domain containing receptor regulated by alternative pre-mRNA splicing. Proc Natl Acad Sci USA 94, 4615-4619.
Siebenlist, U., Franzoso, G., and Brown, K. (1994) Structure, regulation and function of NF-KB. Annu Rev Cell Biol 10, 405-455.
Smith, C. A., (1994) The TNF Receptor superfamily of cellular and viral proteins : activation, costimulation and death. Cell 76, 959-962.
Spyrou G, (1997) Cloning and expression of a novel mammalian thioredoxin. J Biol Chem. 272, 2936-41.
Stanger, B.Z., Leder, P., Lee, T.H., Kim, E., and Seed, B. (1995) RIP: a novel protein containing a death domain that interacts with Fas/APO-1 (CD95) in yeast and causes cell death. Cell 81, 513-523.
Su, W.B., (2006) Differential regulation of interleukin-8 gene transcription by death receptor 3 (DR3) and type I TNF receptor (TNFRI). Exp Cell Res 312, 266-277.
Sugarman, B.J., (1985) Recombinant human tumor necrosis factor-alpha: effects on proliferation of normal and transformed cells in vitro. Science 230, 943-5.
Swann J.B., (2008) Demonstration of inflammation-induced cancer and cancer immunoediting during primary tumorigenesis. PNAS 105, 652-656.

Szlosarek P, Charles KA, Balkwill FR. (2006) Tumor necrosis factor-a as a tumor promoter. Eur. J. Cancer 42, 745-750.
Tanaka T., Thioredoxin-2 (TRX-2) is an essential gene regulating mitochondria-dependent apoptosis. EMBO J. 21, pp. 1695-1703, (2002).
Tarr, Methods of Protein Microcharacterization, J. E. Silver, Ed., Humana Press, Clifton, N.J., pp. 155-194, (1986).
Tartaglia, et al., Two TNF receptors. Immunol. Today vol. 13, No. 5, pp. 151-153, (1992).
Tiegs, G., A. Tumor necrosis factor is a terminal mediator in galactosamine/endotoxin-induced hepatitis in mice. Biochem. Pharmacol. 38, 627-31 (1989).
Ting, et al., RIP mediates tumor necrosis factor receptor 1 activation of NF-KB but not FAS/APO-1-initiated apoptosis. EMBO J. vol. 15, No. 22, pp. 6189-6196, (1996).
Tracey, et al., Tumor necrosis factor, other cytokines and disease. Annu. Rev. Cell Biol. vol. 9, pp. 317-343 (1993).
Tyagi et al., Nature Biotechnology 14(3):303-8, (1996).
Van Antwerp, et al., Inhibition of TNF-induced apoptosis by NF-KB. Trends Cell Biol vol. 8, pp. 107-111, Mar. 1998.
Vandenabeele, et al., Two tumor necrosis factor receptors: structure and function. Trends Cell Biol. vol. 5, pp. 392-399, Oct. 1995.
Verna et al., N-nitrosodiethylamine mechanistic data and risk assessment: bioactivation, DNA-adduct formation, mutagenicity, and tumor initiation. Pharmacol. Ther. vol. 71, pp. 57-81, (1996).
Voortman et al., TRAIL therapy in non-small cell lung cancer cells: sensitization to death receptor—mediated apoptosis by proteasome inhibitor bortezomib Mol Cancer Ther 6, pp. 2103-2112, Jul. 2007.
Wahl, et al., Improved Radioimaging and Tumor localization with Monoclonal F(ab')$_2$, J. Nucl. Med. 24, pp. 316 325 (1983).
Wajant, H., Death receptors. Essays Biochem vol. 39, pp. 53-71, (2003).
Wajant, et al., Tumor necrosis factor signaling. Cell Death Differ. 10, 45-65 (2003).
Wang, et al., NF-xB antiapoptosis: induction of TRAF1 and TRAF2 and c-IAP1 and c-IAP2 to suppress caspase-8 activation. Science vol. 281, pp. 1680-1683, Sep. 1998.
Wang, et al., DR3 regulates negative selection during thymocyte development. Mol. Cell. Biol. vol. 21, No. 10, pp. 3451-3461, (2001).
Wen, et al., TL1A-induced NF-kappaB activation and c-IAP2 production prevent DR3-mediated apoptosis in TF-1 cells. J Biol Chem. vol. 278, No. 40, pp. 39251-39258, 2003.
Wie et al., Supression of Reaginic Antibodies with Modified Allergens, Int. Arch. Allergy Appl. Immunol. 64(1), pp. 84-99, (1981).
Wu, et al., IEX-1L, an apoptosis inhibitor involved in NF-KB-mediated cell survival. Science vol. 281, pp. 998-1001, Aug. 1998.
Yeh, et al., Early lethality, functional NF-kappaB activation, and increased sensitivity to TNF-induced cell death in TRAF2-deficient mice. Immunity vol. 7, pp. 715-725, Nov. 1997.
Zhang, et al., Fas-mediated apoptosis and activation-induced T-cell proliferation are defective in mice lacking FADD/Mortl. Nature vol. 392, pp. 296-300, Mar. 1998.
Zhao, et al., Impaired c-Jun amino terminal kinase activity and T cell differentiation in death receptor 6-deficient mice. J. Exp. Med. vol. 194, No. 10, pp. 1441-1448, Nov. 2001.
Zheng, et al., Competetive Control of independent programs of tumor necrosis factor receptor-induced cell death by TRADD and RIP1. Mol. Cell. Biol. 26, pp. 3505-3513, May 2006.
Zhu, et al., Analysis of Yeast Protein Kinases Using Protein Chips, Nature Genet., vol. 26, pp. 283-289, Nov. 2000.
Zuckermann, et al., Discovery of Nanomolar Ligands for 7-Transmembrane G-Protein-Coupled Receptors from a Diverse N-(Substituted)glycine Peptoid Library, J. Med. Chem. vol. 37, No. 17, pp. 2678-2685, May 1994.

* cited by examiner

PCR:p1/p2

PCR:p3/p2, p4

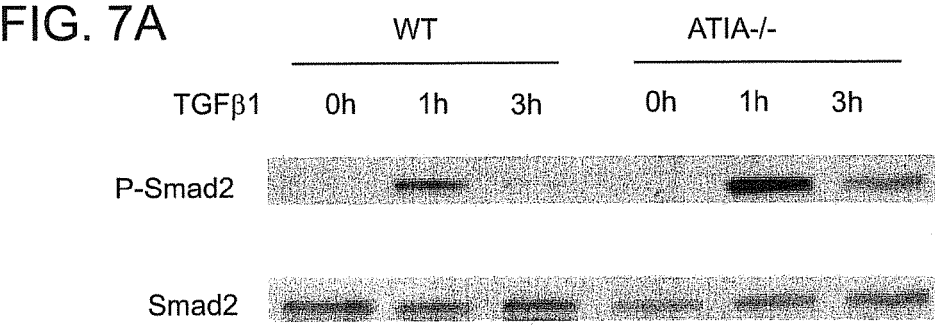
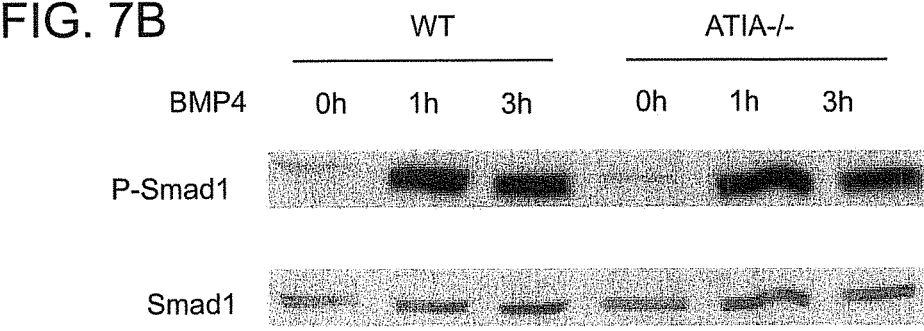
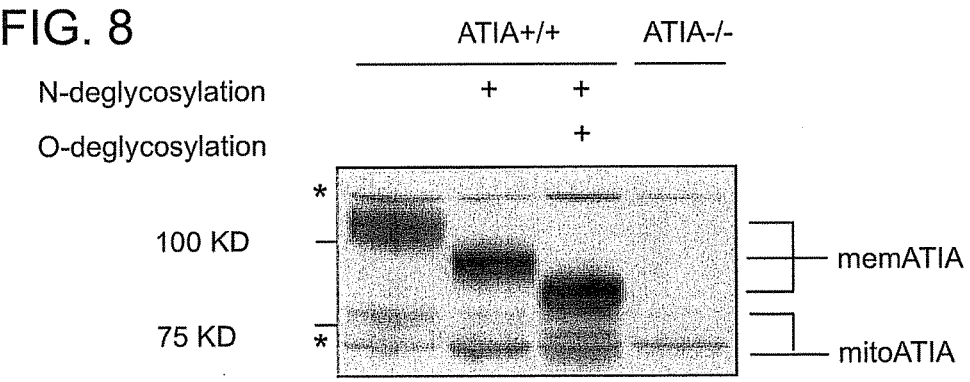

FIG. 15
| | stain | positive | negative |
|---|---|---|---|
| Age | <10 y<br>2 cases | 2 / 2 | |
| | 30-40 y<br>4 cases | 2 / 4 | 2 / 4 |
| | 40-50 y<br>8 cases | 7 / 8 | 1 / 8 |
| | 50-60 y<br>9 cases | 7 / 9 | 2 / 9 |
| | > 60 y<br>7 cases | 5 / 7 | 2 / 7 |
FIG. 16
Examples from the glioblastoma tissue arrays
Adjacent normal brain tissue          Glioblastoma IV
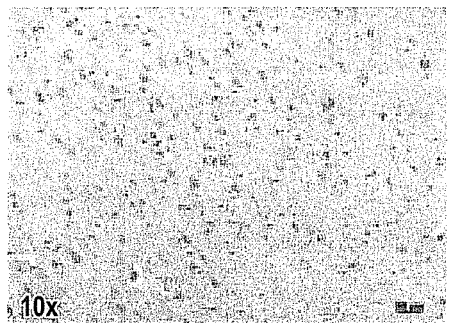
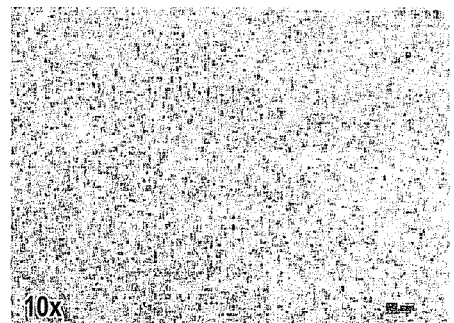
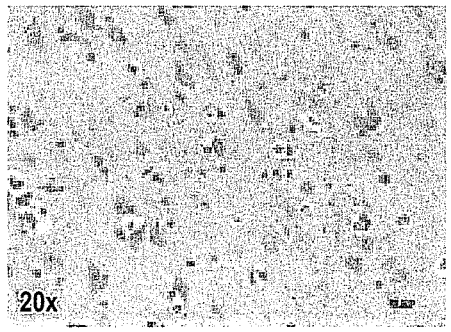
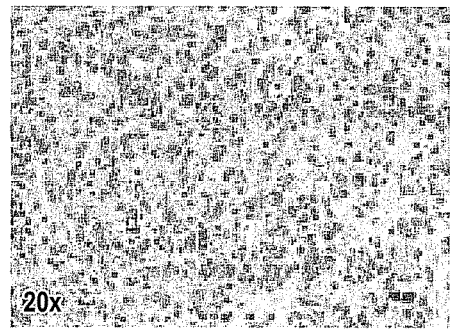
IHC : anti-Vasorin (R&D)

FIG. 19
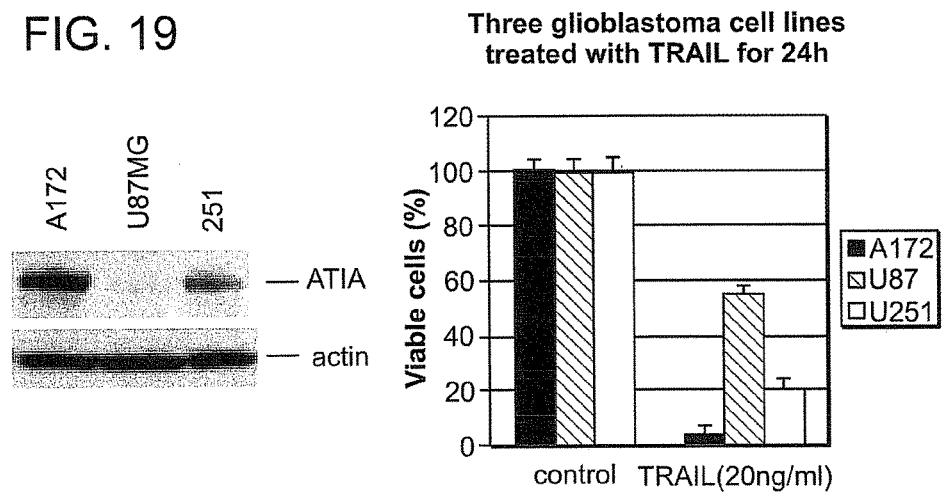
FIG. 20
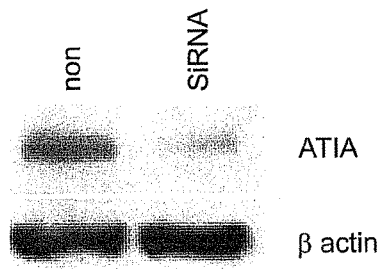
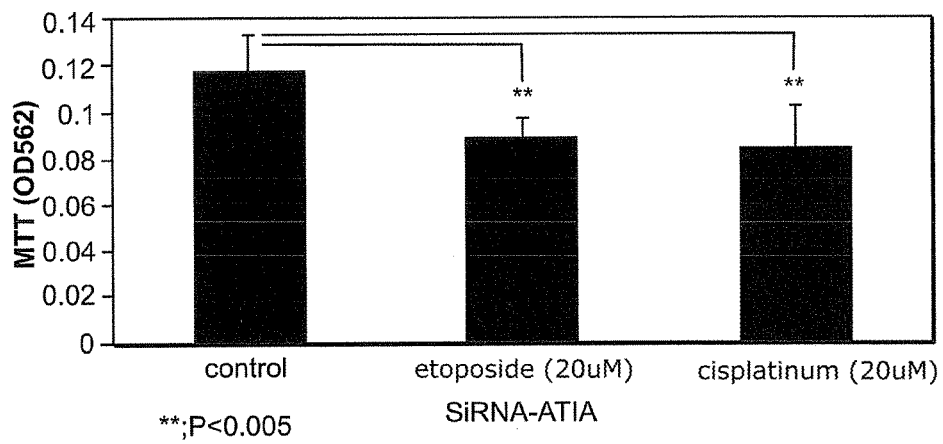
**;P<0.005

**; P<0.005

SEQUENCE LISTING

<160> NUMBER OF SEQ ID NOS: 11

<210> SEQ ID NO 1
<211> LENGTH: 3189
<212> TYPE: DNA
<213> ORGANISM: Mus musculus

<400> SEQUENCE: 1

```
agagaccagc ctcttacgag tcaacttcga gtctggagcc ggagccagag accggggctg    60
ggaaacccca gcccgggacg ggacgcagca gcctctggat cccgggaccc cggacctctc   120
aggaccggcc agaggtgaag gactgaggcc ccactgaggc cttggaccgc accgcctggc   180
tccttcagcc gcagtcgtct cctgggacag aagatgcact ccaggagctg cctgccacct   240
ctcctgttgt tgcttctggt gctcctgggg tctggagtac agggttgccc atcaggctgc   300
cagtgcaacc agccacagac agtcttctgc actgcccgtc agggaaccac agtgccccga   360
gacgtgccac ctgacacagt gggcctgtac atctttgaga acggcatcac gacacttgat   420
gtgggctgtt ttgctggcct tccgggcctg cagcttctgg acttgtcaca gaaccagatc   480
actagcctgc ccggggggcat cttcagcca cttgttaacc tcagtaacct ggacctgact   540
gccaacaaac tgcacgagat ctccaacgag accttccgtg gcctgcggcg cctggagcgc   600
ctctacctgg gcaagaaccg aattcgccac atccaaccgg gtgccttcga cgcgcttgat   660
cgcctcctgg agctcaagct gccagacaat gagcttcggg tgttgccccc attgcacttg   720
ccccgcctgc tgctgcttga cctcagccac aacagcatcc cagccctgga agccggaata   780
ctggataccg ccaatgtaga ggcattgagg ttggctggcc tagggctgcg gcagctggat   840 gagggcttt ttggccgcct tctcaacctc catgacttgg atgtttctga caaccagttg   900
gagcatatgc catctgtgat tcaaggcctg cgtggcctga cacgcctgcg gctggctggc   960
aacacccgta ttgcccagat acggcccgag gacctcgctg gtctgactgc cctacaggaa   1020
ttggatgtga gcaacctaag cctgcaggcc ctgcccagtg acctctcgag tctctttccc   1080
cgcctgcgcc tcttagcagc tgccaggaac cccttcaact gcttgtgccc cttgagctgg   1140
tttggtcctt gggtgcgtga gaaccatgtt gtgttggcca gccctgagga gacgcgttgt   1200
```

| | |
|---|---|
| cactttccac ccaagaatgc tggccgactg ctcctggatc tggattatgc agattttggc | 1260 |
| tgcccagtca ccactaccac ggccacagta cctactataa ggtctactat cagggaaccc | 1320 |
| acactttcaa cttctagcca agctcccacc tggcccagcc tcacagagcc aactacccag | 1380 |
| gcctccaccg tactatcgac tgccccacca accatgaggc cagtcctca gccccaggac | 1440 |
| tgtccagcat ccatctgcct gaatggtggt agctgccgtt gggagcaag acaccactgg | 1500 |
| gagtgcctat gccctgaggg cttcattggc ctgtactgtg agagtccagt ggagcaaggg | 1560 |
| atgaagccca gctccatacc agacactcca aggcccctc cactgctgcc tctcagcatt | 1620 |
| gagccggtga cccccaccctc cttgcgtgtg aagctgcagc gctacttgca gggtaacact | 1680 |
| gtgcagctac ggagcctccg gctcacctat cgcaacctgt ctggccctga caaacgactg | 1740 |
| gtgacattac ggctgcctgc ttcacttgca gagtatacag tcaccagct gcgacccaat | 1800 |
| gccacctatt ctatctgtgt cacacccttg ggagctggac ggacacctga aggtgaggag | 1860 |
| gcctgtgggg aggccaacac ttcccaggca gtccgctcta accatgcccc agttacccag | 1920 |
| gcccgtgagg gcaacctgcc actcctcatt gcgcctgccc tggctgctgt acttctggct | 1980 |
| gtgttagccg ctgcaggggc agcctactgt gtgcggcggg cacgggcaac ttctacagct | 2040 |
| caggacaaag gcaggtggg gccagggact ggacccctgg aactagaggg ggtgaaagcc | 2100 |
| cctttggagc caggctccaa ggcaacagag ggaggtgggg aggctttgtc aggtggtcct | 2160 |
| gaatgtgagg tgcctcttat gggctaccca gggcccagcc ttcagggggt cctccctgct | 2220 |
| aagcactaca tttagactgg tgagaaagag cagccagggg gtcaggcttt cagtcaccac | 2280 |
| cctcctgctg ccacagaagg aagttctcag tatacaccac agtgcacgtg catgatggag | 2340 |
| ctgtgggacc ctctctgggc tgggtctcat ctgtaagctg ctacagccca gatgaactct | 2400 |
| gccagccgcc agtgcatcca gtacagcgcc tgccatcttg tgcaatgtgc aaccctggga | 2460 |
| tgtgagccct gccatgtgct ggtaacatgg ctaggcatgt tgggcttccc aaaccatgga | 2520 |
| gtctggtaac cagtgaagga agcccccaga aataatgagt ggggaaggta ctagggcact | 2580 |
| ggccttggcc tcaaaagtgc aggcacactt gaaactggaa aggaaggtgc tctgggcaca | 2640 |
| tgtggatttg cttctattgt tttgttttgt tttttctaat gtatttataa agatcttttt | 2700 |
| cccatttatg ctgggaaagt gttttttcaaa ctcagtgaca aggactttgg ttttttgtaag | 2760 |
| actgttgatg atatgaaggc cttttgtaag aaaataaaaa ataaagtaaa ttgcctgtct | 2820 |
| ctctggttgg gcttgagatt taaggtctgt ggacatgcac aggattggag ggctgctgcc | 2880 |
| ctgccattag aatgctctag ccatgggtcc tgacccatgg taaggcttgc acttgggtgg | 2940 |
| ggccggaaaa tggacttgtt aggtagctta ccctaggcta ggcctcctct tctgccagca | 3000 |
| ggaaccacag tgcttaatgt ataaggcaga aaggggctca tagaaaacac agaacacaaa | 3060 |
| gggaggtcac atccctcctt gggtgttctg aaagtgcagt ccactatctt caactagaga | 3120 |
| agacagcctg gagcttcctc attctagagc ctaacagctg atcctgggac caggtggctt | 3180 |
| ccagactgg | 3189 |

<210> SEQ ID NO 2
<211> LENGTH: 673
<212> TYPE: PRT
<213> ORGANISM: Mus musculus

<400> SEQUENCE: 2

Met His Ser Arg Ser Cys Leu Pro Pro Leu Leu Leu Leu Leu Val
1               5                   10                  15

-continued

Leu Leu Gly Ser Gly Val Gln Gly Cys Pro Ser Gly Cys Gln Cys Asn
            20                  25                  30

Gln Pro Gln Thr Val Phe Cys Thr Ala Arg Gln Gly Thr Val Pro
        35                  40                  45

Arg Asp Val Pro Pro Asp Thr Val Gly Leu Tyr Ile Phe Glu Asn Gly
        50                  55                  60

Ile Thr Thr Leu Asp Val Gly Cys Phe Ala Gly Leu Pro Gly Leu Gln
65                  70                  75                  80

Leu Leu Asp Leu Ser Gln Asn Gln Ile Thr Ser Leu Pro Gly Gly Ile
                85                  90                  95

Phe Gln Pro Leu Val Asn Leu Ser Asn Leu Asp Leu Thr Ala Asn Lys
            100                 105                 110

Leu His Glu Ile Ser Asn Glu Thr Phe Arg Gly Leu Arg Arg Leu Glu
        115                 120                 125

Arg Leu Tyr Leu Gly Lys Asn Arg Ile Arg His Ile Gln Pro Gly Ala
        130                 135                 140

Phe Asp Ala Leu Asp Arg Leu Leu Glu Leu Lys Leu Pro Asp Asn Glu
145                 150                 155                 160

Leu Arg Val Leu Pro Pro Leu His Leu Pro Arg Leu Leu Leu Asp
                165                 170                 175

Leu Ser His Asn Ser Ile Pro Ala Leu Glu Ala Gly Ile Leu Asp Thr
            180                 185                 190

Ala Asn Val Glu Ala Leu Arg Leu Ala Gly Leu Gly Leu Arg Gln Leu
        195                 200                 205

Asp Glu Gly Leu Phe Gly Arg Leu Leu Asn Leu His Asp Leu Asp Val
210                 215                 220

Ser Asp Asn Gln Leu Glu His Met Pro Ser Val Ile Gln Gly Leu Arg
225                 230                 235                 240

Gly Leu Thr Arg Leu Arg Leu Ala Gly Asn Thr Arg Ile Ala Gln Ile
            245                 250                 255

Arg Pro Glu Asp Leu Ala Gly Leu Thr Ala Leu Gln Glu Leu Asp Val
        260                 265                 270

Ser Asn Leu Ser Leu Gln Ala Leu Pro Ser Asp Leu Ser Ser Leu Phe
    275                 280                 285

Pro Arg Leu Arg Leu Leu Ala Ala Ala Arg Asn Pro Phe Asn Cys Leu
    290                 295                 300

Cys Pro Leu Ser Trp Phe Gly Pro Trp Val Arg Glu Asn His Val Val
305                 310                 315                 320

Leu Ala Ser Pro Glu Glu Thr Arg Cys His Phe Pro Pro Lys Asn Ala
            325                 330                 335

Gly Arg Leu Leu Leu Asp Leu Asp Tyr Ala Asp Phe Gly Cys Pro Val
        340                 345                 350

Thr Thr Thr Thr Ala Thr Val Pro Thr Ile Arg Ser Thr Ile Arg Glu
        355                 360                 365

Pro Thr Leu Ser Thr Ser Ser Gln Ala Pro Thr Trp Pro Ser Leu Thr
    370                 375                 380

Glu Pro Thr Thr Gln Ala Ser Thr Val Leu Ser Thr Ala Pro Pro Thr
385                 390                 395                 400

Met Arg Pro Ala Pro Gln Pro Gln Asp Cys Pro Ala Ser Ile Cys Leu
            405                 410                 415

Asn Gly Gly Ser Cys Arg Leu Gly Ala Arg His His Trp Glu Cys Leu
        420                 425                 430

Cys Pro Glu Gly Phe Ile Gly Leu Tyr Cys Glu Ser Pro Val Glu Gln

```
                435                 440                 445
Gly Met Lys Pro Ser Ser Ile Pro Asp Thr Pro Arg Pro Pro Pro Leu
    450                 455                 460

Leu Pro Leu Ser Ile Glu Pro Val Ser Pro Thr Ser Leu Arg Val Lys
465                 470                 475                 480

Leu Gln Arg Tyr Leu Gln Gly Asn Thr Val Gln Leu Arg Ser Leu Arg
                485                 490                 495

Leu Thr Tyr Arg Asn Leu Ser Gly Pro Asp Lys Arg Leu Val Thr Leu
            500                 505                 510

Arg Leu Pro Ala Ser Leu Ala Glu Tyr Thr Val Thr Gln Leu Arg Pro
        515                 520                 525

Asn Ala Thr Tyr Ser Ile Cys Val Thr Pro Leu Gly Ala Gly Arg Thr
    530                 535                 540

Pro Glu Gly Glu Glu Ala Cys Gly Glu Ala Asn Thr Ser Gln Ala Val
545                 550                 555                 560

Arg Ser Asn His Ala Pro Val Thr Gln Ala Arg Glu Gly Asn Leu Pro
                565                 570                 575

Leu Leu Ile Ala Pro Ala Leu Ala Ala Val Leu Leu Ala Val Leu Ala
            580                 585                 590

Ala Ala Gly Ala Ala Tyr Cys Val Arg Arg Ala Arg Ala Thr Ser Thr
        595                 600                 605

Ala Gln Asp Lys Gly Gln Val Gly Pro Gly Thr Gly Pro Leu Glu Leu
    610                 615                 620

Glu Gly Val Lys Ala Pro Leu Glu Pro Gly Ser Lys Ala Thr Glu Gly
625                 630                 635                 640

Gly Gly Glu Ala Leu Ser Gly Gly Pro Glu Cys Glu Val Pro Leu Met
                645                 650                 655

Gly Tyr Pro Gly Pro Ser Leu Gln Gly Val Leu Pro Ala Lys His Tyr
            660                 665                 670

Ile

<210> SEQ ID NO 3
<211> LENGTH: 2739
<212> TYPE: DNA
<213> ORGANISM: Rattus norvegicus

<400> SEQUENCE: 3
ggagcccggg gttgggagac ccggacgcag tagcctccgg atcccgggac cccggacctt      60
tcaggaccgg ccggaggcga aggactgagg ccccattgag ccttgggcc gcaccgcccc      120 gctccctcag ccacagtcgt ctcccgggac agaagatgca ctccaggagc tgcctgccac      180
ctcttctgtt gttgctcctg gtgctcctgg ggtctggagt acagagctgc ccatcaggct      240
gccagtgcaa ccaaccacag acagtcttct gcactgcccg tcaggaacc acggtgcccc      300 gagacgtgcc gcctgacaca gtgggcctgt acatctttga gaacggcatc actacacttg      360
atgtaggctg ttttgctggc ttcccaggcc tgcagcttct ggacttgtca cagaaccaga      420
tcactagcct gccggtggc atctttcagc cacttgtgaa cctcagtaac ctggacctga      480
ctgctaacaa actgcacgag atctccaacg agaccttccg tggcctgcgg cgcctcgaac      540
gcctctacct gggcaagaac cgcattcgcc acatccagcc tggtgccttc gatgcacttg      600
accacctcct ggagctcaag ctgccagaca tgagcttcg ggtgctgccc ccactgcact      660
tgcctcgcct gctgctgctt gacctcagcc acaaacagtat cccagccctg gaagctggaa      720
tactggatac tgccaatgtg gaggcactgc ggctggctgg cctcgggctg cggcagctgg      780
```

```
atgagggget ttttggccgc cttcgcaacc tccatgacct ggatgtttct gacaaccagt    840
tggggcacat gccctccgtg attcaaggcc tgcgtggcct acacgcctg cggctggctg     900
gcaacacccg gattgcccag atccggcccg aggacctcgc tggcctgact gccctacagg    960
aactggatgt gagcaacctg agcctgcagg ccctgcccag tgacctctcc agtctctttc   1020
cccgcctgcg cctcctagca gctgcccgaa accccttaa ctgcttatgc cccttgagct    1080
ggtttggtcc ttgggttcgt gagagccatg ttgtgctggc cagccctgag agacacgtt    1140
gtcacttccc acccaagaac gccggccgac tgctcctgga gctggattat gcagattttg   1200
gctgcccagt caccactacc acagccacag ttcctactat aaggcctact gtcagggagc   1260
ccacaccttc aacttccagc aagctccca cctggcccag ccccacagag ccaactaccc     1320
aggcccccat cgtactgtcc actgcccac caaccatgag gccggctcct cagccccagg    1380
actgtccagc atccatctgc ctgaatggtg gtagctgccg tgtaggggca aaacaccacc   1440
tggagtgcct gtgccccgag ggcttcattg gcctgtactg tgagagtccc gtggaacaaa   1500
ggacaaagcc cagctccata ccggacaccc cacggccccc gcggctgctg cctctgcgca   1560
ttgagccggt gagccccacc tccctgcgtg tggagctgca gcgctacctg cagggcaaca   1620
ccgtgcagct gcggagcctc cggctcacct accgcaacct gtctggccct gacaagcggc   1680
tggtgacgct gcggctgcct gcttcacttg cagagtacac agtcacccag ctgcggccca   1740
atgccaccta ttctatctgt gtcacagccc tgggagctgg gcggacacct gaaggtgagg   1800
aggcctgtgg ggaggccaac actccccagg ccgtccgctc caaccatgcc ccagtcaccc   1860
aggcccggga gggcaacctg ccactcctca ttgcacccgc cctggctgct gtgcttctgg   1920
ctgtgttggc tgcctcgggg gcagtctact gtgtgcgacg ggcgcgggca agttccacag   1980
ctcaggacaa agggcaggtg ggaccaggga ccggccccct ggaactagag ggggtgaaag   2040
tccccttgga gccaggctcc aaggcatcag agggaggcgg ggaggcccta tcaggtggtc   2100
ctgaatgtga ggtgccectc atgggctacc cagggcccag tcttcagggg gtcctccctg   2160
ctcagcccta catttaagca cgtgagaagg agcagccagg aggctgggct tcagtctcc    2220
accctcctgc tgctacagaa ggaagttctc aatgcgcacc acagtgcaca tgtgtgaccg   2280
gtgctgtggg acagcagcca gtccccgacc ctctctgggc tgggtcatct gaaagctgct   2340
acagcccaaa tgaactccca gcaccagcat ccagtacaga gcctgctgcc ttgcgcagtc   2400
tgcagtcctg ggacgggaac cctgccatgt gctggtagca tggctaggat gttgggcttc   2460
ccgggccctg ggtctggta accagtgaag gaagcccca aaaatagtgg gtagggaagg     2520
cactagggcc gtggccgtgg ccccgaaagt gcaggaacac ttgaaactgg aaaggaaggt   2580
gctctgggca cacgtggatt tgcttctatt gttttgtttt tctcctaatg tatttataaa   2640
agatcttttc ccgtttatgc tgggaaaaag tgtttttcaa actcagtgac aaggactttt   2700
ggttttgta agactattga tgatatgaag gccttttgt                            2739
```

<210> SEQ ID NO 4
<211> LENGTH: 673
<212> TYPE: PRT
<213> ORGANISM: Rattus norvegicus

<400> SEQUENCE: 4

Met His Ser Arg Ser Cys Leu Pro Pro Leu Leu Leu Leu Leu Leu Val
1               5                   10                  15

Leu Leu Gly Ser Gly Val Gln Ser Cys Pro Ser Gly Cys Gln Cys Asn

-continued

```
             20                  25                  30
Gln Pro Gln Thr Val Phe Cys Thr Ala Arg Gln Gly Thr Thr Val Pro
             35                  40                  45
Arg Asp Val Pro Pro Asp Thr Val Gly Leu Tyr Ile Phe Glu Asn Gly
 50                  55                  60
Ile Thr Thr Leu Asp Val Gly Cys Phe Ala Gly Phe Pro Gly Leu Gln
 65                  70                  75                  80
Leu Leu Asp Leu Ser Gln Asn Gln Ile Thr Ser Leu Pro Gly Gly Ile
                 85                  90                  95
Phe Gln Pro Leu Val Asn Leu Ser Asn Leu Asp Leu Thr Ala Asn Lys
                100                 105                 110
Leu His Glu Ile Ser Asn Glu Thr Phe Arg Gly Leu Arg Arg Leu Glu
                115                 120                 125
Arg Leu Tyr Leu Gly Lys Asn Arg Ile Arg His Ile Gln Pro Gly Ala
                130                 135                 140
Phe Asp Ala Leu Asp His Leu Leu Glu Leu Lys Leu Pro Asp Asn Glu
145                 150                 155                 160
Leu Arg Val Leu Pro Pro Leu His Leu Pro Arg Leu Leu Leu Leu Asp
                165                 170                 175
Leu Ser His Asn Ser Ile Pro Ala Leu Glu Ala Gly Ile Leu Asp Thr
                180                 185                 190
Ala Asn Val Glu Ala Leu Arg Leu Ala Gly Leu Gly Leu Arg Gln Leu
                195                 200                 205
Asp Glu Gly Leu Phe Gly Arg Leu Arg Asn Leu His Asp Leu Asp Val
                210                 215                 220
Ser Asp Asn Gln Leu Gly His Met Pro Ser Val Ile Gln Gly Leu Arg
225                 230                 235                 240
Gly Leu Thr Arg Leu Arg Leu Ala Gly Asn Thr Arg Ile Ala Gln Ile
                245                 250                 255
Arg Pro Glu Asp Leu Ala Gly Leu Thr Ala Leu Gln Glu Leu Asp Val
                260                 265                 270
Ser Asn Leu Ser Leu Gln Ala Leu Pro Ser Asp Leu Ser Ser Leu Phe
                275                 280                 285
Pro Arg Leu Arg Leu Leu Ala Ala Ala Arg Asn Pro Phe Asn Cys Leu
                290                 295                 300
Cys Pro Leu Ser Trp Phe Gly Pro Trp Val Arg Glu Ser His Val Val
305                 310                 315                 320
Leu Ala Ser Pro Glu Glu Thr Arg Cys His Phe Pro Pro Lys Asn Ala
                325                 330                 335
Gly Arg Leu Leu Leu Glu Leu Asp Tyr Ala Asp Phe Gly Cys Pro Val
                340                 345                 350
Thr Thr Thr Thr Ala Thr Val Pro Thr Ile Arg Pro Thr Val Arg Glu
                355                 360                 365
Pro Thr Pro Ser Thr Ser Ser Gln Ala Pro Thr Trp Pro Ser Pro Thr
                370                 375                 380
Glu Pro Thr Thr Gln Ala Pro Ile Val Leu Ser Thr Ala Pro Pro Thr
385                 390                 395                 400
Met Arg Pro Ala Pro Gln Pro Gln Asp Cys Pro Ala Ser Ile Cys Leu
                405                 410                 415
Asn Gly Gly Ser Cys Arg Val Gly Ala Lys His His Leu Glu Cys Leu
                420                 425                 430
Cys Pro Glu Gly Phe Ile Gly Leu Tyr Cys Glu Ser Pro Val Glu Gln
                435                 440                 445
```

```
Arg Thr Lys Pro Ser Ser Ile Pro Asp Thr Pro Arg Pro Pro Arg Leu
        450                 455                 460

Leu Pro Leu Arg Ile Glu Pro Val Ser Pro Thr Ser Leu Arg Val Glu
465                 470                 475                 480

Leu Gln Arg Tyr Leu Gln Gly Asn Thr Val Gln Leu Arg Ser Leu Arg
                485                 490                 495

Leu Thr Tyr Arg Asn Leu Ser Gly Pro Asp Lys Arg Leu Val Thr Leu
            500                 505                 510

Arg Leu Pro Ala Ser Leu Ala Glu Tyr Thr Val Thr Gln Leu Arg Pro
        515                 520                 525

Asn Ala Thr Tyr Ser Ile Cys Val Thr Ala Leu Gly Ala Gly Arg Thr
    530                 535                 540

Pro Glu Gly Glu Glu Ala Cys Gly Glu Ala Asn Thr Pro Gln Ala Val
545                 550                 555                 560

Arg Ser Asn His Ala Pro Val Thr Gln Ala Arg Glu Gly Asn Leu Pro
                565                 570                 575

Leu Leu Ile Ala Pro Ala Leu Ala Ala Val Leu Leu Ala Val Leu Ala
            580                 585                 590

Ala Ser Gly Ala Val Tyr Cys Val Arg Arg Ala Arg Ala Ser Ser Thr
        595                 600                 605

Ala Gln Asp Lys Gly Gln Val Gly Pro Gly Thr Gly Pro Leu Glu Leu
    610                 615                 620

Glu Gly Val Lys Val Pro Leu Glu Pro Gly Ser Lys Ala Ser Glu Gly
625                 630                 635                 640

Gly Gly Glu Ala Leu Ser Gly Pro Glu Cys Glu Val Pro Leu Met
                645                 650                 655

Gly Tyr Pro Gly Pro Ser Leu Gln Gly Val Leu Pro Ala Gln Pro Tyr
            660                 665                 670

Ile

<210> SEQ ID NO 5
<211> LENGTH: 2864
<212> TYPE: DNA
<213> ORGANISM: Homo sapiens

<400> SEQUENCE: 5
gactccggag cccgagcccg gggcgggtgg acgcggactc gaacgcagtt gcttcgggac      60
ccaggacccc ctcgggcccg acccgccagg aaagactgag gccgcggcct gccccgcccg     120
gctccctgcg ccgccgccgc ctcccgggac agaagatgtg ctccagggtc cctctgctgc     180
tgccgctgct cctgctactg gccctggggc ctggggtgca gggctgccca tccggctgcc     240
agtgcagcca gccacagaca gtcttctgca ctgcccgcca ggggaccacg gtgccccgag     300
acgtgccacc cgacacggtg gggctgtacg tctttgagaa cggcatcacc atgctcgacg     360
caggcagctt tgccggcctg ccgggcctgc agctcctgga cctgtcacag aaccagatcg     420
ccagcctgcc cagcggggtc ttccagccac tcgccaacct cagcaacctg gacctgacag     480
ccaacaggct gcatgaaatc accaatgaga ccttccgtgg cctgcggcgc ctcgagcgcc     540
tctacctggg caagaaccgc atccgccaca tccagcctgg tgccttcgac acgctcgacc     600
gcctcctgga gctcaagctg caggacaacg agctgcgggc actgccccgc tgcgcctgc      660 cccgcctgct gctgctggac ctcagccaca acagcctcct ggccctggag cccgcatcc      720 tggacactgc caacgtggag gcgctgcggc tggctggtct ggggctgcag cagctggacg     780
```

```
agggggctctt cagccgcttg cgcaacctcc acgacctgga tgtgtccgac aaccagctgg    840
agcgagtgcc acctgtgatc cgaggcctcc ggggcctgac gcgcctgcgg ctggccggca    900
acacccgcat tgcccagctg cggcccgagg acctggccgg cctggctgcc ctgcaggagc    960
tggatgtgag caacctaagc ctgcaggccc tgcctggcga cctctcgggc tcttccccc   1020
gcctgcggct gctggcagct gcccgcaacc ccttcaactg cgtgtgcccc ctgagctggt   1080
ttggcccctg ggtgcgcgag agccacgtca cactggccag ccctgaggag acgcgctgcc   1140
acttcccgcc caagaacgct ggccggctgc tcctggagct tgactacgcc gactttggct   1200
gcccagccac caccaccaca gccacagtgc caccgcgag gccgtggtg cgggagccca    1260
cagccttgtc ttctagcttg gctcctacct ggcttagccc cacagagccg gccactgagg   1320
cccccagccc gccctccact gccccaccga ctgtagggcc tgtccccag ccccaggact    1380
gcccaccgtc cacctgcctc aatggggca catgccacct ggggacacgg caccacctgg    1440
cgtgcttgtg ccccgaaggc ttcacgggcc tgtactgtga gagccagatg gggcagggga    1500
cacggcccag ccctacacca gtcacgccga ggccaccacg gtccctgacc ctgggcatcg   1560
agccggtgag ccccacctcc ctgcgcgtgg ggctgcagcg ctacctccag gggagctccg   1620
tgcagctcag gagcctccgt ctcacctatc gcaacctatc gggccctgat aagcggctgg   1680
tgacgctgcg actgcctgcc tcgctcgctg agtacacggt cacccagctg cggcccaacg   1740
ccacttactc cgtctgtgtc atgcctttgg ggcccgggcg ggtgccggag ggcgaggagg   1800
cctgcgggga ggcccataca ccccagccg tccactccaa ccacgcccca gtcacccagg    1860
cccgcgaggg caacctgccg ctcctcattg cgcccgccct ggccgcggtg ctcctggccg   1920
cgctggctgc ggtgggggca gcctactgtg tgcggcgggg gcgggccatg gcagcagcgg   1980
ctcaggacaa agggcaggtg gggccagggg ctgggcccct ggaactggag ggagtgaagg   2040
tccccttgga gccaggcccg aaggcaacag agggcggtgg agaggccctg cccagcgggt   2100
ctgagtgtga ggtgccactc atgggcttcc cagggcctgg cctccagtca cccctccacg   2160
caaagcccta catctaagcc agagagagac agggcagctg gggccgggct ctcagccagt   2220
gagatggcca gcccctcct gctgccacac cacgtaagtt ctcagtccca acctcgggga    2280
tgtgtgcaga cagggctgtg tgaccacagc tgggccctgt ccctctggaa cctcggtctc   2340
ctcatctgtg agatgctgtg gcccagctga cgagccctaa cgtccccaga accgagtgcc   2400
tatgaggaca gtgtccgccc tgccctccgc aacgtgcagt ccctgggcac ggcgggccct   2460
gccatgtgct ggtaacgcat gcctgggccc tgctgggctc tcccactcca ggcggaccct   2520
gggggccagt gaaggaagct cccggaaaga gcagagggag agcgggtagg cggctgtgtg   2580
actctagtct tggccccagg aagcgaagga acaaaagaaa ctggaaagga agatgcttta   2640
ggaacatgtt ttgcttttt aaaatatata tatatttata agagatcctt tcccatttat    2700
tctgggaaga tgtttttcaa actcagagac aaggactttg gttttgtaa dacaaacgat    2760
gatatgaagg ccttttgtaa gaaaaataa aagatgaagt gtgtttaaaa aaaaaaaaa    2820
aaaaaaaaaa aaaaaaaaaa aaaaaaaaaa aaaaaaaaaa aaaa                   2864
```

<210> SEQ ID NO 6
<211> LENGTH: 673
<212> TYPE: PRT
<213> ORGANISM: Homo sapiens

<400> SEQUENCE: 6

Met Cys Ser Arg Val Pro Leu Leu Leu Pro Leu Leu Leu Leu Leu Ala

```
1               5                   10                  15
Leu Gly Pro Gly Val Gln Gly Cys Pro Ser Gly Cys Gln Cys Ser Gln
                20                  25                  30
Pro Gln Thr Val Phe Cys Thr Ala Arg Gln Gly Thr Thr Val Pro Arg
                35                  40                  45
Asp Val Pro Pro Asp Thr Val Gly Leu Tyr Val Phe Glu Asn Gly Ile
50                  55                  60
Thr Met Leu Asp Ala Gly Ser Phe Ala Gly Leu Pro Gly Leu Gln Leu
65                  70                  75                  80
Leu Asp Leu Ser Gln Asn Gln Ile Ala Ser Leu Pro Ser Gly Val Phe
                85                  90                  95
Gln Pro Leu Ala Asn Leu Ser Asn Leu Asp Leu Thr Ala Asn Arg Leu
                100                 105                 110
His Glu Ile Thr Asn Glu Thr Phe Arg Gly Leu Arg Arg Leu Glu Arg
                115                 120                 125
Leu Tyr Leu Gly Lys Asn Arg Ile Arg His Ile Gln Pro Gly Ala Phe
                130                 135                 140
Asp Thr Leu Asp Arg Leu Leu Glu Leu Lys Leu Gln Asp Asn Glu Leu
145                 150                 155                 160
Arg Ala Leu Pro Pro Leu Arg Leu Pro Arg Leu Leu Leu Leu Asp Leu
                165                 170                 175
Ser His Asn Ser Leu Leu Ala Leu Glu Pro Gly Ile Leu Asp Thr Ala
                180                 185                 190
Asn Val Glu Ala Leu Arg Leu Ala Gly Leu Gly Leu Gln Gln Leu Asp
                195                 200                 205
Glu Gly Leu Phe Ser Arg Leu Arg Asn Leu His Asp Leu Asp Val Ser
                210                 215                 220
Asp Asn Gln Leu Glu Arg Val Pro Pro Val Ile Arg Gly Leu Arg Gly
225                 230                 235                 240
Leu Thr Arg Leu Arg Leu Ala Gly Asn Thr Arg Ile Ala Gln Leu Arg
                245                 250                 255
Pro Glu Asp Leu Ala Gly Leu Ala Ala Leu Gln Glu Leu Asp Val Ser
                260                 265                 270
Asn Leu Ser Leu Gln Ala Leu Pro Gly Asp Leu Ser Gly Leu Phe Pro
                275                 280                 285
Arg Leu Arg Leu Leu Ala Ala Ala Arg Asn Pro Phe Asn Cys Val Cys
                290                 295                 300
Pro Leu Ser Trp Phe Gly Pro Trp Val Arg Glu Ser His Val Thr Leu
305                 310                 315                 320
Ala Ser Pro Glu Glu Thr Arg Cys His Phe Pro Pro Lys Asn Ala Gly
                325                 330                 335
Arg Leu Leu Leu Glu Leu Asp Tyr Ala Asp Phe Gly Cys Pro Ala Thr
                340                 345                 350
Thr Thr Thr Ala Thr Val Pro Thr Thr Arg Pro Val Val Arg Glu Pro
                355                 360                 365
Thr Ala Leu Ser Ser Ser Leu Ala Pro Thr Trp Leu Ser Pro Thr Glu
                370                 375                 380
Pro Ala Thr Glu Ala Pro Ser Pro Ser Thr Ala Pro Pro Thr Val
385                 390                 395                 400
Gly Pro Val Pro Gln Pro Gln Asp Cys Pro Pro Ser Thr Cys Leu Asn
                405                 410                 415
Gly Gly Thr Cys His Leu Gly Thr Arg His His Leu Ala Cys Leu Cys
                420                 425                 430
```

Pro Glu Gly Phe Thr Gly Leu Tyr Cys Glu Ser Gln Met Gly Gln Gly
            435                 440                 445

Thr Arg Pro Ser Pro Thr Pro Val Thr Pro Arg Pro Arg Ser Leu
450                 455                 460

Thr Leu Gly Ile Glu Pro Val Ser Pro Thr Ser Leu Arg Val Gly Leu
465                 470                 475                 480

Gln Arg Tyr Leu Gln Gly Ser Ser Val Gln Leu Arg Ser Leu Arg Leu
                485                 490                 495

Thr Tyr Arg Asn Leu Ser Gly Pro Asp Lys Arg Leu Val Thr Leu Arg
                500                 505                 510

Leu Pro Ala Ser Leu Ala Glu Tyr Thr Val Thr Gln Leu Arg Pro Asn
                515                 520                 525

Ala Thr Tyr Ser Val Cys Val Met Pro Leu Gly Pro Gly Arg Val Pro
                530                 535                 540

Glu Gly Glu Glu Ala Cys Gly Glu Ala His Thr Pro Pro Ala Val His
545                 550                 555                 560

Ser Asn His Ala Pro Val Thr Gln Ala Arg Glu Gly Asn Leu Pro Leu
                565                 570                 575

Leu Ile Ala Pro Ala Leu Ala Ala Val Leu Leu Ala Ala Leu Ala Ala
                580                 585                 590

Val Gly Ala Ala Tyr Cys Val Arg Arg Gly Arg Ala Met Ala Ala Ala
                595                 600                 605

Ala Gln Asp Lys Gly Gln Val Gly Pro Gly Ala Gly Pro Leu Glu Leu
                610                 615                 620

Glu Gly Val Lys Val Pro Leu Glu Pro Gly Pro Lys Ala Thr Glu Gly
625                 630                 635                 640

Gly Gly Glu Ala Leu Pro Ser Gly Ser Glu Cys Glu Val Pro Leu Met
                645                 650                 655

Gly Phe Pro Gly Pro Gly Leu Gln Ser Pro Leu His Ala Lys Pro Tyr
                660                 665                 670

Ile

<210> SEQ ID NO 7
<211> LENGTH: 1501
<212> TYPE: DNA
<213> ORGANISM: Mus musculus

<400> SEQUENCE: 7
tcaggctgcc agtgcaacca gccacagaca gtcttctgca ctgcccgtca gggaaccaca      60
gtgccccgag acgtgccacc tgacacagtg ggcctgtaca tctttgagaa cggcatcacg     120
acacttgatg tgggctgttt tgctggcctt ccgggcctgc agcttctgga cttgtcacag     180
aaccagatca ctagcctgcc gggggcatc tttcagccac ttgttaacct cagtaacctg     240
gacctgactg ccaacaaact gcacgagatc tccaacgaga ccttccgtgg cctgcggcgc     300
ctggagcgcc tctacctggg caagaaccga attcgccaca tccaaccggg tgccttcgac     360
gcgcttgatc gcctcctgga gctcaagctg ccagacaatg agcttcgggt gttgccccca     420
ttgcacttgc cccgcctgct gctgcttgac ctcagccaca cagcatccc agccctggaa     480 gccggaatac tggataccgc caatgtagag gcattgaggt tggctggcct agggctgcgg     540
cagctggatg aggggctttt tggccgcctt ctcaacctcc atgacttgga tgtttctgac     600
aaccagttgg agcatatgcc atctgtgatt caaggcctgc gtggcctgac acgcctgcgg     660
ctggctggca cacccgtat tgcccagata cggcccgagg acctcgctgg tctgactgcc     720

```
ctacaggaat tggatgtgag caacctaagc ctgcaggccc tgcccagtga cctctcgagt        780
ctctttcccc gcctgcgcct cttagcagct gccaggaacc ccttcaactg cttgtgcccc        840
ttgagctggt ttggtccttg ggtgcgtgag aaccatgttg tgttggccag ccctgaggag        900
acgcgttgtc actttccacc caagaatgct ggccgactgc tcctggatct ggattatgca        960
gattttggct gcccagtcac cactaccacg ccacagtac ctactataag gtctactatc       1020
agggaaccca cactttcaac ttctagccaa gctcccacct ggcccagcct cacagagcca       1080
actacccagg cctccaccgt actatcgact gccccaccaa ccatgaggcc agctcctcag       1140
ccccaggact gtccagcatc catctgcctg aatggtggta gctgccgttt gggagcaaga       1200
caccactggg agtgcctatg ccctgagggc ttcattggcc tgtactgtga gagtccagtg       1260
gagcaaggga tgaagcccag ctccatacca gacactccaa ggcccctcc actgctgcct        1320 ctcagcattg agccggtgag ccccaccctcc ttgcgtgtga agctgcagcg ctacttgcag      1380
ggtaacactg tgcagctacg gagcctccgg ctcacctatc gcaacctgtc tggccctgac       1440
aaacgactgg tgacattacg gctgcctgct tcacttgcag agtatacagt cacccagctg       1500
c                                                                     1501

<210> SEQ ID NO 8
<211> LENGTH: 1501
<212> TYPE: DNA
<213> ORGANISM: Homo sapiens

<400> SEQUENCE: 8
tccggctgcc agtgcagcca gccacagaca gtcttctgca ctgcccgcca ggggaccacg         60
gtgccccgag acgtgccacc cgacacggtg gggctgtacg tctttgagaa cggcatcacc        120
atgctcgacg caggcagctt tgccggcctg ccgggcctgc agctcctgga cctgtcacag        180
aaccagatcg ccagcctgcc cagcggggtc ttccagccac tcgccaacct cagcaacctg        240
gacctgacag ccaacaggct gcatgaaatc accaatgaga ccttccgtgg cctgcggcgc        300
ctcgagcgcc tctacctggg caagaaccgc atccgccaca tccagcctgg tgccttcgac        360
acgctcgacc gcctcctgga gctcaagctg caggacaacg agctgcgggc actgcccccg        420
ctgcgcctgc cccgcctgct gctgctggac ctcagccaca acagcctcct ggccctggag        480
cccggcatcc tggacactgc caacgtggag gcgctgcggc tggctggtct ggggctgcag        540
cagctggacg aggggctctt cagccgcttg cgcaacctcc acgacctgga tgtgtccgac        600
aaccagctga gcgagtgcc acctgtgatc cgaggcctcc ggggcctgac cgcctgcgg         660 ctggccggca acacccgcat tgcccagctg cggcccgagg acctggccgg cctggctgcc       720
ctgcaggagc tggatgtgag caacctaagc ctgcaggccc tgcctggcga cctctcgggc       780
ctcttccccc gcctgcggct gctggcagct gcccgcaacc ccttcaactg cgtgtgcccc       840
ctgagctggt ttggcccctg ggtgcgcgag agccacgtca cactgccag ccctgaggag        900 acgcgctgcc acttcccgcc caagaacgct ggccggctgc tcctggagct tgactacgcc       960
gactttggct gcccagccac caccaccaca gccacagtgc ccaccacgag gcccgtggtg      1020
cgggagccca cagccttgtc ttctagcttg gctcctacct ggcttagccc cacagagccg       1080
gccactgagg ccccccagccc gccctccact gccccaccga ctgtagggcc tgtcccccag      1140
ccccaggact gccaccgtc cacctgcctc aatgggggca catgccacct ggggacacgg       1200
caccacctgg cgtgcttgtg cccgaaggc ttcacggggc tgtactgtga gagccagatg       1260
```

```
gggcagggga cacggcccag ccctacacca gtcacgccga ggccaccacg gtccctgacc    1320
ctgggcatcg agccggtgag ccccacctcc ctgcgcgtgg ggctgcagcg ctacctccag    1380
gggagctccg tgcagctcag gagcctccgt ctcacctatc gcaacctatc gggccctgat    1440
aagcggctgg tgacgctgcg actgcctgcc tcgctcgctg agtacacggt cacccagctg    1500
c                                                                    1501
```

<210> SEQ ID NO 9
<211> LENGTH: 501
<212> TYPE: PRT
<213> ORGANISM: Mus musculus

<400> SEQUENCE: 9

```
Pro Ser Gly Cys Gln Cys Asn Gln Pro Gln Thr Val Phe Cys Thr Ala
1               5                   10                  15

Arg Gln Gly Thr Thr Val Pro Arg Asp Val Pro Asp Thr Val Gly
            20                  25                  30

Leu Tyr Ile Phe Glu Asn Gly Ile Thr Thr Leu Asp Val Gly Cys Phe
            35                  40                  45

Ala Gly Leu Pro Gly Leu Gln Leu Leu Asp Leu Ser Gln Asn Gln Ile
50                  55                  60

Thr Ser Leu Pro Gly Gly Ile Phe Gln Pro Leu Val Asn Leu Ser Asn
65                  70                  75                  80

Leu Asp Leu Thr Ala Asn Lys Leu His Glu Ile Ser Asn Glu Thr Phe
                85                  90                  95

Arg Gly Leu Arg Arg Leu Glu Arg Leu Tyr Leu Gly Lys Asn Arg Ile
            100                 105                 110

Arg His Ile Gln Pro Gly Ala Phe Asp Ala Leu Asp Arg Leu Leu Glu
        115                 120                 125

Leu Lys Leu Pro Asp Asn Glu Leu Arg Val Leu Pro Pro Leu His Leu
130                 135                 140

Pro Arg Leu Leu Leu Leu Asp Leu Ser His Asn Ser Ile Pro Ala Leu
145                 150                 155                 160

Glu Ala Gly Ile Leu Asp Thr Ala Asn Val Glu Ala Leu Arg Leu Ala
                165                 170                 175

Gly Leu Gly Leu Arg Gln Leu Asp Glu Gly Leu Phe Gly Arg Leu Leu
            180                 185                 190

Asn Leu His Asp Leu Asp Val Ser Asp Asn Gln Leu Glu His Met Pro
        195                 200                 205

Ser Val Ile Gln Gly Leu Arg Gly Leu Thr Arg Leu Arg Leu Ala Gly
210                 215                 220

Asn Thr Arg Ile Ala Gln Ile Arg Pro Glu Asp Leu Ala Gly Leu Thr
225                 230                 235                 240

Ala Leu Gln Glu Leu Asp Val Ser Asn Leu Ser Leu Gln Ala Leu Pro
                245                 250                 255

Ser Asp Leu Ser Ser Leu Phe Pro Arg Leu Arg Leu Leu Ala Ala Ala
            260                 265                 270

Arg Asn Pro Phe Asn Cys Leu Cys Pro Leu Ser Trp Phe Gly Pro Trp
        275                 280                 285

Val Arg Glu Asn His Val Val Leu Ala Ser Pro Glu Glu Thr Arg Cys
290                 295                 300

His Phe Pro Pro Lys Asn Ala Gly Arg Leu Leu Leu Asp Leu Asp Tyr
305                 310                 315                 320

Ala Asp Phe Gly Cys Pro Val Thr Thr Thr Thr Ala Thr Val Pro Thr
```

```
            325                 330                 335
Ile Arg Ser Thr Ile Arg Glu Pro Thr Leu Ser Thr Ser Ser Gln Ala
            340                 345                 350
Pro Thr Trp Pro Ser Leu Thr Glu Pro Thr Thr Gln Ala Ser Thr Val
            355                 360                 365
Leu Ser Thr Ala Pro Pro Thr Met Arg Pro Ala Pro Gln Pro Gln Asp
            370                 375                 380
Cys Pro Ala Ser Ile Cys Leu Asn Gly Gly Ser Cys Arg Leu Gly Ala
385                 390                 395                 400
Arg His His Trp Glu Cys Leu Cys Pro Glu Gly Phe Ile Gly Leu Tyr
            405                 410                 415
Cys Glu Ser Pro Val Glu Gln Gly Met Lys Pro Ser Ser Ile Pro Asp
            420                 425                 430
Thr Pro Arg Pro Pro Leu Leu Pro Leu Ser Ile Glu Pro Val Ser
            435                 440                 445
Pro Thr Ser Leu Arg Val Lys Leu Gln Arg Tyr Leu Gln Gly Asn Thr
            450                 455                 460
Val Gln Leu Arg Ser Leu Arg Leu Thr Tyr Arg Asn Leu Ser Gly Pro
465                 470                 475                 480
Asp Lys Arg Leu Val Thr Leu Arg Leu Pro Ala Ser Leu Ala Glu Tyr
            485                 490                 495
Thr Val Thr Gln Leu
            500

<210> SEQ ID NO 10
<211> LENGTH: 501
<212> TYPE: PRT
<213> ORGANISM: Homo sapiens

<400> SEQUENCE: 10

Pro Ser Gly Cys Gln Cys Ser Gln Pro Gln Thr Val Phe Cys Thr Ala
1               5                   10                  15
Arg Gln Gly Thr Thr Val Pro Arg Asp Val Pro Pro Asp Thr Val Gly
            20                  25                  30
Leu Tyr Val Phe Glu Asn Gly Ile Thr Met Leu Asp Ala Gly Ser Phe
            35                  40                  45
Ala Gly Leu Pro Gly Leu Gln Leu Leu Asp Leu Ser Gln Asn Gln Ile
        50                  55                  60
Ala Ser Leu Pro Ser Gly Val Phe Gln Pro Leu Ala Asn Leu Ser Asn
65                  70                  75                  80
Leu Asp Leu Thr Ala Asn Arg Leu His Glu Ile Thr Asn Glu Thr Phe
            85                  90                  95
Arg Gly Leu Arg Arg Leu Glu Arg Leu Tyr Leu Gly Lys Asn Arg Ile
            100                 105                 110
Arg His Ile Gln Pro Gly Ala Phe Asp Thr Leu Asp Arg Leu Leu Glu
            115                 120                 125
Leu Lys Leu Gln Asp Asn Glu Leu Arg Ala Leu Pro Pro Leu Arg Leu
        130                 135                 140
Pro Arg Leu Leu Leu Leu Asp Leu Ser His Asn Ser Leu Leu Ala Leu
145                 150                 155                 160
Glu Pro Gly Ile Leu Asp Thr Ala Asn Val Glu Ala Leu Arg Leu Ala
            165                 170                 175
Gly Leu Gly Leu Gln Gln Leu Asp Glu Gly Leu Phe Ser Arg Leu Arg
            180                 185                 190
```

```
Asn Leu His Asp Leu Asp Val Ser Asp Asn Gln Leu Glu Arg Val Pro
            195                 200                 205

Pro Val Ile Arg Gly Leu Arg Gly Leu Thr Arg Leu Arg Leu Ala Gly
    210                 215                 220

Asn Thr Arg Ile Ala Gln Leu Arg Pro Glu Asp Leu Ala Gly Leu Ala
225                 230                 235                 240

Ala Leu Gln Glu Leu Asp Val Ser Asn Leu Ser Leu Gln Ala Leu Pro
                245                 250                 255

Gly Asp Leu Ser Gly Leu Phe Pro Arg Leu Arg Leu Ala Ala Ala
            260                 265                 270

Arg Asn Pro Phe Asn Cys Val Cys Pro Leu Ser Trp Phe Gly Pro Trp
        275                 280                 285

Val Arg Glu Ser His Val Thr Leu Ala Ser Pro Glu Glu Thr Arg Cys
    290                 295                 300

His Phe Pro Pro Lys Asn Ala Gly Arg Leu Leu Leu Glu Leu Asp Tyr
305                 310                 315                 320

Ala Asp Phe Gly Cys Pro Ala Thr Thr Thr Ala Thr Val Pro Thr
                325                 330                 335

Thr Arg Pro Val Val Arg Glu Pro Thr Ala Leu Ser Ser Ser Leu Ala
            340                 345                 350

Pro Thr Trp Leu Ser Pro Thr Glu Pro Ala Thr Glu Ala Pro Ser Pro
        355                 360                 365

Pro Ser Thr Ala Pro Pro Thr Val Gly Pro Val Pro Gln Pro Gln Asp
    370                 375                 380

Cys Pro Pro Ser Thr Cys Leu Asn Gly Gly Thr Cys His Leu Gly Thr
385                 390                 395                 400

Arg His His Leu Ala Cys Leu Cys Pro Glu Gly Phe Thr Gly Leu Tyr
                405                 410                 415

Cys Glu Ser Gln Met Gly Gln Gly Thr Arg Pro Ser Pro Thr Pro Val
            420                 425                 430

Thr Pro Arg Pro Pro Arg Ser Leu Thr Leu Gly Ile Glu Pro Val Ser
        435                 440                 445

Pro Thr Ser Leu Arg Val Gly Leu Gln Arg Tyr Leu Gln Gly Ser Ser
    450                 455                 460

Val Gln Leu Arg Ser Leu Arg Leu Thr Tyr Arg Asn Leu Ser Gly Pro
465                 470                 475                 480

Asp Lys Arg Leu Val Thr Leu Arg Leu Pro Ala Ser Leu Ala Glu Tyr
                485                 490                 495

Thr Val Thr Gln Leu
            500

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 11

His His His His His His
1               5
```

ANTI-TNF INDUCED APOPTOSIS (ATIA) DIAGNOSTIC MARKERS AND THERAPIES

RELATED APPLICATIONS

This application is a 35 U.S.C. § 371 U.S. national entry of International Application PCT/US2010/036394 (WO 2010/138709) having an International filing date of May 27, 2010, which claims priority to US Provisional Patent Application No. 61/182,072, filed on May 28, 2009. The entire contents of the aforementioned application are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

The term glioma refers to tumors that are derived from normal glial cells (i.e., astrocytes, oligodendrocytes, and ependymal cells). For each of these cell types, there is a malignant counterpart (e.g., astrocytoma is derived from astrocytes). Despite significant improvements in the early detection of malignant gliomas, the median survival of patients remains less than 12 months from the time of diagnosis. Malignant gliomas rarely metastasize outside the central nervous system, but they will diffusely invade the host brain. Astrocytic tumors comprise over 80% of primary CNS tumors and are classified by the type of cell they most closely resemble and according to their clinical and biological behavior (i.e., tumor grade). The slower growing lesions are commonly referred to as low-grade gliomas (LGGs), while the more clinically aggressive tumors are classified as high-grade gliomas (HGGs). HGGs are more common comprising nearly 80% of all gliomas.

Astrocytic tumors, the most common type of neuroepithelial tissue tumors (and are therefore sometimes loosely referred to by the term "glioma"), can be further subdivided based on the severity of the condition (i.e., WHO Grade 1 to 4, based on the severity of the condition, with 4 being the most serious form of glioma). Grade 1 corresponds to pilocytic astrocytoma; Grade 2 corresponds to diffuse astrocytoma; Grade 3 corresponds to anaplastic or malignant astrocytoma; and Grade 4 corresponds to glioblastoma multiforme, which is the most common glioma in adults and is considered the most serious form of astrocytic tumor.

Treatment of CNS tumors depends on the multiplicity, location, and grade of the tumor, and may include any of surgical resection, stereotactic radiosurgery (SRS), whole brain radiotherapy (WBRT) and chemotherapy or some combination thereof; however the inability of many conventional chemotherapeutic agents to cross the blood-brain barrier (BBB) has historically limited their use in the treatment of CNS tumors. Glial tumors, the most prevalent and morbid of which is astrcoytoma and its aggressive derivative glioblastoma multiforme, are the most common cancers of the adult central nervous system. They are also among the least treatable cancers, with a 5 year survival after initial diagnosis of <10% for tumors initially diagnosed at the grade 3 (anaplastic astrocytoma) or 4 (glioblastoma) stages. The currents treatment of glioma and glioblastoma are lacking, and achieve only palliation and short-term increments in survival. They include surgical resection—following which ultimate recurrence rates are over 90%—as well as radiation therapy, and chemotherapies that include cisplatin, BCNU and other mitotic inhibitors. The benefits of these current therapies are brief and temporary, and none are curative.

Accordingly, a need remains to for more effective compositions and methods for the detection and treatment of brain tumors.

SUMMARY OF THE INVENTION

The present inventors have found that ATIA is a hypoxia-inducible gene, and under hypoxia conditions ATIA protein expression is considerably increased, and deletion of ATIA renders cells sensitive to hypoxia induced apoptosis. The present inventors have shown in vitro and that ATIA protein localizes in the cell plasma membrane and the mitochondria and that ATIA mutant protein targeted to mitochondria is capable of protecting cells against TNF-induced apoptosis. In particular, the present inventors have shown that in glioblastoma, knocking down ATIA expression sensitizes the cells to hypoxia treatment, thus demonstrating that ATIA is important for cancer cell survival by providing protection from hypoxia-induced cell death.

Included in the present invention are diagnostic and therapeutic methods and compositions featuring ATIA. ATIA is useful as a diagnostic marker for cancer, in particular for glioblastoma. ATIA is also a therapeutic target in diseases such as cancer. The invention encompasses combination therapies where knockdown of ATIA is used in combination with other treatment. In one aspect, the invention features a method of diagnosing a subject as having, or having a propensity to develop a neoplasia, the method comprising determining the level of expression or biological activity of an anti-TNF Induced Apoptosis (ATIA) polypeptide in a subject sample wherein an alteration in the level of expression or biological activity relative to the expression or biological activity in a reference indicates that the subject has or has a propensity to develop a neoplasia.

In another aspect, the invention features a method of diagnosing a subject as having, or having a propensity to develop a neoplasia, the method comprising determining the level of expression or biological activity of an ATIA nucleic acid in a subject sample wherein an alteration in the level of expression relative to the expression in a reference indicates that the subject has or has a propensity to develop a neoplasia.

In one embodiment, the neoplasia is a solid tumor.

In one embodiment, the neoplasia is selected from the group consisting of brain, pancreatic, and stomach.

In another aspect, the invention features a method of diagnosing a subject as having, or having a propensity to develop a brain neoplasia, the method comprising determining the level of expression or biological activity of ATIA polypeptide in a subject sample wherein an alteration in the level of expression or biological activity relative to the expression or biological activity in a reference indicates that the subject has or has a propensity to develop a brain neoplasia.

In yet another aspect, the invention features a method of diagnosing a subject as having, or having a propensity to develop a brain neoplasia, the method comprising determining the level of expression or biological activity of an ATIA nucleic acid in a subject sample wherein an alteration in the level of expression relative to the expression in a reference indicates that the subject has or has a propensity to develop a brain neoplasia.

In a further aspect, the invention features a method of monitoring a subject diagnosed as having a brain neoplasia, the method comprising determining the level of expression or activity of an ATIA polypeptide in a subject sample, wherein an alteration in the level of expression or activity relative to the level of activity in a reference indicates the severity of the brain neoplasia in the subject.

In another aspect, the invention features a method of monitoring a subject diagnosed as having a brain neoplasia, the method comprising determining the expression of an ATIA nucleic acid molecule in a subject sample, wherein an alteration in the level of expression relative to the level of expression in a reference indicates the severity of the brain neoplasia in the subject.

In another aspect, the invention features a method of determining the progression of a brain neoplasia in a subject, the method comprising determining the expression or activity of an ATIA polypeptide in a subject sample, wherein an alteration in the level of expression or activity relative to the level of expression in a reference indicates the progression of the a brain neoplasia in the subject.

In a further aspect, the invention features a method of determining the progression of a brain neoplasia in a subject, the method comprising determining the expression of an ATIA nucleic acid molecule in a subject sample, wherein an alteration in the level of expression relative to the level of expression in a reference indicates the progression of the a brain neoplasia in the subject.

In one embodiment of the above aspects, the subject has, or has a propensity to develop a brain neoplasia.

In another embodiment of the above aspects, the method can be used to determine if a subject has a brain tumor. In a further embodiment, the tumor is a glioblastoma. In another further embodiment, the tumor is an astrocytoma.

In another aspect, the invention features a method of diagnosing a subject as having, or having a propensity to develop a glioblastoma, the method comprising determining the level of expression or biological activity of an ATIA polypeptide in a subject sample wherein an alteration in the level of expression or biological activity relative to the expression or biological activity in a reference indicates that the subject has or has a propensity to develop a glioblastoma.

In another further aspect, the invention features a method of diagnosing a subject as having, or having a propensity to develop a glioblastoma, the method comprising determining the level of expression or biological activity of an ATIA nucleic acid in a subject sample wherein an alteration in the level of expression relative to the expression in a reference indicates that the subject has or has a propensity to develop a glioblastoma.

In one embodiment of any one of the above aspects, the method is used to determine if a subject will be responsive to TRAIL therapy.

In another embodiment of any one of the above aspects, the method is used to determine if a subject will be responsive to chemotherapy.

In still another embodiment of any one the above aspects, the method is used to determine if a subject will be responsive to radiation treatment.

In another embodiment of any one of the above aspects, the ATIA nucleic acid comprises a sequence selected from the group consisting of: SEQ ID NO: 1, SEQ ID NO: 3, SEQ ID NO: 5, or fragments thereof.

In a further embodiment of any one of the above aspects, the ATIA polypeptide comprises a sequence selected from the group consisting of: SEQ ID NO: 2, SEQ ID NO: 4, SEQ ID NO: 6, or fragments thereof.

In one embodiment of any one of the above aspects, the level of expression is determined in an immunological assay. In a further embodiment, the immunological assay is an enzyme-linked immunosorbent assay (ELISA). In a related embodiment, the immunological assay is an immunohistochemical assay. In still another related embodiment, the ELISA is used to detect the extracellular portion of ATIA.

In another preferred embodiment, the extracellular portion comprises a sequence selected from the group consisting of SEQ ID NO: 7, 8, 9 or 10, or fragments thereof.

In one embodiment of any one of the above aspects, the expression of an ATIA nucleic acid molecule is detected using a hybridization reaction comprising hybridizing the sample to one or more primer sets. In one embodiment, the hybridization reaction is a polymerase chain reaction.

In a related embodiment, the each one or more primer set comprises a forward primer and a reverse primer, wherein the forward primer is complementary to a nucleic acid sequence corresponding to a nucleic acid sequence selected from SEQ ID NO: 1, SEQ ID NO: 3, SEQ ID NO: 5, SEQ ID NO: 7 and SEQ ID NO: 8, or fragments thereof, and the reverse primer is reverse complementary to a nucleic acid sequence corresponding to a nucleic acid sequence selected from SEQ ID NO: 1, SEQ ID NO: 3, or SEQ ID NO: 5, SEQ ID NO: 7 and SEQ ID NO: 8 or fragments thereof.

In another embodiment of any one of the above aspects, the subject is being treated for brain cancer.

In still another embodiment of any one of the above aspects, the alteration is an increase. In a related embodiment, the increase corresponds to an increased sensitivity to TRAIL-induced cell death.

In another embodiment of any one of the above aspects, the reference is a control subject sample. In another embodiment of any one of the above aspects, the reference is a subject sample obtained at an earlier time point. In another embodiment of any one of the above aspects, the subject sample is a biological sample.

In still another embodiment of any one of the above aspects, the method is used to diagnose a subject as having a brain tumor. In another embodiment of any one of the above aspects, the method is used to determine the treatment regimen for a subject having a brain tumor.

In yet another embodiment of any one of the above aspects, the method is used to determine the prognosis of a subject. In a related embodiment, a poor prognosis determines an aggressive treatment regimen for the subject.

In another embodiment of any one of the above aspects, the method further comprises obtaining a biological sample from the subject. In a related embodiment, the sample is a blood sample.

In another aspect, the invention features an ATIA antibody that specifically binds to an ATIA protein or fragment thereof.

In one embodiment, the ATIA protein or fragment thereof is selected from the group consisting of SEQ ID NO: 2, SEQ ID NO: 4, SEQ ID NO: 6, SEQ ID NO: 9 and SEQ ID NO: 10, or fragments thereof.

In another embodiment, the antibody binds to a an epitope corresponding to amino acids 600-673 of epitope of an ATIA polypeptide corresponding to SEQ ID NO: 2.

In another embodiment of any one of the above aspects, the antibody is monoclonal.

In another aspect, the invention features a polypeptide comprising an isolated ATIA protein, or fragment thereof, wherein the protein is upregulated in brain neoplasia.

In one embodiment, the ATIA protein is at least 85% identical to ATIA. In another embodiment, the ATIA protein comprises the extracellular domain. In another related embodiment, the extracellular domain comprises any one of SEQ ID NO: 7, 8, 9 or 10, a fragments thereof.

In another embodiment of any one of the above aspects, the polypeptide is linked to a detectable amino acid sequence or an affinity tag.

In another embodiment of any one of the above aspects, the ATIA nucleic acid comprises a sequence selected from the group consisting of: SEQ ID NO: 1 SEQ ID NO: 3, SEQ ID NO: 5, SEQ ID NO: 7 and SEQ ID NO: 8 or fragments thereof.

In another embodiment of any one of the above aspects, the ATIA polypeptide comprises a sequence selected from the group consisting of: SEQ ID NO: 2, SEQ ID NO: 4, SEQ ID NO: 6, SEQ ID NO: 9 and SEQ ID NO: 10 or fragments thereof.

In another aspect, the invention features an isolated ATIA nucleic acid molecule, wherein the nucleic acid molecule encodes a polypeptide of any one of the aspects described herein.

In another aspect, the invention features an isolated ATIA inhibitory nucleic acid molecule, wherein the inhibitory nucleic acid molecule specifically binds at least a fragment of a nucleic acid molecule encoding an ATIA protein.

In one embodiment, the invention features a vector comprising a nucleic acid molecule encoding the nucleic acid molecule of any one of the aspects as described herein.

In one embodiment of any one of the above aspects, the vector is an expression vector. In another embodiment of any one of the above aspects, the nucleic acid molecule is operably linked to a promoter.

In another embodiment, the invention features a host cell comprising a nucleic acid molecule of any one of the aspects as described herein. In one embodiment, the cell expresses an ATIA protein. In another embodiment, the cell is in vitro. In another embodiment, the cell is in vivo. In a further embodiment, the cell is a mammalian cell. In another further embodiment, the cell is a human cell.

In another aspect, the invention features a double-stranded RNA corresponding to at least a portion of an ATIA nucleic acid molecule that encodes an ATIA protein, wherein the double-stranded RNA is capable of altering the level of protein encoded by the ATIA nucleic acid molecule.

In one embodiment, the RNA is an siRNA.

In another aspect, the invention features an antisense nucleic acid molecule, wherein the antisense nucleic acid molecule is complementary to an ATIA nucleic acid molecule that encodes an ATIA protein, and wherein the antisense is capable of altering expression from the nucleic acid molecule to which it is complementary.

In still another aspect, the invention features an ATIA biomarker purified on a biochip.

In another aspect, the invention features a microarray comprising at least two nucleic acid molecules, or fragments thereof, fixed to a solid support, wherein at least one of the nucleic acid molecules is an ATIA nucleic acid molecule.

In still another aspect, the invention features a microarray comprising at least two polypeptides, or fragments thereof, bound to a solid support, wherein at least one of the polypeptides on the support is an ATIA polypeptide.

In one embodiment of the above aspects, the ATIA nucleic acid comprises a sequence selected from the group consisting of: SEQ ID NO: 1, SEQ ID NO: 3, SEQ ID NO: 5, SEQ ID NO: 7 and SEQ ID NO: 8 or fragments thereof.

In one embodiment of the above aspects, the ATIA polypeptide comprises a sequence selected from the group consisting of: SEQ ID NO: 2, SEQ ID NO: 4 SEQ ID NO: 6, SEQ ID NO: 9 and SEQ ID NO: 10 or fragments thereof.

In another aspect, the invention features a diagnostic kit for the diagnosis of a brain neoplasia in a subject comprising a primer set to detect an ATIA nucleic acid molecule, or fragment thereof, and written instructions for use of the kit for detection of a brain neoplasia.

In still another aspect, the invention features a diagnostic kit for the diagnosis of cancer in a subject comprising a primer set to detect an ATIA nucleic acid molecule, or fragment thereof, and written instructions for use of the kit for detection of cancer.

In still another aspect, the invention features a diagnostic kit for the diagnosis of a brain neoplasia in a subject comprising an antibody that specifically binds an ATIA polypeptide, or fragment thereof, and written instructions for use of the kit for detection of a brain neoplasia.

In one embodiment, the antibody binds to ATIA in a blood sample.

In another aspect, the invention features a kit for identifying a subject as having or having a propensity to develop a brain neoplasia, comprising an adsorbent, wherein the adsorbent retains an ATIA biomarker, and written instructions for use of the kit for detection of a brain neoplasia.

In one embodiment of the above aspects, the ATIA nucleic acid comprises a sequence selected from the group consisting of: SEQ ID NO: 1, SEQ ID NO: 3, and SEQ ID NO: 5, SEQ ID NO: 7 and SEQ ID NO: 8 or fragments thereof.

In one embodiment of the above aspects, the ATIA polypeptide comprises a sequence selected from the group consisting of: SEQ ID NO: 2, SEQ ID NO: 4, SEQ ID NO: 6, SEQ ID NO: 9 and SEQ ID NO: 10 or fragments thereof.

In another aspect, the invention features a method of altering the expression of an ATIA nucleic acid molecule in a cell, the method comprising contacting the cell with an effective amount of a compound capable of altering the expression of the ATIA nucleic acid molecule.

In one embodiment, the compound is an antisense nucleic acid molecule, a small interfering RNA (siRNA), or a double stranded RNA (dsRNA) that inhibits the expression of an ATIA nucleic acid molecule.

In another aspect, the invention features a method of altering ATIA protein expression in a cell, the method comprising contacting the cell with a compound capable of altering the expression of an ATIA polypeptide.

In one embodiment, the cell is a human cell. In another embodiment, the cell is a neoplastic cell.

In another aspect, the invention features a method of treating or preventing cancer, the method comprising administering to a subject in need thereof an effective amount of a small molecule that alters expression of an ATIA polypeptide.

In one embodiment, the small molecule is an inhibitory nucleic acid.

In another embodiment, the inhibitory nucleic acid is an siRNA.

In another further embodiment, the small molecule is a chemical inhibitor.

In a related embodiment, the chemical inhibitor is cyclohexamide.

In another particular aspect, the invention features a method of identifying a compound that inhibits cancer the method comprising contacting a cell that expresses an ATIA nucleic acid molecule with a candidate compound, and comparing the level of expression of the nucleic acid molecule in the cell contacted by the candidate compound with the level of expression in a control cell not contacted by the candidate compound, wherein an alteration in expression of the ATIA nucleic acid molecule identifies the candidate compound as a compound that inhibits cancer.

In another aspect, the invention features a method of treating or preventing a brain neoplasia, the method comprising administering to a subject in need thereof an effective amount of a pharmaceutical composition that alters expression of an ATIA polypeptide.

In another aspect, the invention features a method of identifying a compound that inhibits a brain neoplasia the method comprising contacting a cell that expresses an ATIA nucleic acid molecule with a candidate compound, and comparing the level of expression of the nucleic acid molecule in the cell contacted by the candidate compound with the level of expression in a control cell not contacted by the candidate compound, wherein an alteration in expression of the ATIA nucleic acid molecule identifies the candidate compound as a compound that inhibits a brain neoplasia.

In one embodiment of any one of the above aspects, the alteration in expression is a decrease in transcription.

In one embodiment of any one of the above aspects, the alteration in expression is a decrease in translation.

In one embodiment of any one of the above aspects, the method further comprises comprising treating the subject with a chemotherapeutic agent. In one embodiment of any one of the above aspects, the method further comprises treating the subject with radiation. In a related embodiment, the chemotherapeutic agent is an agent that can cross the blood-brain barrier. In a further related embodiment, the chemotherapeutic agent is selected from etoposide or cisplatin.

In another aspect, the invention features a kit for of treating or preventing a brain neoplasia, the kit comprising an effective amount of a pharmaceutical composition that alters expression of an ATIA polypeptide and instructions for use.

In another aspect, the invention features a kit for of treating or preventing a brain neoplasia, the kit comprising an effective amount of a pharmaceutical composition that alters expression of an ATIA nucleic acid and instructions for use.

In one embodiment of any one of the above aspect, the kit further comprises an additional chemotherapeutic agent.

In another aspect, the invention features a method of identifying a compound that inhibits cancer, the method comprising contacting a cell that expresses an ATIA polypeptide with a candidate compound, and comparing the level of expression of the polypeptide in the cell contacted by the candidate compound with the level of polypeptide expression in a control cell not contacted by the candidate compound, wherein an alteration in the expression of the ATIA polypeptide identifies the candidate compound as a compound that inhibits cancer.

In another aspect, the invention features a method of identifying a compound that inhibits cancer, the method comprising contacting a cell that expresses an ATIA polypeptide with a candidate compound, and comparing the biological activity of the polypeptide in the cell contacted by the candidate compound with the level of biological activity in a control cell not contacted by the candidate compound, wherein an alteration in the biological activity of the ATIA polypeptide identifies the candidate compound as a candidate compound that inhibits cancer.

In another aspect, the invention features a method of identifying a compound that inhibits a brain neoplasia, the method comprising contacting a cell that expresses an ATIA polypeptide with a candidate compound, and comparing the level of expression of the polypeptide in the cell contacted by the candidate compound with the level of polypeptide expression in a control cell not contacted by the candidate compound, wherein an alteration in the expression of the ATIA polypeptide identifies the candidate compound as a compound that inhibits a brain neoplasia.

In another aspect, the invention features a method of identifying a compound that inhibits a brain neoplasia, the method comprising contacting a cell that expresses an ATIA polypeptide with a candidate compound, and comparing the biological activity of the polypeptide in the cell contacted by the candidate compound with the level of biological activity in a control cell not contacted by the candidate compound, wherein an alteration in the biological activity of the ATIA polypeptide identifies the candidate compound as a candidate compound that inhibits a brain neoplasia.

In one embodiment of any one of the above methods, the brain neoplasia is a brain tumor. In a related embodiment, the tumor is a glioblastoma. In another related embodiment, the tumor is an astrocytoma.

In one embodiment of any one of the above methods, the cell is in vitro. In one embodiment of any one of the above methods, the cell is in vivo.

In one embodiment of any one of the above methods, the alteration in expression is assayed using an immunological assay, an enzymatic assay, or a radioimmunoassay.

In one embodiment of any one of the above methods, the ATIA nucleic acid comprises a sequence selected from the group consisting of: SEQ ID NO: 1, SEQ ID NO: 3, SEQ ID NO: 5, SEQ ID NO: 7 and SEQ ID NO: 8, or fragments thereof.

In one embodiment of any one of the above methods, the ATIA polypeptide comprises a sequence selected from the group consisting of: SEQ ID NO: 2, SEQ ID NO: 4 SEQ ID NO: 6, SEQ ID NO: 9 and SEQ ID NO: 10 or fragments thereof.

Other aspects of the invention are described in or are obvious from the following disclosure, and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 7 (A and B) show that ATIA inhibits TGFB signaling. (A) TNFb-induced Smad2phosphorylation is increased in ATIA−/− MEFs. (B) ATIA deletion has no effect on BMP4signaling.

FIG. 8 shows that two forms of ATIA protein are glycosylated differently.

FIG. 15 is a Table that shows the distribution of ATIA positive cases in the glioblastoma array.

FIG. 16 shows representative panels of immunohistochemical staining with anti vasorin (R and D as control) from the glioblastoma tissue array. Glioblastoma stage IV samples are shown in the panels on the right and adjacent normal brain tissues are shown in the panels on the left.

FIG. 19 shows glioblastoma cells that express ATIA are more sensitive to TRAIL-induced cell death. The left panel shows a western blot showing ATIA expression in A172, U87MG and 251 glioblastoma cells. The graph shows cell viability after the cells are treated with TRAIL for 24 hours.

FIG. 20 shows knocking down ATIA expression renders cells sensitive to etoposide or cisplatinum treatment. The top panel shows that siRNA knockdown reduces ATIA expression. The bottom panel is a graph where ATIA expression was partially knocked down and an MTT assay was used to determine cell proliferation.

In FIG. 23, $CoCl_2$ is a hypoxia mimic, which induced hypoxia in treated cells. ATIA protein expression particularly in the lower band (the mitochondrial ATIA), is considerably increased). ATIA promoter has two HIF responsive sites.

DETAILED DESCRIPTION OF THE INVENTION

I. Definitions

Figure 1A:
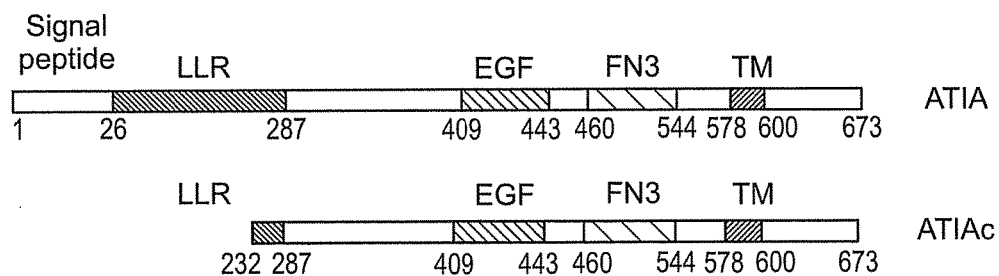
FIG. 1 (A-C) shows cloning of the ATIA gene. (A) The structural scheme of ATIA gene. (B) The expression levels of ATIA in different tissues. (C) ATIA expression in TRAF2−/− mouse embryonic fibroblasts (MEFs) examined by Northern blotting.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

By "antibody" is meant any immunoglobulin polypeptide, or fragment thereof, having immunogen binding ability.

By "ANTI-TNF Induced Apoptosis (ATIA)" is meant to refer to a type I membrane protein that binds TGF-beta. In preferred embodiments, mouse ATIA corresponds to the nucleic acid sequence set forth by NCBI reference No. NM_139307 (SEQ ID NO: 1) and the corresponding amino acid sequence set forth by NCBI reference No. NP_647468 (SEQ ID NO: 2). In other preferred embodiments, rat ATIA corresponds to the nucleic acid sequence set forth by NCBI reference No. NM_001109382 (SEQ ID NO: 3) and the corresponding amino acid sequence set forth by NCBI reference No. NP_001102852 (SEQ ID NO: 4).

By "vasorin" is meant to refer to a type I membrane protein that binds TGF-beta. In preferred embodiments, human vasorin corresponds to the nucleic acid sequence set forth by NCBI reference No. NM_138440 (SEQ ID NO: 5) and the corresponding amino acid sequence set forth by NCBI reference No. AA027704 (SEQ ID NO: 6).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

By "biomarker" is meant any protein or polynucleotide having an alteration in expression level or activity that is associated with a disease or disorder, for example cancer, for example glioblastoma.

By "detectable amino acid sequence" or "detectable moiety" is meant a composition that when linked with the nucleic acid or protein molecule of interest renders the latter detectable, via any means, including spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

A "labeled nucleic acid or oligonucleotide probe" is one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe may be detected by detecting the presence of the label bound to the nucleic acid or probe.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference. In some embodiments the portion retains at least 50%, 75%, or 80%, or more preferably 90%, 95%, or even 99% of the biological activity of the reference protein or nucleic acid described herein.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "inhibitory nucleic acid" is meant a double-stranded RNA, siRNA (short interfering RNA), shRNA (short hairpin RNA), or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

By "isolated nucleic acid molecule" is meant a nucleic acid (e.g., a DNA, RNA, or analog thereof) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

"Microarray" is meant to refer to a collection of nucleic acid molecules or polypeptides from one or more organisms arranged on a solid support (for example, a chip, plate, or bead).

By "neoplasia" as used herein is meant the abnormal proliferation of cells. In preferred embodiments, when the growth of a neoplasm exceeds, and is uncoordinated with, that of the normal tissues around it may cause a lump or tumor. A neoplasia may be benign, pre-malignant or malignant.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

"Complimentary nucleic acid sequences" refer to contiguous DNA or RNA sequences which have compatible nucleotides (e.g., A/T, G/C) in corresponding positions, such that base pairing between the sequences occurs. For example, the sense and anti-sense strands of a double-stranded DNA helix are known in the art to be complimentary.

By "protein" is meant any chain of amino acids, or analogs thereof, regardless of length or post-translational modification.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity. In certain preferred embodiments, the siRNA downregulates ATIA levels. In certain embodiments, ATIA siRNA are commercially prepared siRNA.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

Other definitions appear in context throughout the disclosure.

Methods of the Invention

The invention features diagnostics and therapeutic methods based on the discovery of ATIA as a diagnostic marker and as a potential therapeutic target for certain cancers, in particular brain cancers, such as human glioblastoma or astrocytoma.

The present invention is based, in part, on the finding that there is high expression of ATIA in certain types of cancers, in particular in brain cancers, for example human glioblastoma and astrocytoma. The present inventors have found that ATIA is a hypoxia-inducible gene, and that under hypoxia conditions ATIA protein expression is considerably increased, and deletion of ATIA renders cells sensitive to hypoxia-induced apoptosis.

Reported herein is the novel finding of a soluble form of ATIA that suggests that blood testing of ATIA level will provide an easy, quick and early diagnosis of disease.

Tumors that begin in brain tissue are known as primary brain tumors and are classified by the type of tissue in which they originate. The most common brain tumors are gliomas, which begin in the glial or supportive tissue. There are several types of gliomas. Astrocytomas are brain tumors that arise from small, star-shaped cells called astrocytes. They may grow anywhere in the brain or spinal cord. In adults, astrocytomas most often arise in the cerebrum. In children, they occur in the brain stem, the cerebrum and the cerebellum. A grade III astrocytoma is sometimes called anaplastic astrocytoma. A grade IV astrocytoma is usually called glioblastoma multiforme. Brain stem gliomas are brain tumors that occur in the lowest, stem-like part of the brain. The brain stem controls many vital functions. Most brain stem gliomas are high-grade astrocytomas. Ependymomas are brain tumors that usually develop in the lining of the ventricles. They may also occur in the spinal cord. Although these tumors can develop at any age, they are most common in childhood and adolescence. Oligodendrogliomasare tumors that occur in the cells that produce myelin, the fatty covering that protects nerves. These tumors usually arise in the cerebrum. They are rare, grow slowly and usually do not spread into surrounding brain tissue. They occur most often in middle-aged adults but have been found in people of all ages.

There are other types of brain tumors that do not begin in glial tissue. For example, medulloblastomas were once thought to develop from glial cells. However, recent research suggests that these tumors develop from primitive or developing nerve cells that normally do not remain in the body after birth. For this reason, medulloblastomas are sometimes called primitive neuroectodermal tumors (PNET). Most medulloblastomas arise in the cerebellum; however, they may occur in other areas as well. These tumors occur most often in children and are more common in boys than in girls. Meningiomas are tumors that grow from the meninges, or membranes that enclose the brain and spinal cord. They are usually benign. Because these tumors grow very slowly, the brain may be able to adjust to their presence. Meningiomas often grow quite large before they cause symptoms. They occur most often in women between 30 and 50 years of age. Schwannomas are benign and begin in Schwann cells, which produce the myelin that protects the acoustic nerve, or the nerve of hearing. They occur mainly in adults. These tumors affect women twice as often as men. Craniopharyngiomas are tumors that develop in the region of the pituitary gland near the hypothalamus. They are usually benign but are sometimes considered malignant because they can press on or damage the hypothalamus, a region of the brain, and affect vital functions. These tumors occur most often in children and adolescents. Germ cell tumors are tumors that arise from developing sex cells or germ cells. The most frequent type of germ cell tumor in the brain is the germinoma. Pineal region tumors are tumors that occur in or around the pineal gland, a tiny organ near the center of the brain. The tumor can be slow growing (pineocytoma), or fast growing (pineoblastoma). The pineal region is very difficult to reach, and these tumors often cannot be removed.

The symptoms of brain tumors depend on their size and location in the brain. Symptoms often are caused by damage to vital tissue and pressure on the brain as the tumor grows within the limited space in the skull. They may be caused by swelling and a buildup of fluid around the tumor, a condition called edema. Symptoms also may be due to hydrocephalus, which occurs when the tumor blocks the flow of cerebrospinal fluid and causes a build-up in the ventricles. If a brain tumor grows very slowly, its symptoms may not appear for some time.

The most frequent symptoms of brain tumors include headaches that tend to be worse in the morning and ease during the day, seizures or convulsions, nausea or vomiting, weakness or loss of feeling in the arms or legs, stumbling or lack of coordination in walking, abnormal eye movements or changes in vision, drowsiness, changes in personality or memory, changes in speech.

Anti TNF Induced Apoptosis (ATIA)

The Anti-TNF Induced Apoptosis (ATIA) gene was cloned through screening for proteins that protect cells against TNF-induced apoptosis. Four years before the cloning of ATIA, the human homolog of ATIA, vasorin, was reported as a TGF-beta binding protein.

In certain embodiments, mouse ATIA corresponds to the nucleotide sequence set forth by NCBI reference No. NM_139307, shown below as SEQ ID NO: 1, and the corresponding amino acid sequence set forth by NCBI reference No. NP_647468, shown below as SEQ ID NO: 2.

```
                                                                   SEQ ID NO: 1
   1 agagaccagc ctcttacgag tcaacttcga gtctggagcc ggagccagag accggggctg
  61 ggaaacccca gcccgggacg ggacgcagca gcctctggat cccgggaccc cggacctctc
 121 aggaccggcc agaggtgaag gactgaggcc ccactgaggc cttggaccgc accgcctggc
 181 tccttcagcc gcagtcgtct cctgggacag aagatgcact ccaggagctg cctgccacct
 241 ctcctgttgt tgcttctggt gctcctgggg tctggagtac agggttgccc atcaggctgc
 301 cagtgcaacc agccacagac agtcttctgc actgcccgtc agggaaccac agtgccccga
 361 gacgtgccac ctgacacagt gggcctgtac atctttgaga acggcatcac gacacttgat
 421 gtgggctgtt ttgctggcct tccgggcctg cagcttctgg acttgtcaca gaaccagatc
 481 actagcctgc ccgggggcat ctttcagcca cttgttaacc tcagtaacct ggacctgact
 541 gccaacaaac tgcacgagat ctccaacgag accttccgtg gcctgcggcg cctggagcgc
 601 ctctacctgg gcaagaaccg aattcgccac atccaaccgg gtgccttcga cgcgcttgat
 661 cgcctcctgg agctcaagct gccagacaat gagcttcggg tgttgccccc attgcacttg
 721 ccccgcctgc tgctgcttga cctcagccac aacagcatcc cagccctgga agccggaata
 781 ctggataccg ccaatgtaga ggcattgagg ttggctggcc tagggctgcg gcagctggat
 841 gaggggcttt ttggccgcct tctcaacctc catgacttgg atgtttctga caaccagttg
 901 gagcatatgc catctgtgat tcaaggcctg cgtggcctga cacgcctgcg gctggctggc
 961 aacacccgta ttgcccagat acggcccgag gacctcgctg gtctgactgc cctacaggaa
1021 ttggatgtga gcaacctaag cctgcaggcc ctgcccagtg acctctcgag tctctttccc
1081 cgcctgcgcc tcttagcagc tgccaggaac cccttcaact gcttgtgccc cttgagctgg
1141 tttggtcctt gggtgcgtga gaaccatgtt gtgttggcca gccctgagga gacgcgttgt
1201 cactttccac ccaagaatgc tggccgactg ctcctggatc tggattatgc agattttggc
1261 tgcccagtca ccactaccac ggccacagta cctactataa ggtctactat caggaaccc
1321 acactttcaa cttctagcca agctcccacc tggcccagcc tcacagagcc aactacccag
1381 gcctccaccg tactatcgac tgcccacca accatgaggc cagctcctca gcccaggac
1441 tgtccagcat ccatctgcct gaatggtggt agctgccgtt gggagcaag acaccactgg
1501 gagtgcctat gccctgaggg cttcattggc ctgtactgtg agagtccagt ggagcaaggg
1561 atgaagccca gctccatacc agacactcca aggcccctc cactgctgcc tctcagcatt
1621 gagccggtga gcccacctc cttgcgtgtg aagctgcagc gctacttgca gggtaacact
1681 gtgcagctac ggagcctccg gctcacctat cgcaacctgt ctggccctga caaacgactg
1741 gtgacattac ggctgcctgc ttcacttgca gagtatacag tcacccagct gcgacccaat
1801 gccacctatt ctatctgtgt cacaccttg ggagctggac ggacacctga aggtgaggag
1861 gcctgtgggg aggcaaacac ttcccaggca gtccgctcta accatgcccc agttacccag
1921 gcccgtgagg gcaacctgcc actcctcatt gcgcctgccc tggctgctgt acttctggct
1981 gtgttagccg ctgcagggc agcctactgt gtgcggcggg cacgggcaac ttctacagct
2041 caggacaaag ggcaggtggg gccagggact ggacccctgg aactagggg ggtgaaagcc
2101 cctttggagc caggctccaa ggcaacagag ggaggtgggg aggctttgtc aggtggtcct
2161 gaatgtgagg tgcctcttat gggctaccca gggcccagcc ttcaggggt cctccctgct
2221 aagcactaca tttagactgg tgagaaagag cagccagggg gtcaggcttt cagtcaccac
2281 cctcctgctg ccacagaagg aagttctcag tatacaccac agtgcacgtg catgatggag
2341 ctgtgggacc ctctctgggc tgggtctcat ctgtaagctg ctacagccca gatgaactct
2401 gccagccgcc agtgcatcca gtacagcgcc tgccatcttg tcaatgtgc aaccctggga
2461 tgtgagccct gccatgtgct ggtaacatgg ctaggcatgt tgggcttccc aaaccatgga
2521 gtctggtaac cagtgaagga agcccccaga aataatgagt ggggaaggta ctagggcact
2581 ggccttggcc tcaaaagtgc aggcacactt gaaactgaa aggaaggtgc tctgggcaca
2641 tgtggatttg cttctattgt tttgttttgt ttttctaat gtatttataa aagatctttt
2701 cccatttatg ctgggaaagt gttttcaaa ctcagtgaca aggactttgg tttttgtaag
2761 actgttgatg atatgaaggc cttttgtaag aaaataaaa ataaagtaaa ttgcctgtct
2821 ctctggttgg gcttgagatt taaggtctgt ggacatgcac aggattggag ggctgctgcc
2881 ctgccattag aatgctctag ccatgggtcc tgacccatgg taaggcttgc acttgggtgg
2941 ggccggaaaa tggacttgtt aggtagctta ccctaggcta ggcctcctct tctgccagca
3001 ggaaccacag tgcttaatgt ataaggcaga aaggggctca tagaaaacac agaacacaaa
3061 gggaggtcac atccctcctt gggtgttctg aaagtgcagt ccactatctt caactagaga
3121 agacagcctg gagcttcctc attctagagc ctaacagctg atcctgggac caggtggctt
3181 ccagactgg
```

```
                                                                   SEQ ID NO: 2
  1 mhsrsclppl lllllvllgs gvqgcpsgcq cnqpqtvfct arqgttvprd vppdtvglyi
 61 fengittldv gcfaglpglq lldlsqnqit slpggifqpl vnlsnldlta nklheisnet
121 frglrrlerl ylgknrirhi qpgafdaldr llelklpdne lrvlpplhlp rlllldlshn
181 sipaleagil dtanvealrl aglglrqlde glfgrllnlh dldvsdnqle hmpsviqglr
241 gltrlrlagn triaqirped lagltalqel dvsnlslqal psdlsslfpr lrllaaarnp
301 fnclcplswf gpwvrenhvv laspeetrch fppknagrll ldldyadfgc pvttttatvp
361 tirstirept lstssqaptw psltepttqa stvlstappt mrpapqpqdc pasiclnggs
421 crlgarhhwe clcpegfigl ycespveqgm kpssipdtpr pppllplsie pvsptslrvk
```

```
481 lqrylqgntv qlrslrltyr nlsgpdkrlv tlrlpaslae ytvtqlrpna tysicvtplg
541 agrtpegeea cgeantsqav rsnhapvtqa regnlpllia palaavllav laaagaaycv
601 rraratstaq dkgqvgpgtg plelegvkap lepgskateg ggealsggpe cevplmgypg
661 pslqgvlpak hyi
```

In other embodiments, rat ATIA corresponds to the nucleotide sequence set forth by NCBI reference No. NM_001109382, shown below as SEQ ID NO: 3, and the corresponding amino acid sequence set forth by NCBI reference No. NP_001102852, shown below as SEQ ID NO: 4.

```
                                                              SEQ ID NO: 3
   1 ggagcccggg gttgggagac ccggacgcag tagcctccgg atcccgggac cccggacctt
  61 tcaggaccgg ccggaggcga aggactgagg ccccattgag gccttgggcc gcaccgcccc
 121 gctccctcag ccacagtcgt ctcccgggac agaagatgca ctccaggagc tgcctgccac
 181 ctcttctgtt gttgctcctg gtgctcctgg gtctggagt acagagctgc ccatcaggct
 241 gccagtgcaa ccaaccacag acagtcttct gcactgcccg tcagggaacc acggtgcccc
 301 gagacgtgcc gcctgacaca gtgggcctgt acatctttga aacggcatc actacacttg
 361 atgtaggctg ttttgctggc ttcccaggcc tgcagcttct ggacttgtca cagaaccaga
 421 tcactagcct gcccggtggc atctttcagc cacttgtgaa cctcagtaac ctggacctga
 481 ctgctaacaa actgcacgag atctccaacg agaccttccg tggcctgcgg cgcctcgaac
 541 gcctctacct gggcaagaac cgcattcgcc acatccagcc tggtgccttc gatgcacttg
 601 accacctcct ggagctcaag ctgccagaca atgagcttcg ggtgctgccc ccactgcact
 661 tgcctcgcct gctgctgctt gacctcagcc acaacagtat cccagccctg gaagctggaa
 721 tactggatac tgccaatgtg gaggcactgc ggctggctgg cctcgggctg cggcagctgg
 781 atgaggggct ttttggccgc cttcgcaacc tccatgacct ggatgtttct gacaaccagt
 841 tggggcacat gccctccgtg attcaaggcc tgcgtggcct gacacgcctg cggctggctg
 901 gcaacacccg gattgcccag atccggcccg aggacctcgc tggcctgact gccctacagg
 961 aactggatgt gagcaacctg agcctgcagg ccctgcccag tgacctctcc agtctctttc
1021 cccgcctgcg cctcctagca gctgcccgaa accccttaa ctgcttatgc cccttgagct
1081 ggtttggtcc ttgggttcgt gagagccatg ttgtgctggc cagccctgag gagacacgtt
1141 gtcacttccc acccaagaac gccggccgac tgctcctgga gctggattat gcagattttg
1201 gctgcccagt caccactacc acagccacag ttcctactat aaggcctact gtcagggagc
1261 ccacaccttc aacttccagc caagctccca cctggcccag cccacagag ccaactaccc
1321 aggcccccat cgtactgtcc actgccccac caaccatgag gccggctcct cagccccagg
1381 actgtccagc atccatctgc ctgaatggtg gtagctgccg tgtaggggca aaacaccacc
1441 tggagtgcct gtgccccgag ggcttcattg gcctgtactg tgagagtccc gtggaacaaa
1501 ggacaaagcc cagctccata ccggacaccc cacggccccc gcggctgctg cctctgcgca
1561 ttgagccggt gagccccacc tccctgcgtg tggagctgca gcgctacctg cagggcaaca
1621 ccgtgcagtc gcggagcctc cggctcacct accgcaacct gtctggccct gacaagcggc
1681 tggtgacgct gcggctgcct gcttcacttg cagagtacac agtcacccag ctgcggccca
1741 atgccaccta ttctatctgt gtcacagccc tgggagctgg gcggacacct gaaggtgagg
1801 aggcctgtgg ggaggccaac actccccagg ccgtccgctc caaccatgcc ccagtcaccc
1861 aggcccggga gggcaacctg ccactcctca ttgcaccgc cctggctgct gtgcttctgg
1921 ctgtgttggc tgcctcgggg gcagtctact gtgtgcgacg ggcgcgggca agttccacag
1981 ctcaggacaa agggcaggtg ggaccaggga ccgggccct ggaactagag ggggtgaaag
2041 tccccttgga gccaggctcc aaggcatcag agggaggcgg ggaggcccta tcaggtggtc
2101 ctgaatgtga ggtgcccctc atgggctacc cagggcccag tcttcagggg gtcctccctg
2161 ctcagcccta catttaagca cgtgagaagg agcagccagg aggctgggct ttcagtctcc
2221 accctcctgc tgctacagaa ggaagttctc aatgcgcacc acagtgcaca tgtgtgaccg
2281 gtgctgtggg acagcagcca gtccccgacc ctctctgggc tgggtcatct gaaagctgct
2341 acagcccaaa tgaactccca gcaccagcat ccagtacaga gcctgctgcc ttgcgcagtc
2401 tgcagtcctg ggacgggaac cctgccatgt gctggtagca tggctaggat gttgggcttc
2461 ccgggccctg gggtctggta accagtgaag gaagccccca aaaatagtgg gtagggaagg
2521 cactagggcc gtggccgtgg ccccgaaagt gcaggaacac ttgaaactgg aaaggaaggt
2581 gctctgggca cacgtggatt tgcttctatt gttttgtttt tctcctaatg tatttataaa
2641 agatctttc ccgtttatgc tgggaaaaag tgtttttcaa actcagtgac aaggactttt
2701 ggttttgta agactattga tgatatgaag gccttttgt
```

```
                                                              SEQ ID NO: 4
   1 mhsrsclppl llllvllgs gvqscpsgcq cnqpqtvfct arqgttvprd vppdtvglyi
  61 fengittldv gcfagfpglq lldlsqnqit slpggifqpl vnlsnldlta nklheisnet
 121 frglrrlerl ylgknrirhi qpgafdaldh llelklpdne lrvlpplhlp rllldlshn
 181 sipaleagil dtanvealrl aglglrqlde glfgrlrnlh dldvsdnqlg hmpsviqglr
 241 gltrlrlagn triaqirped lagltalqel dvsnlslqal psdlsslfpr lrllaaarnp
 301 fnclcplswf gpwvreshvv laspeetrch fppknagrll leldyadfgc pvttttatvp
 361 tirptvrept pstssqaptw pspteptqa pivlstappt mrpapqpqdc pasiclnggs
 421 crvgakhhle clcpegfigl ycespveqrt kpssipdtpr pprllplrie pvsptslrve
 481 lqrylqgntv qlrslrltyr nlsgpdkrlv tlrlpaslae ytvtqlrpna tysicvtalg
 541 agrtpegeea cgeantpqav rsnhapvtqa regnlpllia palaavllav laasgavycv
 601 rrarasstaq dkgqvgpgtg plelegvkvp lepgskaseg ggealsggpe cevplmgypg
 661 pslqgvlpaq pyi
```

Vasorin is a typical type I membrane protein, containing tandem arrays of a characteristic leucine-rich repeat motif, an epidermal growth factor-like motif, and a fibronectin type III-like motif at the extracellular domain. Expression analyses demonstrated that vasorin is predominantly expressed in vascular smooth muscle cells, and that its expression is developmentally regulated. The vasorin gene is conserved in chimpanzee, cow, mouse, rat, and zebrafish.

In certain embodiments, human vasorin corresponds to the nucleotide sequence set forth by NCBI reference No. NM_138440, shown below as SEQ ID NO: 5, and the corresponding amino acid sequence set forth by NCBI reference No. AA027704, shown below as SEQ ID NO: 6.

```
                                                                SEQ ID NO: 5
   1 gactccggag cccgagcccg gggcgggtgg acgcggactc gaacgcagtt gcttcgggac
  61 ccaggacccc ctcgggccg acccgccagg aaagactgag gccgcggcct gccccgcccg
 121 gctccctgcg ccgccgccgc ctcccggac agaagatgtg ctccagggtc cctctgctgc
 181 tgccgctgct cctgctactg gccctggggc ctggggtgca gggctgccca tccggctgcc
 241 agtgcagcca gccacagaca gtcttctgca ctgcccgcca ggggaccacg gtgccccgag
 301 acgtgccacc cgacacggtg gggctgtacg tctttgagaa cggcatcacc atgctcgacg
 361 caggcagctt tgccggcctg ccgggcctgc agctcctgga cctgtcacag aaccagatcg
 421 ccagcctgcc cagcggggtc ttccagccac tcgccaacct cagcaacctg gacctgacag
 481 ccaacaggct gcatgaaatc accaatgaga ccttccgtgg cctgcggcgc ctcgagcgcc
 541 tctacctggg caagaaccgc atccgccaca tccagcctgg tgccttcgac acgtctgacc
 601 gcctcctgga gctcaagctg caggacaacg agctgcgggc actgcccccg ctgcgcctgc
 661 cccgcctgct gctgctggac ctcagccaca acagcctcct ggccctggag cccggcatcc
 721 tggacactgc caacgtggag gcgctgcggc tggctggtct ggggctgcag cagctggacg
 781 aggggctctt cagccgcttg cgcaacctcc acgacctgga tgtgtccgac aaccagctgg
 841 agcgagtgcc acctgtgatc cgaggcctcc ggggcctgac gcgcctgcgg ctggccggca
 901 acacccgcat tgcccagctg cggcccgagg acctggccgg cctggctgcc ctgcaggagc
 961 tggatgtgag caacctaagc ctgcaggccc tgcctggcga cctctcgggc ctcttccccc
1021 gcctgcggct gctggcagct gcccgcaacc ccttcaactg cgtgtgcccc ctgagctggt
1081 ttggcccctg ggtgcgcgag agccacgtca cactggccag ccctgaggag acgcgctgcc
1141 acttcccgcc caagaacgct ggccggctgc tcctggagct tgactacgcc gactttggct
1201 gcccagccac caccaccaca gccacagtgc ccaccacgag gccgtggtg cgggagccca
1261 cagccttgtc ttctagcttg gctcctacct ggcttagccc cacagagccg gccactgagg
1321 cccccagcc gccctccact gccccaccga ctgtagggcc tgtcccccag ccccaggact
1381 gcccaccgtc cacctgcctc aatggggggca catgccacct gggggacacgg caccacctgg
1441 cgtgcttgtg ccccgaaggc ttcacggggcc tgtactgtga gagccagatg gggcagggga
1501 cacggcccag ccctacacca gtcacgccga ggccaccacg gtccctgacc ctgggcatcg
1561 agccggtgag ccccacctcc ctgcgcgtgg gctgcagcg ctacctccag gggagctccg
1621 tgcagctcag gagcctccgt ctcacctatc gcaacctatc gggccctgat aagcggctgg
1681 tgacgctgcg actgcctgcc tcgctcgctg agtacacggt caccccagctg cggcccaacg
1741 ccacttactc cgtctgtgtc atgccttttgg ggcccgggcg ggtgccggag ggcgaggagg
1801 cctgcgggga ggcccataca ccccccagccg tccactccaa ccacgcccca gtcacccagg
1861 cccgcgaggg caacctgccg ctcctcattg cgcccgccct ggccgcggtg ctcctggccg
1921 cgctggctgc ggtgggggca gcctactgtg tgcggcgggg gcgggccatg gcagcagcgg
1981 ctcaggacaa agggcaggtg gggccagggg ctgggcccct ggaactggag ggagtgaagg
2041 tccccttgga gccaggcccg aagcaacag agggcggtgg agaggccctg cccagcgggt
2101 ctgagtgtga ggtgccactc atgggcttcc cagggcctgg cctccagtca ccctccacg
2161 caaagcccta catctaagcc agagagagac agggcagctg gggccgggct ctcagccagt
2221 gagatggcca gcccctcct gctgccacac cacgtaagtt ctcagtccca acctcgggga
2281 tgtgtgcaga cagggctgtg tgaccacagc tgggccctgt tccctctgga cctcggtctc
2341 ctcatctgtg agatgctgtg gcccagctga cgagccctaa cgtccccaga accgagtgcc
2401 tatgaggaca gtgtccgccc tgcctccgc aacgtgcagt ccctgggcac ggcgggccct
2461 gccatgtgct ggtaacgcat gcctgggccc tgctgggctc tccactcca ggcggaccct
2521 gggggccagt gaaggaagct cccggaaaga gcagaggag agcgggtagg cggctgtgtg
2581 actctagtct tggccccagg aagcgaagga acaaaagaaa ctggaaagga agatgcttta
2641 ggaacatgtt ttgcttttt aaaatatata tatatttata agagatcctt tcccatttat
2701 tctgggaaga tgttttcaa actcagagac aaggactttg gtttttgtaa gacaaacgat
2761 gatatgaagg cctttttgtaa gaaaaaataa aagatgaagt gtgtttaaaa aaaaaaaaa
2821 aaaaaaaaa aaaaaaaaa aaaaaaaaa aaaaaaaaa aaaa
```

```
                                                                SEQ ID NO: 6
   1 mcsrvplllp lllllalgpg vqgcpsgcqc sqpqtvfcta rqgttvprdv ppdtvglyvf
  61 engitmldag sfaglpglql ldlsqnqias lpsgvfqpla nlsnldltan rlheitnetf
 121 rglrrlerly lgknrirhiq pgafdtldrl lelklqdnel ralpplrlpr lllldlshns
 181 llalepgild tanvealrla glglqqldeg lfsrlrnlhd ldvsdnqler vppvirglrg
 241 ltrlrlagnt riaqlrpedl aglaalqeld vsnlslqalp gdlsglfprl rllaaarnpf
 301 ncvcplswfg pwvreshvtl aspeetrchf ppknagrlll eldyadfgcp attttatvpt
 361 trpvvrepta lsssslaptwl sptepateap sppstapptv gpvpqpqdcp pstclnggtc
 421 hlgtrhhlac lcpegftgly cesqmgqgtr psptpvtprp prsltlgiep vsptslrvgl
 481 qrylqgssvq lrslrltyrn lsgpdkrlvt lrlpaslaey tvtqlrpnat ysvcvmplgp
 541 grvpegeeac geahtppavh snhapvtqar egnlplliap alaavllaal aavgaaycvr
 601 rgramaaaaq dkgqvgpgag plelegvkvp lepgpkateg ggealpsgse cevplmgfpg
 661 pglqsplhak pyi
```

Various conserved regions have been identified in ATIA/vasorin, including putative signal peptide, leucine rich repeats (LRRs), EGF motif, fibronectin type III motif, transmembrane sequence, and at least five putative N-glycosylation sites.

The extracellular domain of ATIA corresponds to amino acids 600-673 of the full length sequence.

In certain embodiments, ATIA is in a soluble form.

The soluble form of mouse ATIA corresponds to residues 289 to 1792 of SEQ ID NO: 1, and is represented by SEQ ID NO: 7, or fragments thereof, shown below:

```
                                                              SEQ ID NO: 7
        tcaggctgcc agtgcaacc  agccacagac agtcttctgc actgcccgtc agggaaccac agtgccccga
        gacgtgccac ctgacacagt gggcctgtac atctttgaga acggcatcac gacacttgat gtgggctgtt
        ttgctggcct tccgggcctg cagcttctgg acttgtcaca gaaccagatc actagcctgc ccgggggcat
        ctttcagcca cttgttaacc tcagtaacct ggacctgact gccaacaaac tgcacgagat ctccaacgag
        accttccgtg gcctgcggcg cctggagcgc tctacctgg  gcaagaaccg aattcgccac atccaaccgg
        gtgccttcga cgcgcttgat cgcctcctgg agctcaagct gccagacaat gagcttcggg tgttgccccc
        attgcacttg ccccgcctgc tgctgcttga cctcagccac aacagcatcc cagccctgga agccggaata
        ctggataccg ccaatgtaga ggcattgagg ttggctgcc  tagggctgcg gcagctggat gaggggcttt
        ttggccgcct tctcaacctc catgacttgg atgtttctga caaccagttg gagcatatgc catctgtgat tcaaggcctg
        cgtggcctga cacgcctgcg gctggctggc aacacccgta ttgcccagat acggcccgag gacctcgctg
        gtctgactgc cctacaggaa ttggatgtga gcaacctaag cctgcaggcc ctgcccagtg acctctcgag
        tctctttccc cgcctgcgcc tcttagcagc tgccaggaac cccttcaact gcttgtgccc cttgagctgg tttggtcctt
        gggtgcgtga gaaccatgtt gtgttggcca gccctgagga gacgcgttgt cactttccac ccaagaatgc
        tggccgactg ctcctggatc tggattatgc agattttggc tgcccagtca ccactaccac ggccacagta
        cctactataa ggtctactat cagggaaccc acactttcaa cttctagcca agctcccacc tggcccagcc
        tcacagagcc aactacccag gcctccaccg tactatcgac tgccccacca accatgaggc cagctcctca
        gccccaggac tgtccagcat ccatctgcct gaatggtggt agctgccgtt tgggagcaag acaccactgg
        gagtgcctat gccctgaggg cttcattggc ctgtactgtg agagtccagt ggagcaaggg atgaagccca
        gctccatacc agacactcca aggcccctc  cactgctgcc tctcagcatt gagccggtga gccccacctc
        cttgcgtgtg aagctgcagc gctacttgca gggtaacact gtgcagctac ggagcctccg gctcacctat
        cgcaacctgt ctggccctga caaacgactg gtgacattac ggctgcctgc ttcacttgca gagtatacag
        tcacccagct
        gc
```

The soluble form of human vasorin corresponds to residues 231 to 1731 of SEQ ID NO: 5, and is represented by SEQ ID NO: 8, or fragments thereof, shown below:

```
                                                              SEQ ID NO: 8
        tccggctgcc agtgcagcca gccacagaca gtcttctgca ctgcccgcca ggggaccacg gtgccccgag
        acgtgccacc cgacacggtg gggctgtacg tctttgagaa cggcatcacc atgctcgacg caggcagctt
        tgccggcctg ccgggcctgc agctcctgga cctgtcacag aaccagatcg ccagcctgcc cagcggggtc
        ttccagccac tcgccaacct cagcaacctg gacctgacag ccaacaggct gcatgaaatc accaatgaga
        ccttccgtgg cctgcggcgc ctcgagcgcc tctacctggg caagaaccgc atccgccaca tccagcctgg
        tgccttcgac acgctcgacc gcctcctgga gctcaagctg caggacaacg agctgcgggc actgcccccg
        ctgcgcctgc cccgcctgct gctgctggac ctcagccaca acagcctcct ggccctggag cccggcatcc
        tggacactgc caacgtggag gcgctgcggc tggctggtct ggggctgcag cagctggacg aggggctctt
        cagccgcttg cgcaacctcc acgacctgga tgtgtccgac aaccagctgg agcgagtgcc acctgtgatc
```

-continued

```
cgaggcctcc ggggcctgac gcgcctgcgg ctggccggca acacccgcat tgcccagctg cggcccgagg acctggccgg cctggctgcc ctgcaggagc tggatgtgag caacctaagc ctgcaggccc tgcctggcga cctctcgggc ctcttccccc gcctgcggct gctggcagct gcccgcaacc ccttcaactg cgtgtgcccc ctgagctggt ttggcccctg ggtgcgcgag agccacgtca cactggccag ccctgaggag acgcgctgcc acttcccgcc caagaacgct ggccggctgc tcctggagct tgactacgcc gactttggct gcccagccac caccaccaca gccacagtgc ccaccacgag gcccgtggtg cgggagccca cagccttgtc ttctagcttg gctcctacct ggcttagccc cacagagccg gccactgagg cccccagccc gccctccact gccccaccga ctgtagggcc tgtcccccag ccccaggact gccccaccgtc cacctgcctc aatgggggca catgccacct ggggacacgg caccacctgg cgtgcttgtg ccccgaaggc ttcacgggcc tgtactgtga gagccagatg gggcagggga cacggcccag ccctacacca gtcacgccga ggccaccacg gtccctgacc ctgggcatcg agccggtgag ccccacctcc ctgcgcgtgg ggctgcagcg ctacctccag gggagctccg tgcagctcag gagcctccgt ctcacctatc gcaacctatc gggccctgat aagcggctgg tgacgctgcg actgcctgcc tcgctcgctg agtacacggt cacccagctg c
```

In other embodiments, the amino acid sequence of soluble mouse ATIA corresponds to residues 26 to 526 of SEQ ID NO: 2, and is represented by SEQ ID NO: 9, or fragments thereof, shown below:

```
                                       SEQ ID NO: 9
PSGCQCNQPQTVFCTARQGTTVPRDVPPDTVGLYIFENGITTLDV

GCFAGLPGLQLLDLSQNQITSLPGGIFQPLVNLSNLDLTANKLHE

ISNETFRGLRRLERLYLGKNRIRHIQPGAFDALDRLLELKLPDNE

LRVLPPLHLPRLLLLDLSHNSIPALEAGILDTANVEALRLAGLGL

RQLDEGLFGRLLNLHDLDVSDNQLEHMPSVIQGLRGLTRLRLAGN

TRIAQIRPEDLAGLTALQELDVSNLSLQALPSDLSSLFPRLRLLA

AARNPFNCLCPLSWFGPWVRENHVVLASPEETRCHFPPKNAGRLL

LDLDYADFGCPVTTTTATVPTIRSTIREPTLSTSSQAPTWPSLTE

PTTQASTVLSTAPPTMRPAPQPQDCPASICLNGGSCRLGARHHWE

CLCPEGFIGLYCESPVEQGMKPSSIPDTPRPPPLLPLSIEPVSPT

SLRVKLQRYLQGNTVQLRSLRLTYRNLSGPDKRLVTLRLPASLAE

YTVTQL
```

In other embodiments, the amino acid sequence of human soluble vasorin corresponds to residues 25 to 525 of SEQ ID NO: 6, and is represented by SEQ ID NO: 10, or fragments thereof, shown below:

```
                                      SEQ ID NO: 10
PSGCQCSQPQTVFCTARQGTTVPRDVPPDTVGLYVFENGITMLDA

GSFAGLPGLQLLDLSQNQIASLPSGVFQPLANLSNLDLTANRLHE

ITNETFRGLRRLERLYLGKNRIRHIQPGAFDTLDRLLELKLQDNE

LRALPPLRLPRLLLLDLSHNSLLALEPGILDTANVEALRLAGLGL

QQLDEGLFSRLRNLHDLDVSDNQLERVPPVIRGLRGLTRLRLAGN
```
-continued
```
TRIAQLRPEDLAGLAALQELDVSNLSLQALPGDLSGLFPRLRLLA

AARNPFNCVCPLSWFGPWVRESHVTLASPEETRCHFPPKNAGRLL

LELDYADFGCPATTTTATVPTTRPVVREPTALSSSLAPTWLSPTE

PATEAPSPPSTAPPTVGPVPQPQDCPPSTCLNGGTCHLGTRHHLA

CLCPEGFTGLYCESQMGQGTRPSPTPVTPRPPRSLTLGIEPVSPT

SLRVGLQRYLQGSSVQLRSLRLTYRNLSGPDKRLVTLRLPASLAE

YTVTQL
```

Methods of the Invention

The present inventors have found that ATIA is a hypoxia inducible gene, and that under hypoxia conditions ATIA is considerably increased. Human cancers are characterized by intratumoral hypoxia, a significant reduction in oxygen availability. Physiological responses triggered by hypoxia impact many aspects of cancer progression, including immortalization, transformation, differentiation, genetic instability, angiogenesis, metabolic adaptation, autocrine growth factor signaling, invasion, metastasis, and resistance to therapy.

In embodiments of the invention, a patient having cancer will show an increase in the expression of ATIA nucleic acid molecule. In particular embodiments, the patient may suffer from a solid tumor that expresses elevated levels of ATIA. In further particular embodiments, the patient may suffer from glioblastoma or astrocytoma. Alterations in gene expression are detected using methods known to the skilled artisan and described herein. Such information can be used to diagnose cancer, and in particular glioblastoma or astrocytoma. In another embodiment, an alteration in the expression of ATIA nucleic acid molecule is detected using polymerase chain reaction (PCR), for example, real time PCR or semi quantitative real time PCR to detect changes in gene expression.

Primers used for amplification of ATIA nucleic acid molecule, including but not limited to those primer sequences described herein, are useful in diagnostic methods of the invention. The primers of the invention embrace oligonucleotides of sufficient length and appropriate sequence so as to provide specific initiation of polymerization on a significant number of nucleic acids. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a locus strand. The primer must be sufficiently long to prime the synthesis of extension products in the presence of the inducing agent for polymerization. The exact length of primer will depend on many factors, including temperature, buffer, and nucleotide composition. Primers of the invention are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus. While exemplary primers are provided herein, it is understood that any primer that hybridizes with the target sequences of the invention are useful in the method of the invention for detecting ATIA nucleic acid molecules.

In one embodiment, ATIA-specific primers amplify a desired genomic target using the polymerase chain reaction (PCR), for example quantitative PCR or semi quantitative RT-PCR. The amplified product is then detected using standard methods known in the art. In one embodiment, a PCR product (i.e., amplicon) or real-time PCR product is detected by probe binding. In one embodiment, probe binding generates a fluorescent signal, for example, by coupling a fluorogenic dye molecule and a quencher moiety to the same or different oligonucleotide substrates (e.g., TaqMan® (Applied Biosystems, Foster City, Calif., USA), Molecular Beacons (see, for example, Tyagi et al., Nature Biotechnology 14(3):303-8, 1996), Scorpions® (Molecular Probes Inc., Eugene, Oreg., USA)). In another example, a PCR product is detected by the binding of a fluorogenic dye that emits a fluorescent signal upon binding (e.g., SYBR Green (Molecular Probes)). Such detection methods are useful for the detection of ATIA PCR product.

In another embodiment, hybridization with PCR probes that are capable of detecting an ATIA nucleic acid molecule, including genomic sequences, or closely related molecules, may be used to hybridize to a nucleic acid sequence derived from a patient having a cancer, and in particular glioblastoma or astrocytoma; however any other cancer types that express elevated levels of ATIA are envisioned as well. The specificity of the probe determines whether the probe hybridizes to a naturally occurring sequence, allelic variants, or other related sequences. Hybridization techniques may be used to identify mutations indicative of a cancer, e.g. glioblastoma, or may be used to monitor expression levels of these genes (for example, by Northern analysis (Ausubel et al., supra).

Diagnostics and Prognostics

The present invention provides a number of diagnostic assays that are useful for the identification, in particular the early identification, or characterization of cancer, for example glioblastoma or astrocytoma. In particular embodiments, the invention provides methods for detecting ATIA levels in biological fluids, for example using an ELISA-based assay. This ELISA based blood test of ATIA level will provide an easy and early diagnosis of the disease, which normally needs surgery to spot.

The invention also features methods of determining if a subject will respond to tumour necrosis factor-related apoptosis-inducing ligand (TRAIL) therapy. The method is based, in part, on the finding that certain cells that express ATIA are more sensitive to TRAIL-induced cell death than cells which do not express ATIA, for example human glioblastoma are more sensitive to TRAIL-induced cell death than cells which do not express ATIA. Accordingly, ATIA expression can be used as a marker to determine if a subject will respond to TRAIL therapy.

Potency and lack of toxicity to normal tissues make activation TRAIL death receptor signaling an attractive target for cancer therapy. For example, recombinant human (rh) TRAIL/Apo-2L, a TRAIL-encoding adenovirus, and monoclonal antibodies directed against TRAIL receptors R1 and R2 have been used to study cytotoxicity of TRAIL therapy in NSCLC cells (108). Recombinant TRAIL as well as agonistic anti-TRAIL-R1 and anti-TRAIL-R2 antibodies have entered clinical trials. Gene therapy approaches using TRAIL-encoding adenovirus (Ad-TRAIL) are being developed. To optimize gene therapy approaches, CD34+ cells transduced with Ad-TRAIL (CD34−TRAIL+) have been investigated as cellular vehicles for TRAIL delivery (109).

In certain embodiments, the method comprises determining the level of expression or biological activity of ATIA in a subject sample wherein an alteration in the level of expression or biological activity relative to the expression or biological activity in a reference indicates that the subject will respond to TRAIL therapy.

The invention also features methods of determining if a subject will respond to TRAIL therapy, the method comprising determining the level of expression or biological activity of a ATIA nucleic acid in a subject sample wherein an alteration in the level of expression relative to the expression in a reference indicates that the subject will respond to TRAIL therapy.

The invention also features methods of determining if a subject will respond to TRAIL therapy, the method comprising determining the amount of an ATIA protein in a subject sample wherein an alteration in the amount of the protein relative to the amount in a reference indicates that the subject will respond to TRAIL therapy.

In preferred embodiments, the subject has cancer. Preferably, the cancer is glioblastoma or astrocytoma; however any cancer that has elevated levels of ATIA may be a candidate for therapy.

In certain embodiments the invention features diagnostic methods. For example a subject, for example a patient, may be diagnosed for a propensity to develop cancer, e.g. brain cancer, by direct analysis of the sequence of an ATIA nucleic acid molecule. The sequence of an ATIA nucleic acid molecule derived from a subject is compared to a reference sequence. An alteration in the sequence of the ATIA nucleic acid molecule relative to the reference indicates that the patient has or has a propensity to develop cancer, e.g. brain cancer.

In another approach, diagnostic methods of the invention are used to assay the expression of an ATIA variant polypeptide in a biological sample relative to a reference (e.g., the level of ATIA polypeptide present in a corresponding control sample, or in a sample taken before a treatment, such as surgical treatment). In one embodiment, the level of an ATIA polypeptide is detected using an antibody that specifically binds an ATIA polypeptide.

Exemplary antibodies that specifically bind an ATIA polypeptide are described herein. Such antibodies are useful for the diagnosis of cancer. Methods for measuring an antibody-ATIA complex include, for example, detection of fluorescence, luminescence, chemiluminescence, absorbance, reflectance, transmittance, birefringence or refractive index. Optical methods include microscopy (both confocal and non-confocal), imaging methods and non-imaging methods. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra. Immunoassays can be used to determine the quantity of ATIA in a sample, where an increase in the level of ATIA polypeptide is diagnostic of a patient having cancer, e.g. brain cancer.

In general, the measurement of an ATIA polypeptide or nucleic acid molecule in a subject sample is compared with a diagnostic amount present in a reference. A diagnostic amount distinguishes between a diseased tissue or, for example a neoplastic tissue, and a control tissue. The skilled artisan appreciates that the particular diagnostic amount used can be adjusted to increase sensitivity or specificity of the diagnostic assay depending on the preference of the diagnostician. In general, any significant increase (e.g., at least about 10%, 15%, 30%, 50%, 60%, 75%, 80%, or 90%) in the level of an ATIA polypeptide or nucleic acid molecule in the subject sample relative to a reference may be used to diagnose cancer, e.g. brain cancer. In one embodiment, the reference is the level of ATIA polypeptide or nucleic acid molecule present in a control sample obtained from a patient that does not have cancer, e.g. brain cancer. In another embodiment, the reference is the level of ATIA polypeptide or nucleic acid molecule present in a control sample obtained from subjects with a disease of less severity, e.g., early stage non-aggressive brain cancer. In another embodiment, the reference is a baseline level of ATIA present in a biologic sample derived from a patient prior to, during, or after treatment for cancer, e.g. brain cancer. In yet another embodiment, the reference is a standardized curve.

Types of Biological Samples

The level of the soluble form of ATIA, the extracellular portion of ATIA, can be measured in different types of biologic samples. In one embodiment, the biologic sample is a biologic fluid sample (e.g., blood, blood plasma, serum, urine, seminal fluids, ascites, or cerebrospinal fluid). Preferably, the sample is a blood sample that is obtained from the subject.

The level of ATIA nucleic acid molecule can be measured in different types of biologic samples. In one embodiment, the biologic sample is a tissue sample that includes cells of a tissue or organ. Such tissue is obtained, for example, from a biopsy. In another embodiment, the biologic sample is a biologic fluid sample (e.g., blood, blood plasma, serum, urine, seminal fluids, ascites, or cerebrospinal fluid).

In certain exemplary embodiments, the sample is from a brain tumor. In preferred embodiments, the brain tumor is glioblastoma.

In other certain exemplary embodiments, the sample is from a subject undergoing treatment for brain cancer, e.g. glioblastoma or astrocytoma.

Therapeutics

As described herein, the present invention is based, in part, on the finding that there is high expression of ATIA in certain types of cancers, in particular in human glioblastoma and astrocytoma. Accordingly, the invention features, in preferred embodiments, ATIA as a therapeutic target. In certain embodiments, ATIA levels can be modulated, for example, by knocking down ATIA expression by siRNA or blocking its function through use of a neutralizing antibody or use of small molecules. The invention features in other preferred embodiments combination therapies, where eliminating ATIA function (for example, through siRNA knock down, neutralizing antibody or use of small molecules) along with ionizing radiation will improve existing treatment, and is based on the finding that knocking down ATIA expression leads to increased sensitivity of cells to apoptosis (cell death).

In certain embodiments, the present invention features a method of treating a patient with small molecule therapeutics. In particular, the patient will be determined to have elevated levels of ATIA, for example elevated levels of soluble ATIA. In particular preferred embodiments, the patient is treated with low levels of cyclohexamide. Cyclohexamide is an antibiotic produced by *Streptomyces griseus* that inhibits protein synthesis. Preferably, cyclohexamide is used at low doses that do not show toxicity to the patient, but are suitable to knockdown ATIA levels. Preferred doses of cylohexamide are 0.1 ug-1.0 ug. A particularly preferred dose is 0.5 ug.

Kits

The invention also provides kits for the diagnosis or monitoring of cancer, e.g. brain cancer, in a biological sample obtained from a subject. In one embodiment, the kit detects an increase in the expression of an ATIA nucleic acid molecule or polypeptide relative to a reference level of expression. In another embodiment, the kit detects an alteration in the sequence of an ATIA nucleic acid molecule derived from a subject relative to a reference sequence.

In preferred embodiments, ATIA is the soluble portion, for example as represented by SEQ ID NOs: 7-10.

In related embodiments, the kit includes reagents for monitoring the expression of an ATIA nucleic acid molecule, such as primers or probes that hybridize to an ATIA nucleic acid molecule. In other embodiments, the kit includes an antibody that binds to an ATIA polypeptide.

Optionally, the kit includes directions for monitoring an ATIA nucleic acid molecule or polypeptide levels in a biological sample derived from a subject. In preferred embodiments, ATIA is the soluble portion, for example as represented by SEQ ID NOs: 7-10.

In other embodiments, the kit comprises a sterile container which contains the primer, probe, antibody, or other detection regents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing cancer, e.g. brain cancer. Preferably, the kit further comprises any one or more of the reagents described in the diagnostic assays described herein. In other embodiments, the instructions include at least one of the following: description of the primer or probe; methods for using the enclosed materials for the diagnosis of cancer, e.g. brain cancer; precautions; warnings; indications; clinical or research studies; and/or references. The instructions may be printed directly on the container (when present), or as a label applied to the container, or as a separate sheet, pamphlet, card, or folder supplied in or with the container.

Antibodies

Antibodies are well known to those of ordinary skill in the science of immunology. As used herein, the term "antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv) and fusion polypeptides.

The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing ATIA polypeptides, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding an ATIA polypeptide, or immunogenic fragment thereof, can be provided to the host in a delivery vehicle that is taken up by immune cells of the host. The cells will in turn express the receptor on the cell surface generating an immunogenic response in the host. Alternatively, nucleic acid sequences encoding an ATIA polypeptide, or immunogenic fragments thereof, can be expressed in cells in vitro, followed by isolation of the receptor and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Polypeptides

The present invention encompasses ATIA polypeptides, for example biomarker polypeptides (e.g., SEQ ID NO: 2, 4, 6, 9 and 10) and fragments, variants, and derivatives thereof, that can be used to diagnose or predict cancer, and in particular brain cancer, as well as polynucleotides (e.g., SEQ ID NO: 1, 3, 5 7 and 8) encoding these peptides or polypeptides. In accordance with the invention, peptides can range in size from 5 amino acid residues to all but one residue of the entire sequence. Accordingly, peptides include, but are not limited to, fragments comprising at least 5, 6, 7, 8, 9, 10, 11, 12, 13, 14, 15, 20, 25, 30, 35, 45, 55, 65, 75 or more contiguous amino acids of any one of SEQ ID NO: 2, 4 or 6. In certain embodiments, the peptides comprise antigenic fragments of any one of SEQ ID NO: 2, 4 or 6.

The polypeptide, e.g. biomarker polypeptides, peptides, or fragments or variants thereof, may be linked to short tags, e.g., epitope tags such as HA and the like, or to other proteins, such as GST, GFP (e.g., GFP Y66F, GFP Y66H, GFP Y66W, wild type GFP, GFP S65A, GFP S65L, GFP S65T, ECFP, EYFP, DsRed; BD Biosciences CLONTECH, Palo Alto, Calif.), thioredoxin, maltose binding protein, etc. Also provided by the invention are chemically modified derivatives of the peptides and polypeptides of the invention that may provide additional advantages such as increased solubility, stability, and circulating time of the polypeptide. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

In addition, amino acid sequence variants of the present invention include, but are not limited to, variants that share at least 40%, 50%, 60%, 61%, 67%, 70%, 74%, 76%, 80%, 81%, 84%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% nucleotide sequence identity with any one of SEQ ID NO: 2, 4 or 6. For variants that are functional equivalents, the percent amino acid sequence identity is at least 61% or 67%. More preferably, the percent amino acid sequence identity is at least 74% or 76%, still more preferably, at least 81% or 84%, and even more preferably, at least 90% to any one of SEQ ID NO: 2, 4 or 6. However, one of skill in the art will appreciate that biological function need not be maintained where a biomarker peptide comprises an antigenic epitope.

Polypeptide and peptide variants include variants differing by the addition, deletion, or substitution of one or more amino acid residues. For example, to isolate biomarker polypeptides or peptides, it may be useful to encode a tagged biomarker peptide or polypeptide that can be recognized by a commercially available antibody. In particular, a peptide or polypeptide can be fused or linked to epitope tags (e.g., FLAG, HA, GST, thioredoxin, maltose binding protein, etc.), or affinity tags such as biotin and/or streptavidin. As one example, a system for the ready purification of non-denatured fusion proteins expressed in human cell lines has been described by Janknecht et al., (1991, Proc. Natl. Acad. Sci. USA, 88:8972-8976). In this system, the gene of interest is subcloned into a vaccinia recombination plasmid such that the open reading frame of the gene is translationally fused to an amino-terminal tag having six histidine residues. The tag serves as a matrix-binding domain for the fusion protein. Extracts from cells infected with the recombinant vaccinia virus are loaded onto an Ni2+ nitriloacetic acid-agarose column and histidine-tagged proteins are selectively eluted with imidazole-containing buffers.

A peptide or polypeptide tagged with an epitope or protein may also be engineered to contain a cleavage site located between the binder coding sequence and the tag coding sequence. This can be used to remove the tag, and isolate the biomarker peptide or polypeptide. The biomarker peptides or polypeptides of the invention can be covalently attached to chemical moieties via the amino acid backbone. For these purposes, the peptides or polypeptides may be modified by N- or C-terminal processing of the sequences (e.g., proteolytic processing), deletion of the N-terminal methionine residue, etc. The polypeptides may also be modified with a detectable label, such as an enzymatic, fluorescent, isotopic or affinity label to allow for detection and isolation of the protein, as described in detail herein.

Also included are modified polypeptides and peptides in which one or more residues are modified, and mutants comprising one or more modified residues. Amino acid variants of the invention can be generated by employing the techniques of gene-shuffling, motif-shuffling, exon-shuffling, and/or codon-shuffling (collectively referred to as "DNA shuffling"). DNA shuffling can be employed to generate peptides or polypeptides with altered activity. See, generally, U.S. Pat. Nos. 5,605,793; 5,811,238; 5,830,721; 5,834,252; and 5,837,458, and Patten et al., 1997, Curr. Opinion Biotechnol., 8:724-33; Harayama, 1998, Trends Biotechnol., 16(2):76-82; Hansson, et al., 1999, J. Mol. Biol., 287:265-76; and Lorenzo and Blasco, 1998, Biotechniques, 24(2):308-313, the contents of each of which are hereby incorporated by reference in its entirety.

The peptides and polypeptides may be differentially modified during or after translation, e.g., by derivatization with known protecting/blocking groups, proteolytic cleavage, linkage to an antibody molecule or other cellular ligand, etc. Useful modifications may include glycosylation, amidation, phosphorylation, sulfation, reduction/alkylation (Tarr, 1986, Methods of Protein Microcharacterization, J. E. Silver, Ed., Humana Press, Clifton, N.J., pp. 155-194); acylation (Tarr, supra); chemical coupling (Mishell and Shiigi (Eds), 1980, Selected Methods in Cellular Immunology, W H Freeman, San Francisco, Calif.; U.S. Pat. No. 4,939,239); and mild formalin treatment (Marsh, 1971, Int. Arch. of Allergy and Appl. Immunol. 41:199-215). Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc. Additional post-translational modifications encompassed by the invention include, for example, e.g., attachment of N-linked or O-linked carbohydrate chains, processing of N-terminal or C-terminal ends, chemical modifications of N-linked or O-linked carbohydrate chains, and addition or deletion of an N-terminal methionine residue as a result of prokaryotic host cell expression.

Additionally, D-amino acids, non-natural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, Int. Arch. Allergy Appl. Immunol. 64(1):84-99) to produce a protein conjugated with PEG. In addition, PEG can be added during chemical synthesis of the protein. Modifications or sequence variations may occur at the amino- or carboxy-terminal positions of the reference polypeptide sequence or anywhere between those terminal positions, interspersed either individually among the amino acids in the reference sequence or in one or more contiguous groups within the reference sequence. The polypeptides and peptides of this invention can be isolated, synthetic, or recombinant. The amino acid sequences may be obtained as individual polypeptides or peptides, or part of a complex.

Polypeptides or peptides may also be modified with a label capable of providing a detectable signal, either directly or indirectly, including, but not limited to, radioisotope, fluorescent, and enzyme labels. Fluorescent labels include, for example, Coumarin (e.g., Hydroxycoumarin, Aminocoumarin, Methoxycoumarin), R-Phycoerythrin (PE), Fluorescein, FITC, Fluor X, DTAF, Auramine, Alexa (e.g., Alexa Fluor® 350, -430, -488, -532, -546, -555, -568, -594, -633, -647, -660, -680, -700, -750), BODIPY-FL, Sulforhodamine (e.g., Texas Red), Carbocyanine, Rhodamine, XRITC, TRITC, Lissamine Rhodamine B, Peridinin Chlorphyll Protein (PerCP), Allophycocyanin (APC), PE-Cy5 conjugates (e.g., Cychrome, Tri-Color®, Quantum Red®), PE-Cy5.5 conjugates, PE-Cy7 conjugates, PE-Texas Red conjugates (e.g., Red613), PC5-PE-Cy5 conjugates, PerCP-Cy5.5 conjugates (e.g., TruRed), APC-Cy5.5 conjugates, APC-Cy7 conjugates, ECD-PE-Texas Red conjugates, Sulfonated Pyrene (e.g., Cascade Blue), AMCA Blue, Lucifer Yellow.

Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, colloidal gold, are known in the art, and are commercially available.

Polypeptides, e.g. biomarker polypeptides as described herein (peptides, and fragments, variants, and derivatives thereof) may be produced by direct peptide synthesis using solid-phase techniques (J. Merrifield, 1963, J. Am. Chem. Soc., 85:2149-2154; J. Y. Roberge et al., 1995, Science, 269:202-204). Protein or peptide synthesis may be performed using manual techniques or by automation. Automated synthesis may be achieved, for example, using ABI 431A Peptide Synthesizer (PE Biosystems). Various fragments of a biomarker polypeptide or peptide can be chemically synthesized separately and then combined using chemical methods to produce the full-length molecule. The newly synthesized peptide can be substantially purified by preparative high performance liquid chromatography (e.g., T. Creighton, 1983, Proteins, Structures and Molecular Principles, W. H. Freeman and Co., New York, N.Y.), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of biomarker peptide or polypeptide or any portion thereof, may be altered during direct synthesis and/or combined using chemical methods with sequences from other proteins, or any part thereof, to produce a variant peptide or polypeptide.

Polypeptides, variants, and fragments thereof may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

For example, one particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

Polynucleotides

In general, the invention includes any nucleic acid sequence encoding an ATIA polypeptide. Also included in the methods of the invention are any nucleic acid molecule containing at least one strand that hybridizes with such a nucleic acid sequence (e.g., an inhibitory nucleic acid molecule, such as a dsRNA, siRNA, shRNA, or antisense molecule). An isolated nucleic acid molecule can be manipulated using recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid molecule that is isolated within a cloning or expression vector may comprise only a tiny percentage of the material in the cell in which it resides. Such a nucleic acid is isolated, however, as the term is used herein, because it can be manipulated using standard techniques known to those of ordinary skill in the art.

Screening Assays

As reported herein, the expression of ATIA polypeptide is increased in neoplastic tissues, and in particular examples in neoplastic tissues from patients with cancer, and in particular, brain cancer. Accordingly, compounds that modulate the expression or activity of ATIA polypeptide, variant, or fragment thereof are useful in the methods of the invention for the treatment or prevention of brain cancer, and in particular brain cancer. Any number of methods are available for carrying out screening assays to identify such compounds. In one approach, candidate compounds are identified that specifically bind to and alter the activity of a polypeptide of the invention (e.g., an ATIA activity). Methods of assaying such biological activities are known in the art and are described herein. The efficacy of such a candidate compound is dependent upon its ability to interact with an ATIA polypeptide, variant, or fragment. Such an interaction can be readily assayed using any number of standard binding techniques and functional assays (e.g., those described in Ausubel et al., supra). For example, a candidate compound may be tested in vitro for interaction and binding with a polypeptide of the invention. Standard methods for perturbing or reducing ATIA expression include mutating or deleting an endogenous ATIA sequence, interfering with ATIA expression using RNAi, or microinjecting an ATIA-expressing cell with an antibody that binds ATIA and interferes with its function.

Potential agonists and antagonists of an ATIA polypeptide include organic molecules, peptides, peptide mimetics, polypeptides, nucleic acid molecules (e.g., double-stranded RNAs, siRNAs, antisense polynucleotides), and antibodies that bind to a nucleic acid sequence or polypeptide of the invention and thereby inhibit or decrease its activity. Potential antagonists also include small molecules that bind to the ATIA polypeptide thereby preventing binding to cellular molecules with which the ATIA polypeptide normally interacts, such that the normal biological activity of the ATIA polypeptide is reduced or inhibited. Small molecules of the invention preferably have a molecular weight below 2,000 daltons, more preferably between 300 and 1,000 daltons, and most preferably between 400 and 700 daltons. It is preferred that these small molecules are organic molecules.

For example, a recombinant polypeptide of the invention may be purified by standard techniques from cells engineered to express the polypeptide (e.g., those described above) and may be immobilized on a column. A solution of candidate compounds is then passed through the column, and a compound specific for the ATIA polypeptide is identified on the basis of its ability to bind to the ATIA polypeptide and be immobilized on the column. To isolate the compound, the column is washed to remove non-specifically bound molecules, and the compound of interest is then released from the column and collected.

In one particular example, methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to alter the biological activity of an ATIA polypeptide.

Any in vivo protein interaction detection system, for example, any two-hybrid assay may be utilized to identify compounds that interact with an ATIA polypeptide. Interacting compounds isolated by this method (or any other appropriate method) may, if desired, be further purified (e.g., by high performance liquid chromatography). Compounds isolated by any approach described herein may be used as therapeutics to treat cancer, e.g. brain cancer in a human patient.

In addition, compounds that inhibit the expression of an ATIA nucleic acid molecule whose expression is increased in a patient having a cancer, e.g. brain cancer, are also useful in the methods of the invention. Any number of methods are available for carrying out screening assays to identify new candidate compounds that alter the expression of an ATIA nucleic acid molecule. In one working example, candidate compounds are added at varying concentrations to the culture medium of cultured cells expressing one of the nucleic acid sequences of the invention. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate compound is compared to the level measured in a control culture medium lacking the candidate molecule. A compound that promotes an alteration in the expression of an ATIA gene, or a functional equivalent thereof, is considered useful in the invention; such a molecule may be used, for example, as a therapeutic to treat cancer, e.g. brain cancer in a human patient.

In another approach, the effect of candidate compounds is measured at the level of polypeptide production to identify those that promote an alteration in an ATIA polypeptide level. The level of ATIA polypeptide can be assayed using any standard method. Standard immunological techniques include Western blotting or immunoprecipitation with an antibody specific for an ATIA polypeptide. For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, Western blot, or RIA assay) to measure the level of the polypeptide. In some embodiments, a compound that promotes a decrease in the expression or biological activity of the polypeptide is considered particularly useful. Again, such a molecule may be used, for example, as a therapeutic to delay, ameliorate, or treat cancer, e.g. brain cancer in a human patient.

In another embodiment, a nucleic acid described herein (e.g., an ATIA nucleic acid) is expressed as a transcriptional or translational fusion with a detectable reporter, and expressed in an isolated cell (e.g., mammalian or insect cell) under the control of a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that alters the expression of the detectable reporter is a compound that is useful for the treatment of a brain cancer. In one embodiment, the compound decreases the expression of the reporter.

Each of the DNA sequences listed herein may also be used in the discovery and development of a therapeutic compound for the treatment of brain cancer, in particular brain cancer. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra).

The invention also includes novel compounds identified by the above-described screening assays. Optionally, such compounds are characterized in one or more appropriate animal models to determine the efficacy of the compound for the treatment of cancer, e.g. brain cancer. Desirably, characterization in an animal model can also be used to determine the toxicity, side effects, or mechanism of action of treatment with such a compound. Furthermore, novel compounds identified in any of the above-described screening assays may be used for the treatment of cancer, e.g. brain cancer in a subject. Such compounds are useful alone or in combination with other conventional therapies known in the art.

Test Compounds and Extracts

In general, compounds capable of inhibiting the growth or proliferation of cancer, e.g. brain cancer by altering the expression or biological activity of an ATIA polypeptide, variant, or fragment thereof are identified from large libraries of either natural product or synthetic (or semi-synthetic) extracts or chemical libraries according to methods known in the art. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al., *J. Med. Chem.* 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to alter the biological activity of an ATIA polypeptide, variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having anti-neoplastic activity. Methods of fractionation and purification of such heterogenous extracts are known in the art. If desired, compounds shown to be useful agents for the treatment of a neoplasm, e.g. brain cancer, are chemically modified according to methods known in the art.

Microarrays

The methods of the invention may also be used for microarray-based assays that provide for the high-throughput analysis of biomarkers. The ATIA nucleic acid molecules or polypeptides of the invention are useful as hybridizable array elements in such a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28:e3.i-e3.vii, 2000), MacBeath et al., (Science 289:1760-1763, 2000), Zhu et al. (Nature Genet. 26:283-289), and in U.S. Pat. No. 6,436,665, hereby incorporated by reference.

Nucleic Acid Microarrays

To produce a nucleic acid microarray oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, cerebrospinal fluid, phlegm, saliva, or urine) or tissue sample (e.g. a tissue sample obtained by biopsy, e.g. brain tissue). For some applications, cultured cells or other tissue preparations may be used. The mRNA is isolated according to standard methods, and cDNA is produced and used as a template to make complementary RNA suitable for hybridization. Such methods are described herein. The RNA is amplified in the presence of fluorescent nucleotides, and the labeled probes are then incubated with the microarray to allow the probe sequence to hybridize to complementary oligonucleotides (e.g., ATIA nucleic acid molecules) bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., at least about 42° C., or at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Protein Microarrays

ATIA polypeptides, such as those described herein, may also be analyzed using protein microarrays. Such arrays are useful in high-throughput low-cost screens to identify peptide or candidate compounds that bind a polypeptide of the invention, or fragment thereof. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, ATIA polypeptides are spotted on a substrate using any convenient method known to the skilled artisan (e.g., by hand or by inkjet printer). Preferably, such methods retain the biological activity or function of the protein bound to the substrate (e.g., ATIA antibody binding).

The protein microarray is hybridized with a detectable probe. Such probes can be polypeptide (e.g., an ATIA antibody), nucleic acid, or small molecules. For some applications, polypeptide and nucleic acid probes are derived from a biological sample taken from a patient, such as a bodily fluid (such as blood, urine, saliva, or phlegm); a homogenized tissue sample (e.g. a tissue sample obtained by biopsy, e.g. from the brain); or cultured cells (e.g., lymphocytes). Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of nonspecific probes, specifically bound probes are detected, for example, by fluorescence, enzyme activity (e.g., an enzyme-linked calorimetric assay), direct immunoassay, radiometric assay, or any other suitable detectable method known to the skilled artisan.

Detection of an increase in the amount of an ATIA polypeptide or an ATIA polynucleotide present in a patient sample is useful as a diagnostic for the presence of brain cancer. Optionally, ATIA detection may be combined with the detection of other biomarkers, where the presence or level of the biomarker is correlated with the presence of cancer, e.g. brain cancer.

ELISA

In certain embodiments, the invention provides a method for detecting ATIA levels in biological fluids, for example in the blood. The method is based on the finding that ATIA has a soluble form, the extracellular portion of ATIA, and the soluble ATIA can be detected in the culture medium of all types of ATIA-expressing cells. Accordingly, it is possible to diagnose the disease by assaying biological samples for the presence of the extracellular portion of ATIA.

In preferred embodiments, soluble ATIA corresponds to SEQ ID NOs 9 or 10, or fragments thereof.

In a preferred embodiments, ATIA levels are detected by immunoassay, for example ELISA. Generally, immunoassays involve the binding of ATIA and anti-ATIA antibody. The presence and amount of binding indicate the presence and amount of ATIA present in the sample. Examples of immunoassays include, but are not limited to, protein arrays, ELISAs, radioimmunoassays, and immunoblots, which are well known in the art. The antibody can be polyclonal or monoclonal as described herein, and is preferably labeled for easy detection. The labels can be, but are not limited to biotin, fluorescent molecules, radioactive molecules, chromogenic substrates, chemi-luminescence, and enzymes.

In one embodiment, ELISA, based on the capture of ATIA by immobilized monoclonal anti-ATIA antibody followed by detection with biotinylated polyclonal anti-ATIA antibody, is used to detect ATIA.

Preferably, the extracellular portion of ATIA can be detected using an ELISA assay.

The process can be automated. Automated ELISA reader devices are well known in the art (Davis, et al. Microbiology 4th. ed., pp. 269-270 (1990)) and are commercially available (see, e.g., Multiskan E X and R C, Komabiotech, Seoul, Republic of Korea; HT3, Anthos Analytical, Durham, N.C.).

Pharmaceutical Compositions

The present invention contemplates pharmaceutical preparations comprising ATIA neutralizing antibodies, ATIA small molecule inhibitors, or ATIA inhibitory polynucleotides, or polypeptides, or analogs (e.g., a polynucleotide that hybridizes to and interferes with the expression of an ATIA polynucleotide), together with a pharmaceutically acceptable carrier. Polynucleotides of the invention may be administered as part of a pharmaceutical composition. The compositions should be sterile and contain a therapeutically effective amount of the polypeptides or nucleic acid molecules in a unit of weight or volume suitable for administration to a subject.

These compositions ordinarily will be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous ATIA polynucleotide solution, such as an aqueous solution of ATIA polynucleotide or polypeptide, and the resulting mixture can then be lyophilized. The infusion solution can be prepared by reconstituting the lyophilized material using sterile Water-for-Injection (WFI).

The ATIA neutralizing antibodies, ATIA small molecule inhibitors, or ATIA inhibitory polynucleotides, or polypeptides, or analogs may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with the molecules of the present invention, and with each other, in a manner such that there is no interaction that would substantially impair the desired pharmaceutical efficacy.

The compositions can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having cancer, and in particular a glioblastoma or astrocytoma, an effective amount is sufficient to stabilize, slow, or reduce the progression of the disease or disorder.

Tumors, and in particular brain tumors, can be monitored by imaging, for example by CAT scan, MR Spectroscopy, or MRI. Other diagnostics include angiograms or arteriograms, which are a series of X-rays taken after a special dye is injected into an artery, usually in the area where the abdomen joins the top of the leg. The dye, which flows through the blood vessels of the brain, can be seen on X-rays. These X-rays can show the tumor and connecting blood vessels. A brain scan may be used to reveal areas of abnormal growth in the brain.

Generally, doses of inhibitory oligonucleotide compositions of the present invention would be from about 0.01-1000 mg/kg per day. Lower doses will result from certain forms of administration, such as intravenous administration. Generally, doses of neutralizing antibody compositions of the present invention would be from about 0.01-1000 mg/kg per day.

In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of the ATIA polynucleotide or polypeptide compositions of the present invention.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes. Other useful approaches are described in Otto, D. et al., J. Neurosci. Res. 22: 83-91 and in Otto, D. and Unsicker, K. J. Neurosci. 10: 1912-1921.

Combination Therapies

The invention also features combination therapies.

According to certain embodiments, compositions and methods of the invention may be used in combination with any conventional therapy known in the art.

In particular embodiments, therapies that cross the blood brain barrier (BBB) are particularly useful in methods of treating or preventing brain tumors.

The blood-brain barrier (BBB) is a metabolic or cellular structure in the central nervous system that restricts the passage of various chemical substances and microscopic objects between the bloodstream and the neural tissue itself, while still allowing the passage of substances essential to metabolic function (e.g. oxygen). The BBB results from the selectivity of the tight junctions between endothelial cells in CNS vessels that restricts the passage of solutes.

Certain therapeutics have been designed that are able to pass through the BBB, including, for example, etoposide and cisplatinum.

In part, the invention is based in the finding that ATIA expression in human glioblastoma cells (such as, but not limited to, A172 cells), are much more sensitive to TRAIL-induced cell death than cells which do not express ATIA. For example, U87MG cells do not express ATIA. Accordingly, in preferred embodiments, ATIA expression can be used as an indicator for TRAIL treatment. TRAIL is a promising treatment of glioblastoma and is currently in clinical trials.

The invention is based, also, on the finding that knocking down ATIA expression in human glioblastoma cells, such as A172 cells, renders the cells more sensitive to anti-cancer drugs. Exemplary anti-cancer drugs include, but are not limited to the following:

acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elformithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2''-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminol evulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase;

peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Preferred additional anti-cancer drugs are 5-fluorouracil and leucovorin. Additional cancer therapeutics include monoclonal antibodies such as rituximab, trastuzumab and cetuximab.

In preferred embodiments, ATIA therapy (e.g. knockdown or inhibition) is carried out in combination with administration of the anti-cancer drug cisplatinum.

In other preferred embodiments, ATIA therapy (e.g. knockdown or inhibition) is carried out in combination with ionizing radiation treatment.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

Example 1

Identification of Atia as a Novel Anti-apoptotic Protein Against TNF Induced Apoptosis The proinflammatory cytokine tumor necrosis factor (TNF) plays an important role in diverse cellular events such as septic shock, induction of other cytokines, cell proliferation, differentiation, necrosis and apoptosis (1, 2, 3). TNF was originally identified as a factor that leads to rapid hemorrhagic necrosis of transplantable tumors in mice (4). Approximately one third of transformed cell lines were shown to be susceptible to the cytolytic action of TNF (5). However, because of its toxicity in animals and human, TNF did not fulfill the initial expectations that it would be useful in the treatment of cancer (6). Studies from many laboratories have demonstrated that the diverse TNF-mediated biological responses are achieved through activating multiple signaling pathways. Many of the TNF-induced cellular responses are mediated by either one of the two TNF receptors, TNF-R1 and TNF-R2, both of which belong to the TNF receptor super-family (7, 8, 9). In response to TNF treatment, the transcription factor NF-KB and MAP kinases, including ERK, p38 and JNK, are activated in most types of cells and, in some cases, apoptosis or necrosis could also be induced (10, 11, 12, 13, 14). However, induction of apoptosis or necrosis is mainly achieved through TNF-R1, which is also known as a death receptor (15, 16, 17). The initiation of these TNF-induced pathways is precisely regulated under physiological conditions and the aberrant commitment or failure of these pathways is often accountable for many human diseases, such as cancer, arthritics and AIDS (1, 3).

Many molecular aspects of TNF signaling remain unknown. Particularly, the decision of life and death in response to TNF is still not understood. It is known now that one of the reasons for the inefficiency of TNF killing is the activation of NF-KB in response to TNF treatment (18). Studies from several labs have demonstrated that NF-KB activation protects cells against TNF-induced apoptosis (18). Inhibition of NF-kB activation renders many types of cells TNF sensitive. Several of NF-KB's target genes, including cIAP-1, cIAP-2 and IEX-1L, cFlip, have anti-apoptotic properties (19, 20, 21). At the same time, results suggest that there are also NF-KB-independent pathways that are important components of the protective machinery against TNF-induced apoptosis. For instance, it has been proposed that TRAF2 protects cells against TNF-induced apoptosis independently of NF-KB (22). The machinery of this TRAF2-dependent anti-apoptotic pathway is largely unknown, although we found that a member of SP 1 transcription factors, LKLF, is downstream of TRAF2 and protects cells against TNF-induced apoptosis (23). To further understand the molecular mechanisms of TRAF2-mediated cell protection against TNF-induced apoptosis, the experiments described herein are directed to identifying additional proteins that function downstream of TRAF2 and protect cells against TNF-induced apoptosis. Through screening a retroviral cDNA expression library for genes that protect TRAF2 null cells following TNF treatment, we identified a novel anti-apoptotic gene, ATIA (anti-TNF-induced apoptosis). Thehe human homolog of ATIA, Vasorin, was reported after the present inventors cloned ATIA, and vasorin was found to be a TGFβ-binding protein (24). The present inventors have demonstrated that ATIA is a multi-functional protein that regulates TGF-beta signaling and protects cells against TNF-induced apoptosis. The present inventors have found that ATIA protein localizes in the cell plasma membrane and the mitochondria and that ATIA mutant protein targeted to mitochondria is capable of protecting cells against TNF-induced apoptosis. The present inventors have shown that by generating ATIA knockout mice, ATIA protects cells against TNF-induced apoptosis in vivo.

To screen for potential anti-apoptotic genes, a retroviral cDNA expression library was constructed with mRNA isolated from wild-type MEFs. This library was used to infect TRAF2−/− cells. The infected cells were induced to undergo apoptosis with TNF treatment as TRAF2−/− MEFs are super-sensitive to TNF-induced apoptosis (25). The surviving cells were then collected for recovering the infected cDNA, which presumably is responsible for the increased resistance of the infected cells to TNF-induced apoptosis. Through such a screening approach, the gene, ATIA (anti-TNF-induced apoptosis), which encodes a novel protein with a putative transmembrane domain (FIG. 1A).

Figure 1B:
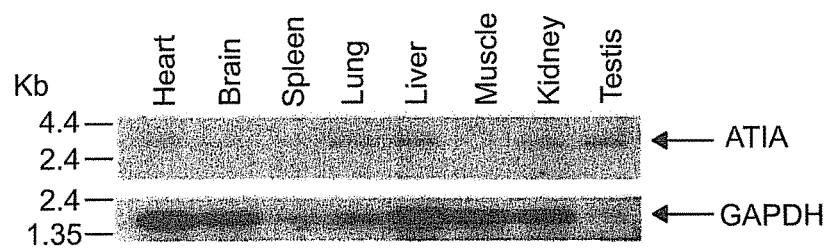
Figure 1C:
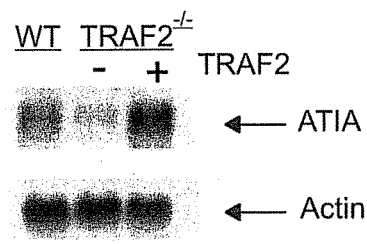
Figure 2A:
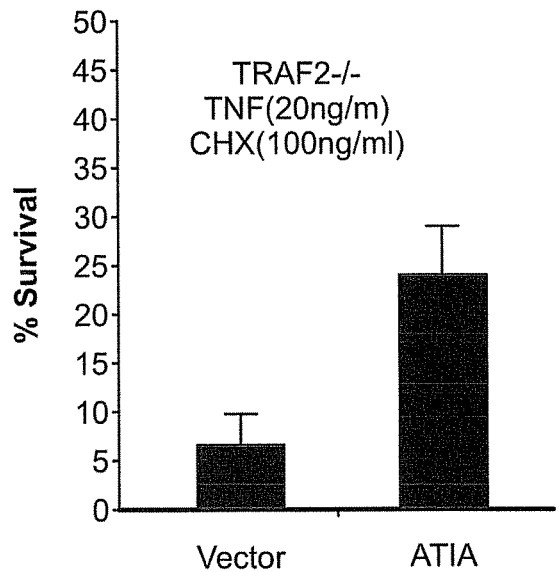
FIGS. 2 (A and B) are graphs that shows ATIA protects cells against TNF-induced apoptosis. The graphs show ectopic expression of ATIA protects TRAF−/− MEFS (A) and MCF7 cells (B).

Initially, it was concluded that the isolated cDNA clone encodes a full length 51 Kd protein. However, when the mouse genomic DNA sequence became available, it was realized that only a portion of the ATIA gene from an in-frame ATG codon had been cloned, and that there is another 848 bps at the 5' end of the gene. Therefore, the original clone was designated ATIAc (see FIG. 1A). The full length cDNA of ATIA encodes a protein with 673 a.a, which has a predicted molecular weight of 72 Kd. As shown in FIG. 1B. The 673 a.a. full length protein corresponds to SEQ ID NO: 2. As shown in FIG. 1B, ATIA is highly expressed in some tissues such as liver, lung, kidney, and testis. Importantly, the expression of ATIA is considerably reduced in the TRAF2−/− cells while the ectopic-expression of TRAF2 restored the expression of ATIA (FIG. 1C). However, ATIA expression is not inducible by TNF (data not shown). When ATIA or ATIAc was over-expressed in TRAF2−/− or human breast carcinoma MCF7 cells, it protected cells from TNF-induced apoptosis (FIG. 2, and data not shown). Therefore, ATIA is a potential anti-apoptotic gene that protects cells against TNF-induced apoptosis.

Figure 2B:
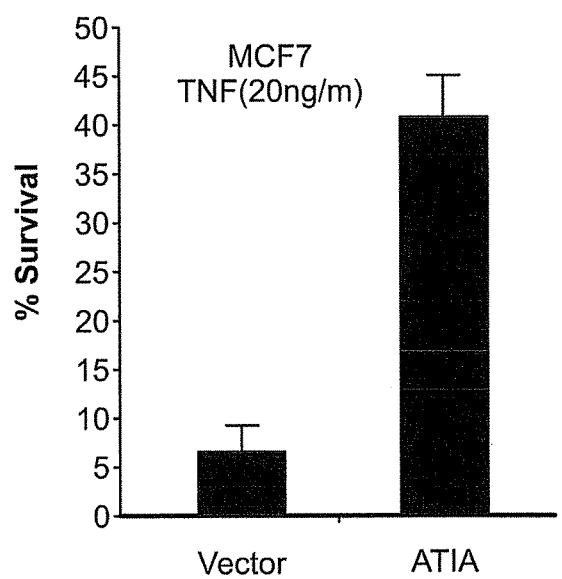
Figure 3A:
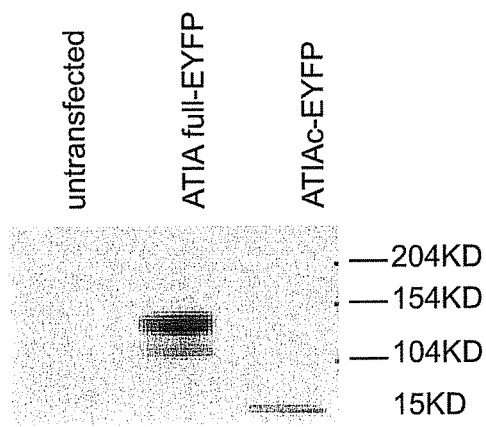
FIG. 3 (A-C) shows the cellular localization of ATIA protein. (A) Expression of ATIA full-length and ATIAc YF P fusion proteins. (B) and (C) shows confocal microscopy of living wild-type ME Fs transiently transfected with EY FP-tagged ATIA full-length and ATIAc constructs. The bottom panel shows mitochondrial staining that was performed by MitoTracker.
Figure 3B:
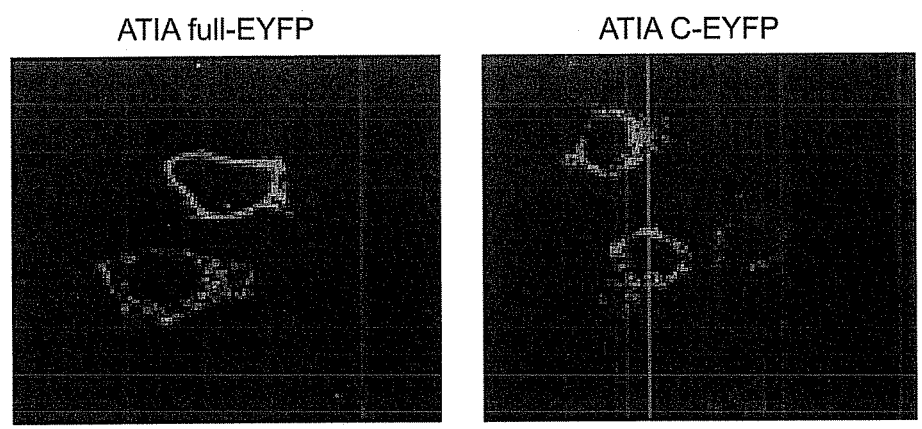
Figure 3C:
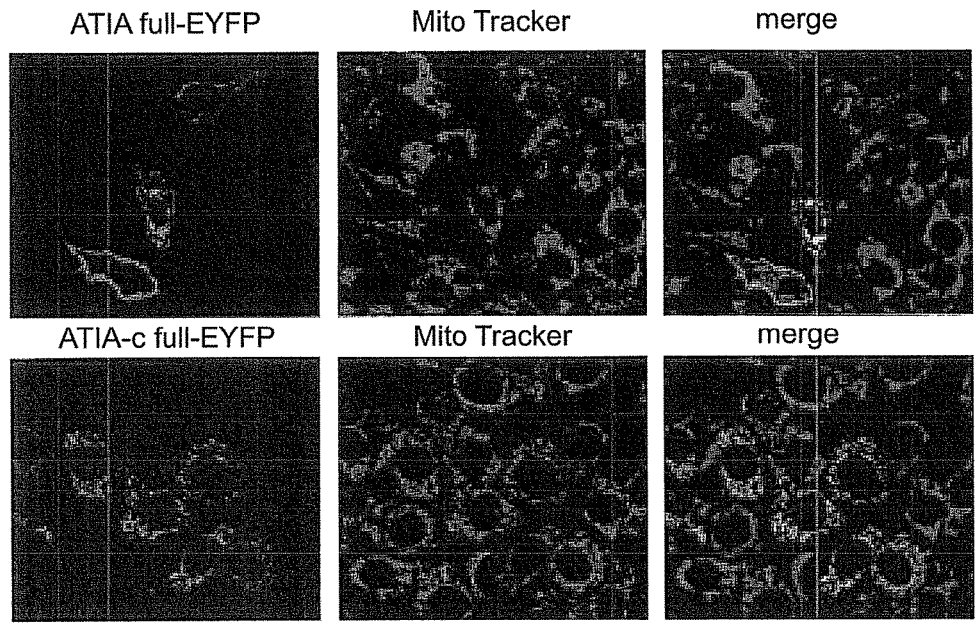

Additional information about ATIA function was provided by studying its cellular localization. ATIA has a signal peptide at its N-terminus and a putative transmembrane domain, suggesting that it may localize to the plasma membrane. To test this possibility, full length ATIA and the truncated ATIAc construct were cloned into vectors that created c-terminal YFP-tagged ATIA proteins, ATIA-YFP and ATIAc-YFP. These constructs were transfected into wt MEFs. Western blot analysis with an anti-GFP antibody indicates that the expression of the full-length ATIA-YFP gives two products, a major one at about 130 KD and a minor one at about 110 Kd (FIG. 3A). Since the predicted molecular weight of ATIA-YFP is about 97 Kd without the signal peptide, the larger sizes of the products are apparently due to additional modifications of the proteins, that it is believed are at least partially due to glycosylation (data not shown). The ATIAc-YFP construct gives a product at the predicted 75 Kd (FIG. 3A), indicating that the modifications are likely within the first 231 amino acids of the ATIA protein. Confocal microscopy demonstrated that the majority of the cells transfected with the full-length construct had intense labeling of the plasma membrane while some cells showed a punctate pattern in the cytoplasm (FIG. 2B). Cells transfected with the truncated ATIAc construct demonstrated only punctuate expression and no membrane expression (FIG. 3B). This punctate pattern resembled mitochondrial localization. To confirm this, transfected cells were stained with mitochondrial marker MitoTracker. Indeed, full-length ATIA localized to the plasma membrane in the vast majority of cells with about 30% of cells having some mitochondrial localization (FIG. 3C). ATIAc was found only in mitochondria. As ATIAc lacks the signal peptide, this data confirmed the role of the signal peptide in targeting ATIA to the plasma membrane. Since the expression of ATIA-YFP plasmid yields two different sized products, these two products may represent the ATIA protein localized to the plasma membrane and mitochondria, respectively.

To confirm the protective ability of these two plasmids, microinjections of TRAF2−/− MEFs with EYFP vector, ATIA-YFP or ATIAc-YFP were performed. Cells injected with EYFP vector were sensitive to TNF-induced apoptosis with less than 15% of the cells surviving after 6 hours. Cells injected with either ATIA-YFP or ATIAc-YFP plasmid were protected at a 60% or 45% survival rate, respectively (data not shown). These results suggest that the mitochondrially localized ATIA is capable of protecting cells against TNF-induced apoptosis.

Figure 4:
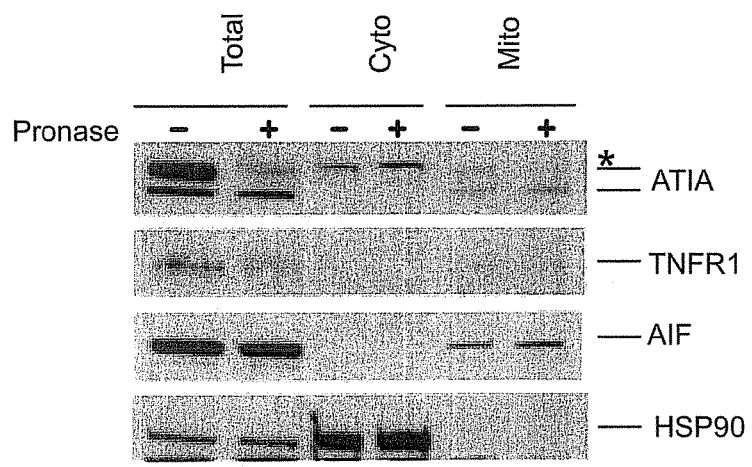
FIG. 4 shows the results of western blot experiments examining ATIA localization by cell fractionation. Wild type MEF cells were collected for fractionation before and after pronase treatment. Western blotting was carried out with different antibodies. * nonspecific band.

To further verify the membrane and mitochondrial localizations of ATIA, cell fractionation experiments were performed with wild-type MEF cells before and after treatment with pronase, a proteolytic enzyme that removes exposed membrane proteins. The presence of different proteins in total cell lysates or in mitochondrial fractions was analyzed by Western blotting with different antibodies. Using an anti-ATIA antibody with an epitope to the whole intracellular domain (ICD) comprising 600 amino acids, the endogenous ATIA protein from wild-type MEFs before pronase treatment was detected at two different sizes in the total cell lysate, a dominant upper band (100 Kd) and a weaker lower band (80 Kd) (FIG. 4). This is consistent with what was observed when ATIA is overexpressed (FIG. 3). Upon pronase treatment, the upper band of ATIA disappears while the lower band of ATIA is not affected. However, in the enriched mitochondrial fraction, the ratio between the upper and lower band of ATIAs is dramatically altered prior to pronase treatment, suggesting the lower band is enriched in the mitochondrial fraction (FIG. 4). This enrichment of the smaller size of ATIA in the mitochondrial fraction is not affected by the pronase treatment. Both ATIA bands are absent in the cytosolic fraction. These results support the idea that the upper band of ATIA is localized to the plasma membrane and the smaller form of ATIA is in the mitochondria. Western blotting with other control antibodies further confirmed this conclusion. Therefore, the two forms of ATIA proteins were designated as memATIA and mitoATIA respectively.

Example 2

ATIA Protects Cells Against TNF-induced Apoptosis In Vivo

Figure 5A:
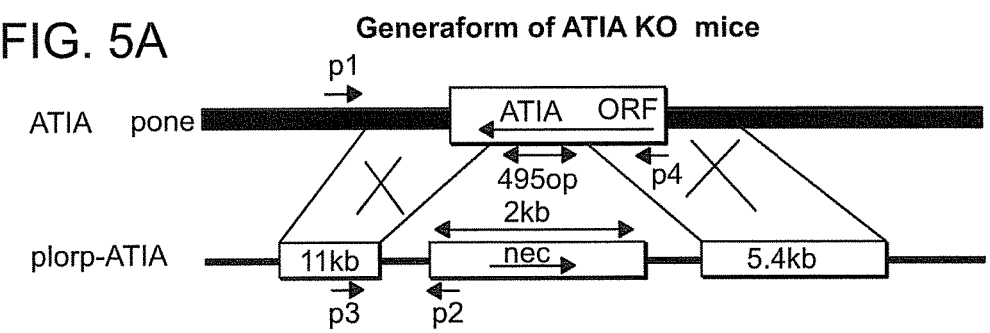
FIG. 5 (A-E) shows ATIA null mice are generated and more sensitive to TNF toxicity. (A) is a schematic diagram of ATIA knockout strategy. (B) and (C) show the generation of ATIA+/− ES cells (B) and ATIA+/− and ATIA−/− mice (C) was confirmed by PCR. (D) and (E) shows that ATIA KO mice are more sensitive to TNF-induced apoptosis. Survival curves of wild-type (n=5) and ATIA KO (n=8) after TNF treatment. (D) shows histological analysis of liver tissue isolated 4 hours after administration of GaIN and INFcc (E). Tissue sections were analyzed by H&E (left panels) and TUNNEL (right panels) staining.
Figure 5B:
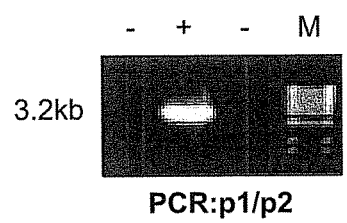
Figure 5C:
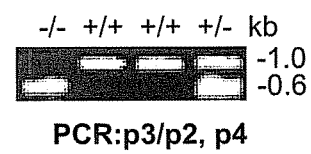

To further study the physiological function of ATIA, ATIA knockout mice were generated. As shown in FIG. 5, the region of ATIA from a.a 449 to as 619 was deleted because this region of ATIA is essential for protecting cells from TNF-induced apoptosis based on in vitro study data (not shown). The presence of mutant ATIA allele in ES cells was confirmed by PCR and DNA sequencing of the PCR product (FIG. 5B, data not shown). The offspring were genotyped by PCR (FIG. 5C) and confirmed by RT-PCR (Data not shown). The ATIA+/− heterozygotic mice were backcrossed to C57BL/6 mice for 8 generations. The resulting heterozygotic mice were bred to each other and the homozygotic wild type and knockout progeny were used in all subsequent in vivo experiments. ATIA knockout mice appear normal phenotypically, however, male ATIA knockout mice appear to have impaired fertility.

Figure 5D:
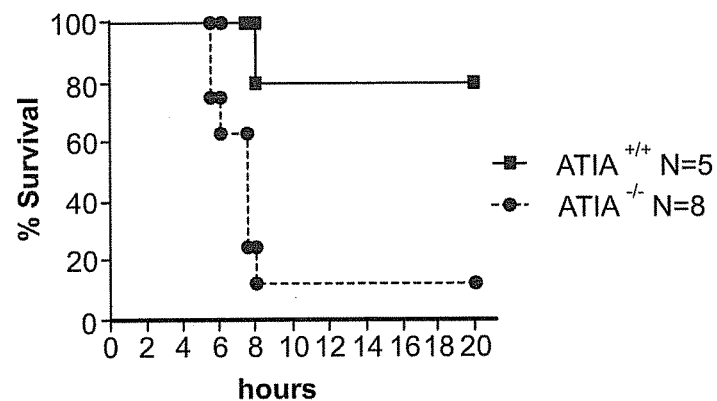
Figure 5E:
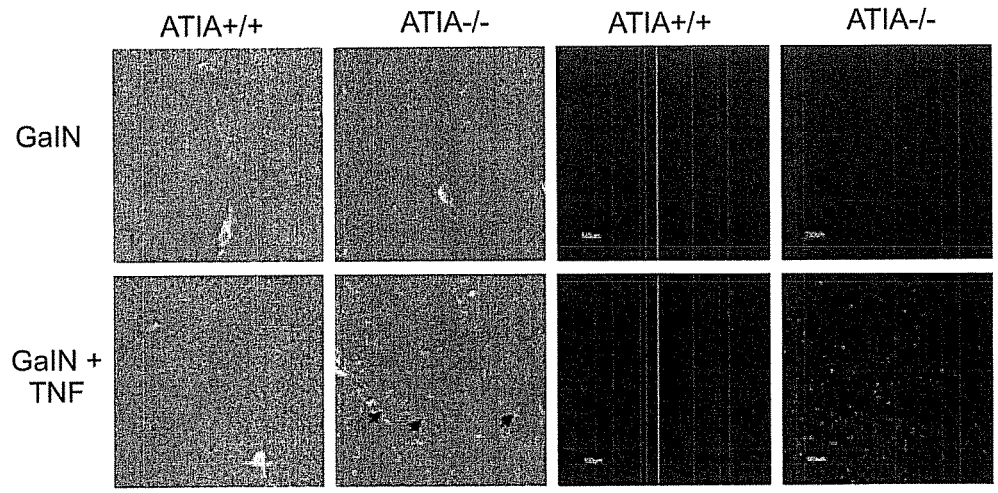
Figure 6A:
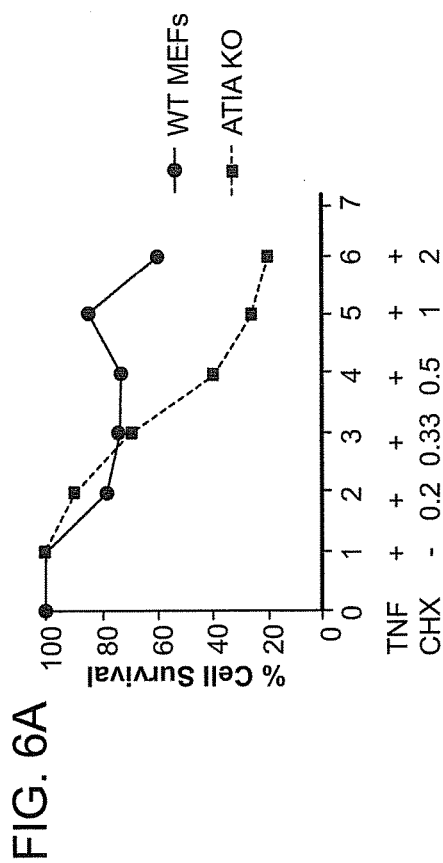
FIG. 6 (A and B) are graphs that show ATIA−/− MEFs are more sensitive to TNF-induced apoptosis. (A) ATIA−/− MEFs are more sensitive to TNF-induced apoptosis. Wild-type and ATIA−/− MEFs were treated with TNFα (30ng/ml) and indicated concentrations of cycloheximide for 16 hours. Cell survival was measured by MTT. (B) shows that ATIA−/− MEFs are not more sensitive to UV (left) and Staurosporine treatment (right).
Figure 6B:
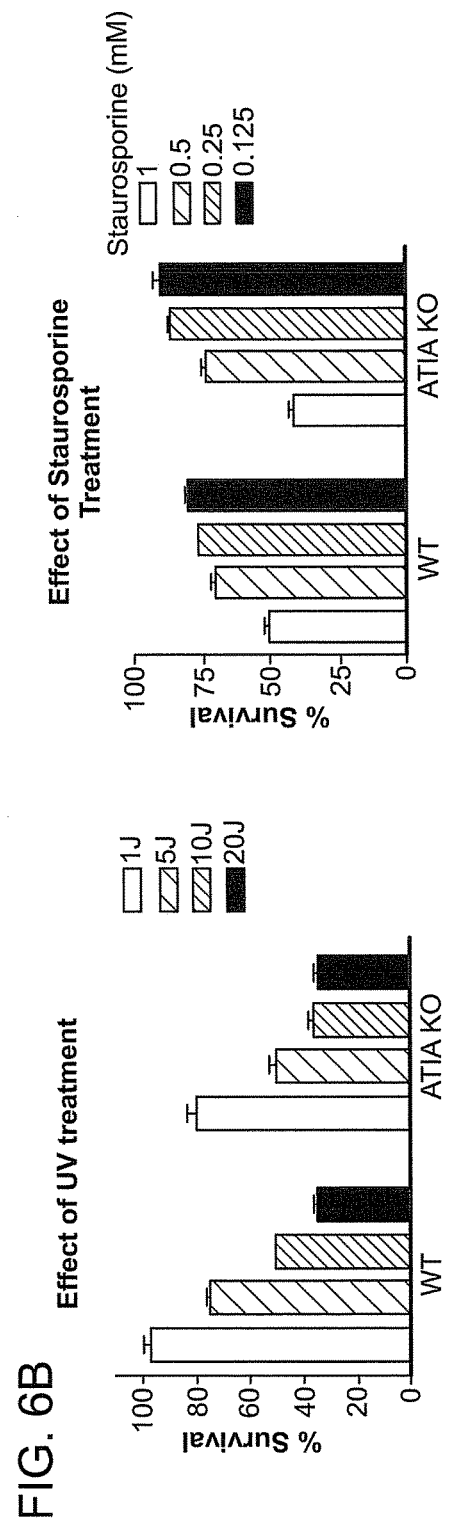

To determine whether ATIA is able to protect from TNF-induced apoptosis in vivo, a model of TNF-induced hepatitis (26, 27) was used. ATIA−/− and ATIA±/±litter mates from heterozygote cross were pretreated with an inhibitor of transcription that is specific for the liver, D-galactosamine (GalN), which metabolically inhibits hepatocyte RNA and protein synthesis, followed by intravenous injection of a sub-lethal dose of TNFα (2 μg/Kg). By 8 hr post-treatment, 20% of ATIA+/+ mice as compared to more than 85% of ATIA—mice were moribund (FIG. 5D). Histological analysis of H&E stained liver sections 4 hours after TNFa administration demonstrated significant apoptosis in livers of ATIA-deficient mice, while ATIA+/+ litter mates showed little to no apoptosis (FIG. 5E). No other histological differences were noted. TUNEL staining of liver sections also showed a dramatic increase in TUNEL-positive cells in the ATIA−/− liver sections as compared to the ATIA±/± litter mates (FIG. 5E). To further confirm this observation, we also examined TNF-induced apoptosis in ATIA−/− MEFs. Wild-type and ATIA−/− mouse embryonic fibroblast cell lines were established from 10.5-12.5 day old wild-type and ATIA knockout embryos. The cell lines were verified for the loss of ATIA by genomic PCR analysis and western blotting with the anti-ATIA antibody (data not shown). Cells were treated with TNF and varied doses of cyclohexamide (CHX) (FIG. 6A). At 8 hours, ATIA KO cells show an increase in cell death compared to wild type cells as measured by MTT assay, suggesting that the loss of ATIA increases the sensitivity to TNF-induced apoptosis. Cell death induced by UV radiation or staurosporine is however, only moderately affected by the loss of ATIA (FIG. 6B). These results further support our conclusion that ATIA protects cells against TNF-induced apoptosis. We then examined JNK and NF-KB activation induced by TNF and found that the loss of ATIA has no affect on TNF-induced activation of either of these two pathways (data not shown). These results suggested ATIA has no detectable effect on the immediate downstream signaling by TNF, however, it protects from cell death induced by INF.

Example 3

ATIA Inhibits TGF-beta (TGFB) Signaling

It has been reported that the human homolog of ATIA, Vasorin, is a TGFB-binding protein and modulates the arterial response to injury (24). To test whether ATIA has a similar function in regulating TGFB signaling, TGFB-induced Smad2 activation in wild-type and ATIA−/− MEFs was examined. As shown in FIG. 7, TGF-beta-induced phosphorylation of Smad2 is dramatically increased in ATIA−/− MEFs comparing to what in wild-type cells. This inhibitory effect of ATIA seems to be TGFB signaling specific since loss of ATIA does not alter BMP4-induced activation of Smad1 (FIG. 7, right panel). Therefore, ATIA attenuates TGFB-induced activation of Smad2.

Taken together, the studies discussed above suggest that ATIA not only regulates TGFB signalling, but also protects cells against TNF-induced apoptosis. Since the mitochondrially localized ATIA mutant is sufficient to protect cells against TNF-induced apoptosis, and regulating TGFB signaling by ATIA likely occurs at the plasma membrane, it is conceivable that there is more than one distinct function for the ATIA protein, and that the cellular localization of ATIA is a key factor that determines how ATIA is functioning in the cell.

To test the hypothesis that the plasma membrane form of ATIA is responsible for regulating TGFP signaling while the mitochondrial ATIA protects cells against TNF-induced apoptosis, the ATIA protein will be characterized in order to identify the factors that determine ATIA localization, and this knowledge will be used to show that ATIA location is an important factor in determining its distinct functions. To further understand the regulation of TNF-induced apoptosis, the underlying mechanism of the ATIA protective effect against TNF-induced apoptosis will be examined further. Since ATIA attenuates TGFB signaling, which is known as a tumor suppressor pathway in early carcinogenesis, and ATIA protects cell against apoptosis, ATIA is likely to be involved in promoting tumorigenesis.

Example 4

Plasma Membrane ATIA Regulates TGFB Signaling and Mitochondrial ATIA Protects Cells Against TNF-induced Apoptosis The ATIA protein will be characterized to identify the key factors that determine ATIA cellular locations. This knowledge can be used to address whether the localization of ATIA affects its different functions. For instance, based on the cellular localization of ATIA, different ATIA variant/mutant clones are generated whose products will specifically localize to the plasma membrane or in the mitochondria. The plasma membrane targeted ATIA mutant can be tested for its ability to attenuate TGFB signaling, its ability or failure to protect cells against TNF-induced apoptosis in ATIA−/− MEFs or, in contrast, if the mitochondrial ATIA variant only protects cells against TNF-induced apoptosis, but has no effect on TGFB signaling.

The results discussed herein suggest that the 100 Kd endogenous ATIA membrane protein (memATIA) localizes in plasma membrane and the 80 Kd ATIA (mitoATIA) localizes in the mitochondria. Accordingly, finding out the differences of these two forms of the ATIA protein will help to understand what determines the different cellular localizations of ATIA. It has been examined whether glycosylation causes the size difference of these two ATIA products since the predicted molecular weight of the ATIA protein without signal peptide is only about 70 Kd. As shown in FIG. 8, deglycosylation decreases the molecular weights of both forms of ATIA proteins. The results showed that the mitoATIA is only N-glycosylated while memATIA has both N- and O-glycosylation. After complete deglycosylation, the memATIA protein is about 85 Kd and the mitoATIA is about 70 Kd. Accordingly, these results suggest that glycosylation contributes to the difference of the molecular weights of these two ATIA proteins, but is not the sole factor. There are two possibilities that could be accountable for the remaining difference between memATIA and mitoATIA: 1) memATIA, but not mitoATIA has some additional modifications; 2) an additional proteolysis processing happens to the mitoATIA protein after its signal peptide is removed. For the later case, it is most likely that the additional processing of the ATIA protein happens at its N-terminal since the two products of our c-terminal YFP tagged ATIA plasmid have the similar difference in their molecular weights as the endogenous counterparts do (FIGS. 3 & 4). Therefore, N-terminal protein sequencing and mass spectrometry analysis will be performed on these two forms of ATIA proteins.

Accordingly, the ATIA cDNA has been cloned into the V5 vector, which has a c-terminal His tag. Transient transfection experiments have confirmed that the ATIA-His protein, as the ATIA-YFP protein, is also present in two forms (data not shown, FIG. 3). After establishing a stable ATIA-His overexpression cell line with wt MEF cells, enough ATIA-His protein will be isolated, both memATIA-His and mitoATIA-His, for N-terminal protein sequencing and mass spectrometry analysis. Based on the information from N-terminal protein sequencing and mass spectrometry analysis, a variety of variant/mutant ATIA-YFP clones were created for testing to see if any of these ATIA-YFP proteins exclusively localizes to the mitochondria. If one of those ATIA-YFP proteins does localize to mitochondria specifically, the ATIA-YFP clone will be transfected into ATIA−/− cells for testing.

The results described herein have demonstrated that mitochondrially localized ATIA mutant is capable of protecting cells from TNF-induced apoptosis; however, the results do not completely rule out the possibility that mitochondrial ATIA has no effect on TGFB signaling since ATIAc does not have the LRR domain, which is required for binding to TGFB. We anticipate that the proposed study in the above section will address the issue whether the mitoATIA protects cells against TNF-induced apoptosis, but does not inhibit TGFB signaling.

To generate an ATIA mutant targeted to the plasma membrane, the mitochondrial localization targeting signal (domain) of ATIA will be identified and mutated. Based on previous studies with ATIAc, it is known that the mitochondria-targeting sequence is within 232-673 a.a of ATIA. Therefore, a serial deletion of ATIAc-YFP protein will be performed to examine which region of ATIA is responsible for its mitochondrial localization. Because it is known that mitochondrial targeting sequences normally have conserved arginine residues, different arginine residues will be mutated within the identified region of the full length ATIA by point mutations, and whether certain mutations on those arginine residues will abolish the mitochondrial localization of ATIA, but have no effect on its localization to the plasma membrane will be tested. Based on those results, those mutant ATIA constructs will be used to examine whether the plasma membrane localized ATIA only inhibits TGFβ signaling, but does not protect cells against TNF-induced apoptosis in ATIA−/− MEFs. Though it is known that TGFB can cause cells to undergo growth arrest and apoptosis in certain types of cells, it is not expected that attenuating TGFB signaling by memATIA will have any dramatic effect on TNF-induced apoptosis in MEF cells in the presence of protein synthesis inhibitor, CHX, as this blocks the de novo protein synthesis required for TGFB functions.

Example 5

Figure 9:
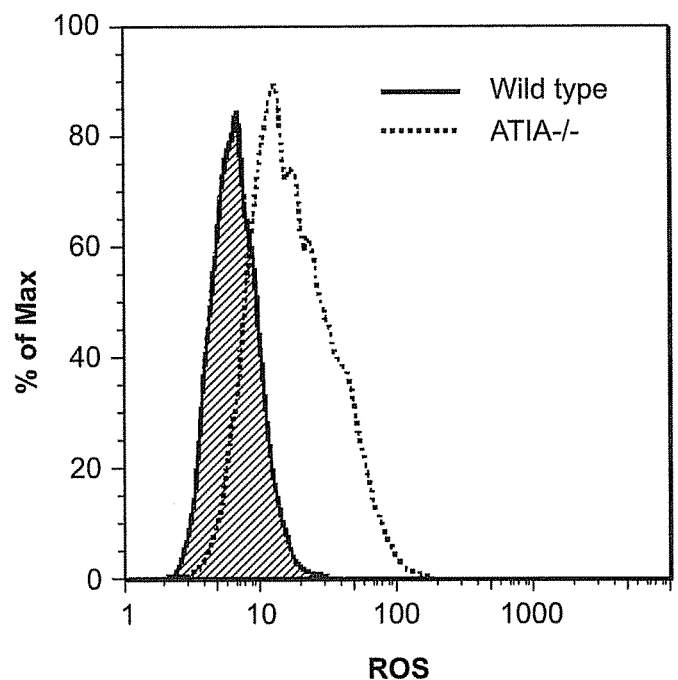
FIG. 9 is a graph that shows reactive oxygen species (ROS) generation is elevated in TIA−/− MEFs.

Atia Protects Cells Against Tnf-induced a Apoptosis Through Regulating TRX2 Function Based on the experiments described herein, it is thought that ATIA plays a role in protecting cells against TNF-induced apoptosis in MEF cells. To further investigate the mechanism of ATIA mediated protection against TNF-induced apoptosis, ATIA interacting proteins are identified. A yeast two-hybrid screen of a mouse liver cDNA library was carried out with the full length ATIA as the bait. After two rounds of screening, an interacting protein was identified called Thioredoxin 2 (TRX2). Interestingly, it has been shown that TRX2 is specifically expressed in the mitochondria and essential for cell survival (28, 29). Deletion of TRX2 causes massive apoptosis, accumulation of intracellular ROS and early embryonic lethality in homozygous mice (30). Therefore, the identification of TRX2 as a potential ATIA-interacting protein raised the possibility that ATIA protects cells against TNF-induced apoptosis through regulating the activity of TRX2. This possibility is supported by the finding that the intracellular ROS level is elevated in ATIA−/− cells comparing to wild type MEFs (FIG. 9).

After confirming the interaction between ATIA and TRX2 in yeast under different stringencies, the ATIA and TRX2 interaction will be examined in the mammalian systems. First the ATIA protein will be tested for the ability to be pulled down by GST-TRX2 fusion protein in vitro. ATIA will be overexpressed along with some of its mutants in MEF cells and the cell lysates will be collected. GST pull-down experiments will be carried out by mixing different cell lysates with GST-TRX2 fusion protein while the GST protein will be used as a control. If an interaction between ATIA and TRX2 is detected with the in vitro pull-down experiments, the ATIA/TRX2 interaction can also be demonstrated by immuno-precipitating endogenous proteins with anti-ATIA and/or TRX2 antibodies. In these experiments, mitochondrial fractions will be isolated to enrich the concentration of mitoATIA in order to limit the interference by the memATIA. In the case that ATIA and TRX2 are loosely associated within mitochondria and can not be detected under regular immuno-precipitation experimental conditions, the cells will betreated with the cross-linking reagent, DSP [Dithiobis(succinimidylpropionate)] after isolation of mitochondria (31). DSP covalently links the proteins in the same complex together and allows us to detect the presence of those proteins that are loosely associated. The cross-linker could be cleaved with 5%13-mercaptoethanol in SDS-PAGE sample buffer at 100° C. for 5 minutes before immuno-precipitants are applied to SDS-PAGE gel.

Next the potential regulatory effect of ATIA on TRX2 function will be examined. It is known that TRX2 is a major player in scavenging ROS generated in mitochondria (28). Particularly, it has been shown that TRX2 is specifically oxidized in response to extra cellular stimuli such as TNF and H202, and the redox state of TRX2 reflects the regulation of TRX2 function (32). Since we found that the intracellular ROS level is elevated in ATIA−/− cells compared to wild type MEFs (FIG. 9), it is possible that the function of TRX2 is deregulated in ATIA−/− MEFs. It has been confirmed that the deletion of ATIA does not affect the expression of TRX2 in ATIA−/− cells (data not shown). Therefore, it is important to examine the redox state of TRX2 in ATIA−/− cells with/without TNF or H202 treatment when compared to wild-type cells. The redox state of TRX2 will be determined by the redox Western analysis with 4-acet-amido-4'-maleimidylstibene-2,2'-disulfonic acid as described previously (32). Meanwhile, the enzymatic activity of TRX2 isolated from wild-type and ATIA−/− cells in vitro will be measured (33). Based on the findings that ATIA−/− mice and MEFs are more sensitive to TNF-induced toxicity/apoptosis and that the intracellular ROS level is elevated in ATIA−/− MEFs, it is anticipated that the level of the oxidized ATIA protein will be higher in ATIA−/− MEFs than in wild-type cells. If it is found that TRX2 function is deregulated in ATIA-/- MEFs, the role of ATIA in this process will be further confirmed by restoring the expression of ATIA in ATIA-/- MEFs and examining whether TRX2 function is reconstituted. Particularly, the region of ATIA that is responsible for interacting with TRX2 will be identified, and then subsequently experiments will be carried out to test whether the ATIA mutant lacking the ability to interact with TRX2 is able to restore the TRX2 function and to protect cells against TNF-induced apoptosis. If the mutant ATIA fails to protect cells, the possible underlying mechanism by which ATIA regulates the function of the mitochondrial TRX system will be investigated.

It has been reported that the TRX system in mitochondria has three major components: the mitochondrial peroxiredoxin III, TRX2 and TRXR2 (28). Therefore, one possibility is that ATIA functions as a scaffold protein to mediate the formation of the mitochondrial TRX complex. To test this hypothesis, the interaction between TRX2 and TRXR2 or between TRX2 and peroxiredoxin III in wild-type and ATIA-/- MEFs will be examined. If there is a defect in the interaction between some of these proteins, it will then be tested whether the affected interaction could be restored by ectopic expression of ATIA in ATIA-/- MEFs. If the absence of ATIA does not affect the interactions among these proteins, the role of ATIA in this system may be to maintain the proper tertiary conformation of the TRX complex required for its normal function. The function of ATIA will be examined by expressing different ATIA mutants in wild-type and ATIA-/- MEFs. It is expected that some ATIA mutants will be identified that restore the function of TRX2 in ATIA-/- MEFs and some mutants that disrupt the normal function of TRX2 in wild-type cells. These studies will aid in understanding how ATIA regulates TRX2 function.

Taken together, the experiments described herein will examine whether ATIA protects cells against TNF-induced apoptosis through regulating TRX2 function.

Example 6

The Role of ATIA in Tumorigenesis

The studies herein suggest that that ATIA is a multifunctional protein: it inhibits TGFB signaling and protects cells against TNF-induced apoptosis. Since TGFB signaling is a known tumor suppressor pathway and apoptosis plays a critical role in preventing tumor development, ATIA may have a role in tumorigenesis by blocking these two tumor suppressing pathways.

Figure 10:
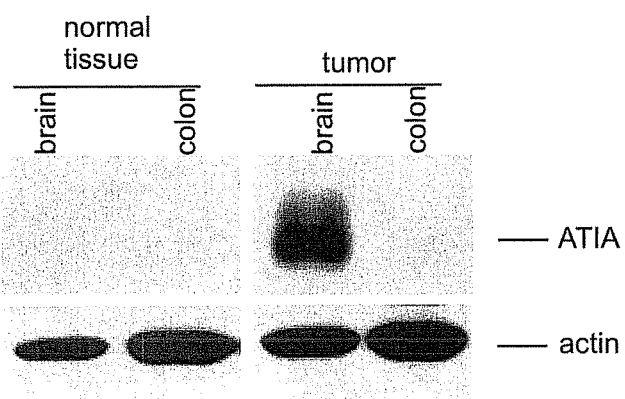
FIG. 10 shows the results of Western Blot showing that ATIA protein is highly expressed in brain tumor.
Figure 11:
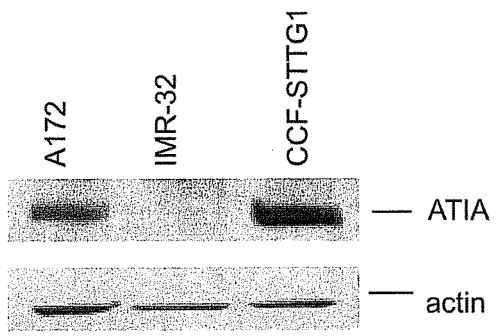
FIG. 11 shows the results of Western Blot showing that ATIA protein expression in brain tumor cell lines.

To explore this possibility, first the levels of ATIA protein in several types of cancers and normal tissues were examined using Western Blots purchased from ProSci Inc. As shown in FIG. 10, ATIA protein level is considerably increased in brain tumors. ATIA protein levels were examined in several human brain tumor cell lines including A-172 (glioblastoma) and CCF-STTG 1 (astrocytoma) and found that A-172 and CCF cells have high ATIA expression (FIG. 11).

Experiments will next examine whether ATIA plays a role in tumorigenesis in mouse models of human tumor. There are several existing mouse models of human brain tumor, such as the activated Ras transgenic mouse model and the NF1 and p53 double knockout mouse model (34, 35). Activation of Ras signaling is critical in both models (34, 36). One of the reasons to choose these two mouse models is that ATIA is highly expressed in the human glioblastoma cell line, A-172 and the astrocytoma cell line, CCF-STTG1, but not in the neuroblastoma cell line, IMR-32 (FIG. 11) and that astrocytoma is developed in these two mouse models. First experiments will test whether ATIA protein level is elevated in the tumors developed in these two models. If ATIA protein is increased in the tumors from one of these two models, for instance, in the Ras transgenic mouse model, experiments will examine the role of ATIA in the tumor development in this model by generating the Ras/ATIA-/- mice through crossing the ATIA-/- mouse with the Ras transgenic mouse. If ATIA tumor development is decreased in Ras/ATIA-/- mice, ATIA may play an important role in tumorigenesis in the Ras transgenic mouse model. This Ras transgenic mouse tumor model would then be employed for a future study on the role of ATIA in tumor promotion or growth. In particular, experiments will focus on whether ATIA contributes to the tumor development in this mouse model through inhibiting TNFB signaling and/or blocking apoptosis.

If there is a failure to detect any increase of ATIA expression in both mouse models, it suggests that the deregulation of ATIA is not involved in the activated Ras-mediated tumorigenesis of brain tumors. If ATIA level is increased in these models, but deletion of ATIA has no effect on the tumor development, it implies that ATIA function is not essential for tumorigenesis in these models. In either case, the potential role of ATIA in tumor development will be addressed by generating an ATIA transgenic mouse model. With ATIA transgenic mice, experiments will address 1) if the elevated expression of ATIA will lead to the development of any type of tumor; 2) whether the increased expression of ATIA protein will promote any tumor development in the presence of carcinogens or mutations of tumor suppressors, for instance in the p537-background.

The experiments described herein will provide insights about the potential role of ATIA in tumorigenesis and establish a system to study the involvement of ATIA in the development of certain types of tumors, and help to identify ATIA as a therapeutic target in treating cancer.

Example 7

Increased Expression of ATIA in Glioblastoma

Figure 12:
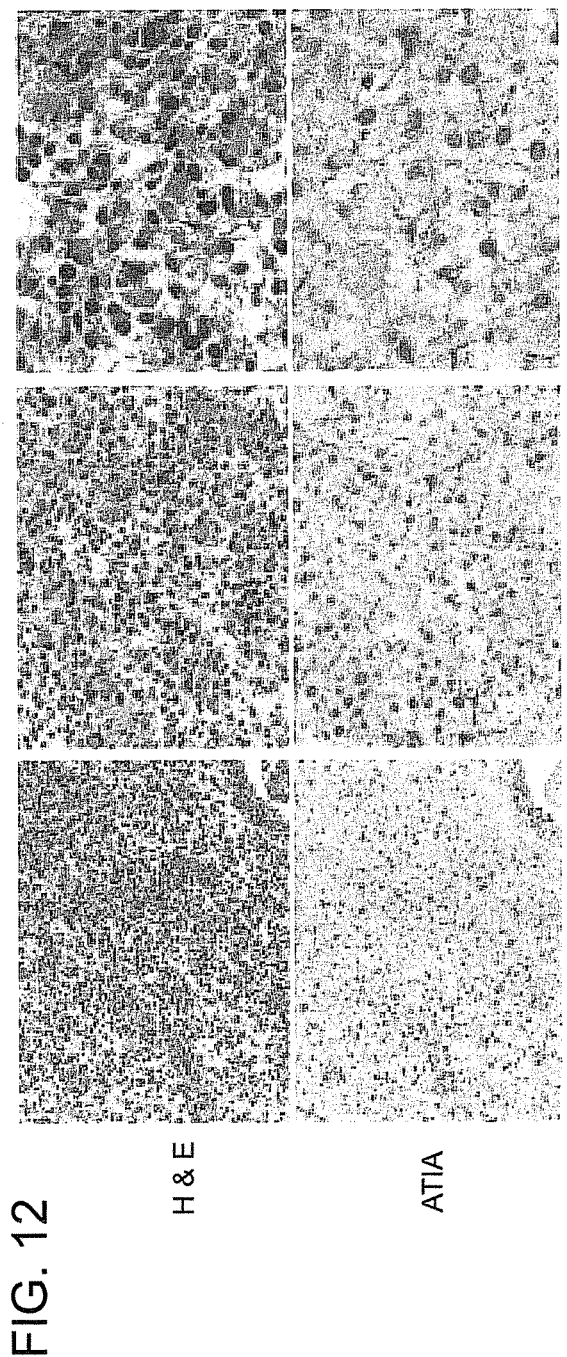
FIG. 12 shows a panel of human glioblastoma tissue stained with anti-ATIA antibody.

Experiments were directed at the expression of ATIA in human brain tumors. The presence of ATIA in human glioblastoma was determined using human glioblastoma tissue stained with anti-ATIA antibody. Samples were obtained from MD Anderson cancer center. As shown in FIG. 12, three of four samples are positive for ant-ATIA staining.

Figure 13:
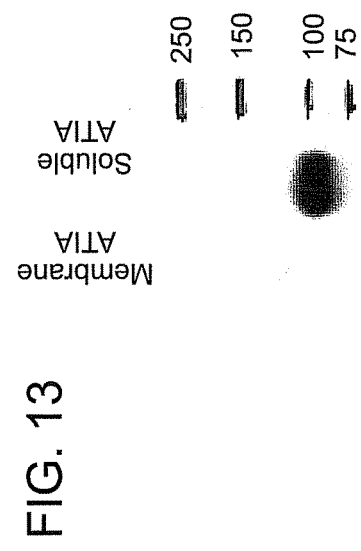
FIG. 13 shows that the soluble form of ATIA is present in the culture medium from A172 glioblastoma cells. The results shows are from a Western blot assay.

FIG. 13 shows that the soluble form of ATIA is present in the cell culture medium from different types of ATIA expressing cells including human glioblastoma A172 cells. In FIG. 13, membrane ATIA is detected from 30 µg total cell lysate and soluble ATIA was concentrated from 1 ml A172 cell culture medium.

Next, human tissue arrays were used to examine the expression of ATIA in glioblastoma and astrocytoma. FIGS. 14-18 show results of tissue array experiments. The tissue arrays were purchased from Biomax US and two types of arrays have been tested for the specific expression of ATIA in human glioblastoma and astrocytoma. All of the experiments were repeated three times with identical results. The glioblastoma array (BS17081) used duplicated cores per case, with 30 cases of brain glioblastoma in three adjacent normal tissues. The multiple brain cancer and adjacent normal tissue array 9GL1001 used 100 cases/100 cores.

Figure 14:
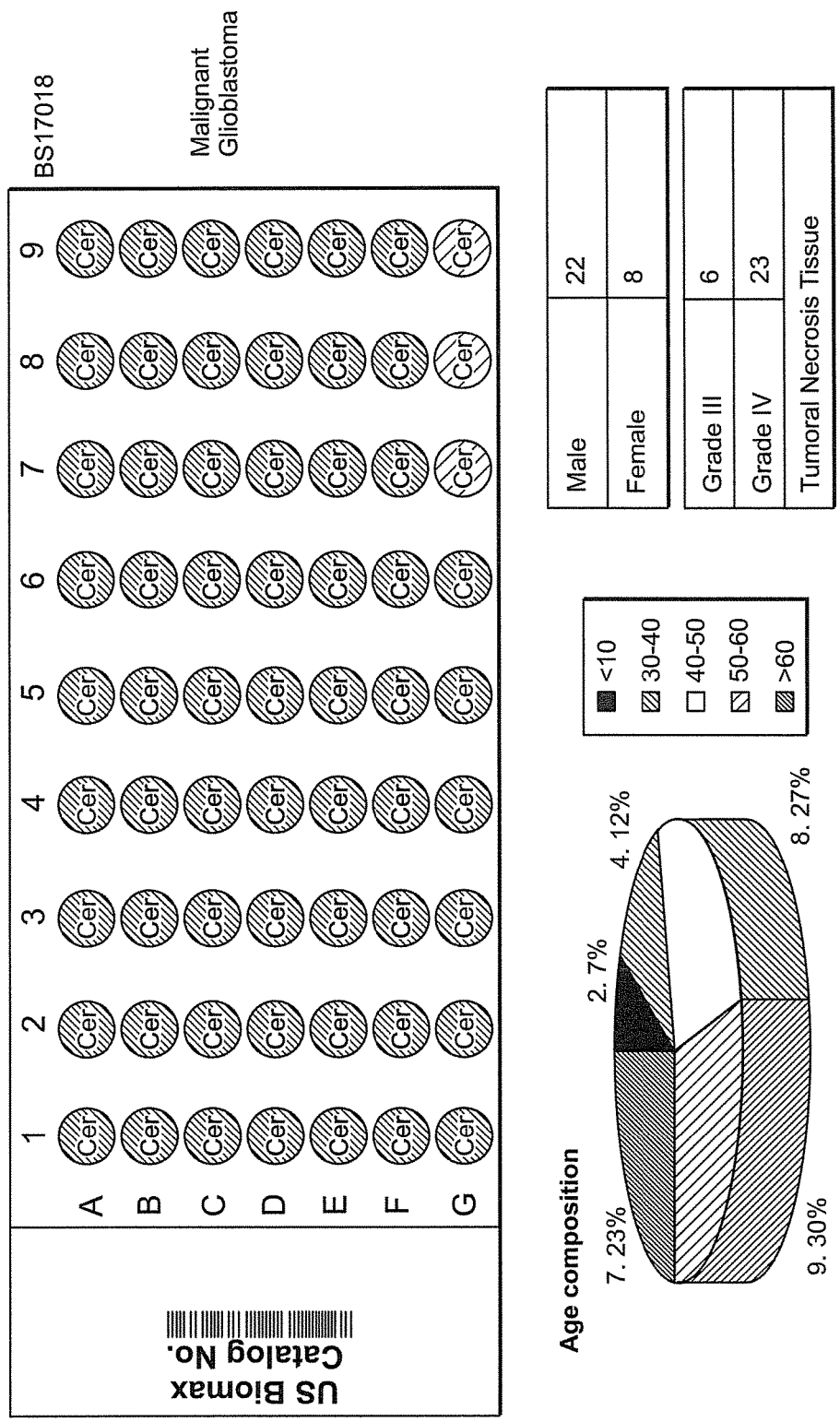
FIG. 14 shows results from the tissue array.
Figure 17:
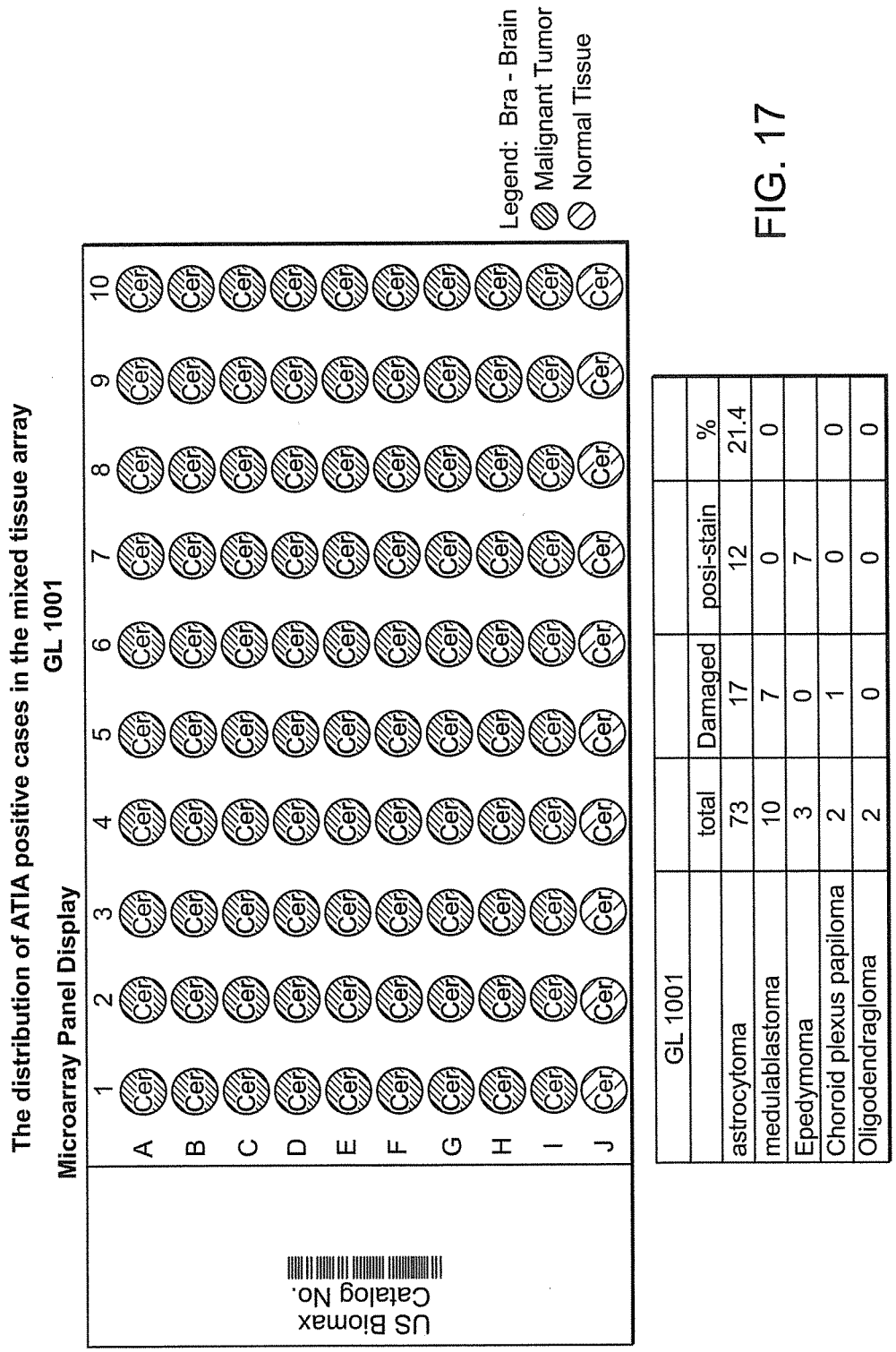
FIG. 17 shows the distribution of ATIA positive cases in the mixed tissue array.

As shown in FIG. 14, 23 cases out of 30 total cases (76.7%) are detected for high ATIA expression in both cores. FIG. 15 is a Table showing the distribution of ATIA positive cases in the glioblastoma array. FIG. 16 shows some examples of immunohistochemistry with antivasorin staining from the glioblastoma tissue arrays. Samples of glioblastoma stage IV were compared with adjacent normal brain tissue. Specimens were examined at 10× and 20×. As shown in FIG. 16, the glioblastoma samples show higher staining than the controls. In FIG. 17, the distribution of ATIA positive cases in the mixed tissue array was examined. As shown in FIG. 17, only some astrocytoma cases are positive by anti-vasorin staining.

Figure 18:
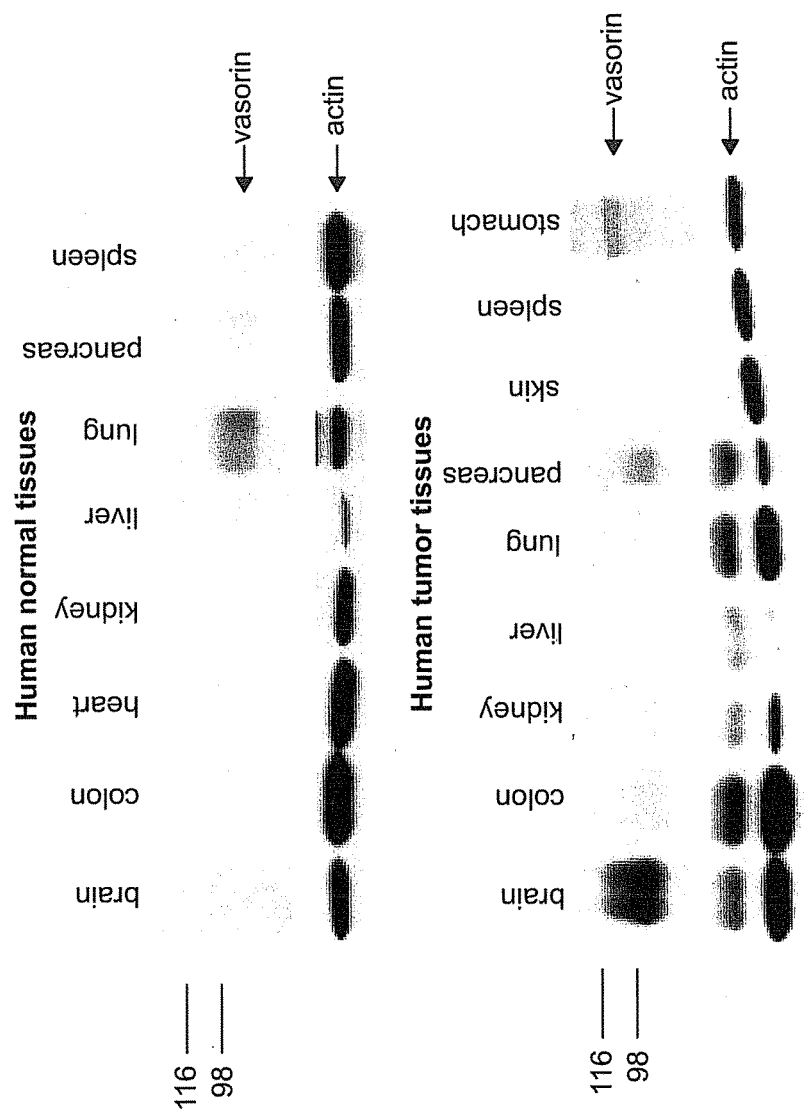
FIG. 18 shows the western results of human tissue blots. The top panel shows the results of vasorin protein detection in human normal tissues. The bottome panel shows the results of human vasorin protein detection in human tumor tissues.

FIG. 18 shows results from human tissue blots with multiple different tissues. The human tissue blots were purchased from ProSci Inc. The tissue blots provided by ProSci Inc. do not have perfectly matched normal vs. tumor blots. ATIA expression (human vasorin) can be seen in human normal tissues in the lung, and in human tumor tissues highly expressed in the brain, and low levels of expression in the pancreas and stomach.

Example 8

Sensitivity of ATIA Expressing Cells to TRAIL-induced Cell Death

Next, the sensitivity of ATIA expressing cells to TRAIL-induced cell death was examined. FIG. 19, left panel, is a western blot showing the expression of ATIA in various glioblastoma cell types. The graph in the right panel of FIG. 19 shows the three glioblastoma cell types that are treated with TRAIL (20 ng/ml) for 24 h. The results show percent viable cells after 24 h.

Example 9

Knockdown of ATIA Makes Cells More Sensitive to Therapy

Figure 21:
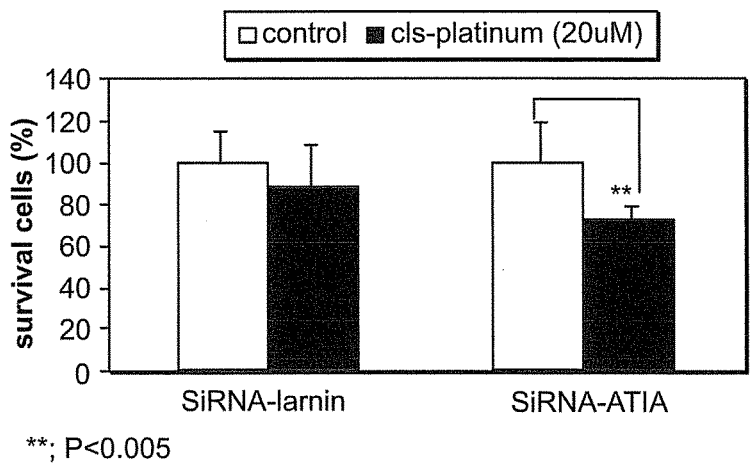
FIG. 21 is a graph that shows knocking down ATIA expressing renders cells sensitive to cisplatinum treatment. The graph shows percent survival of cells.

Experiments were performed that show that knocking down of ATIA expression in human glioblastoma cells renders the cells more sensitive to chemotherapeutic agents. FIG. 15 shows the results of experiments where knocking down of ATIA expression in A172 glioblastoma cells renders the cells sensitive to etoposide or cisplatinum treatment. Both etoposide and cisplatinum cross the blood brain barrier. The top panel of FIG. 20 is a Western Blot showing ATIA expression after siRNA knockdown. A commercial siRNA pool (small RNAs) was used to knockdown ATIA. The bottom panel is a graph that shows cell survival as determined by a MTT assay that measures cell proliferation and viability. The results show that ATIA was partially knocked down in these experiments when these cells are treated with etoposide or cisplatinum. Next, it was tested whether knocking down of ATIA expression in A172 cells renders the cells sensitive to etoposide or cisplatinum treatment. FIG. 21 is a graph that shows that cells where ATIA is knocked down (compared with lamin control siRNA) are rendered sensitive to cisplatinum treatment. There is a significant difference between cisplatinum treatment and control treatment in A172 cells that have decreased ATIA expression.

Example 10

Effect Of ATIA Localization on TNF-induced Apoptpsis

Figure 22A:
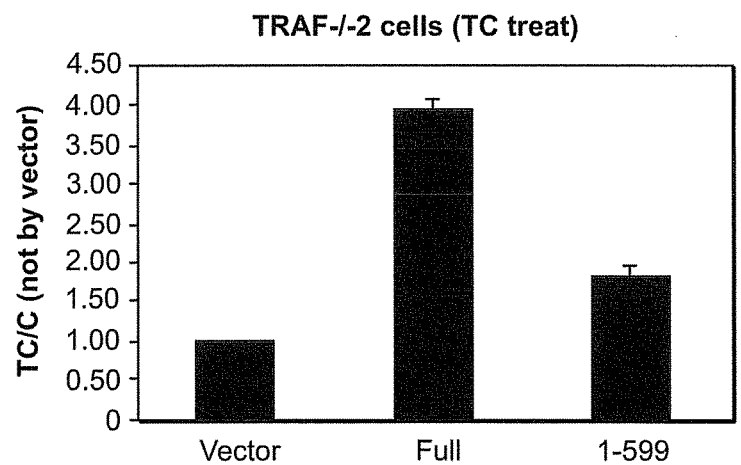
FIG. 22 (A and B) are graphs. (A) shows the 1-599 ATIA mutant, which lost its mitochondrial localization, does not protect cells against TNF-induced apoptosis. (B) shows the mitochondrial localized 232-637 ATIA mutant protects cells against TNF-induced apoptosis.
Figure 22B:
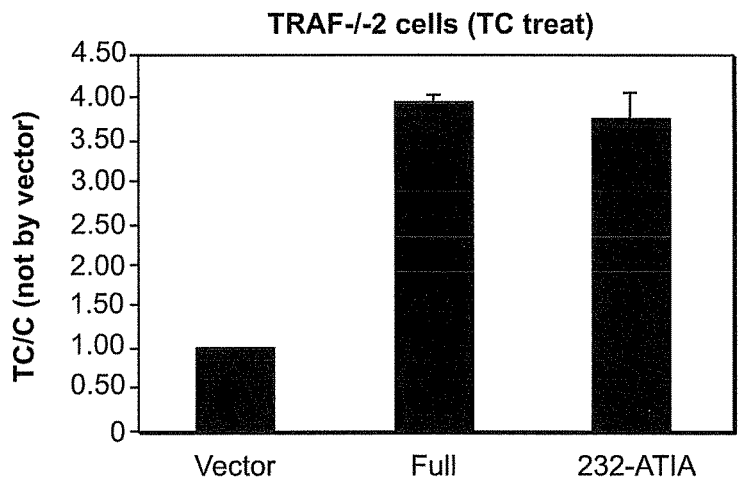

In a further set of experiments shown in FIG. 22 and B, two ATIA mutants were used, 1-599 ATIA and 232-671 ATIA. As shown in FIG. 22A, the 1-599 ATIA mutant, which lost the mitochondrial localization, but still localizes to the cell membrane, does not protect cells against TNF-induced apoptosis. As shown in FIG. 22B, the 232-671 mutant, which only localizes to the mitochondrial, protects cells against apoptosis.

Example 11

ATIA Expression is Increased Under Hypoxic Conditions

Figure 23:
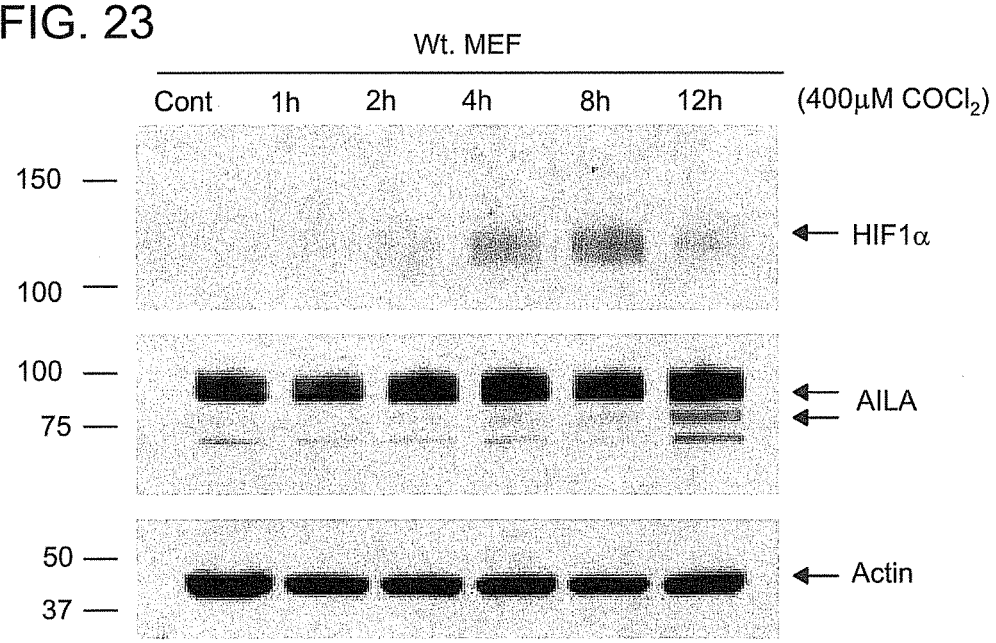
FIG. 23 shows that ATIA is induced following $CoCl_2$ treatment.
Figure 24:
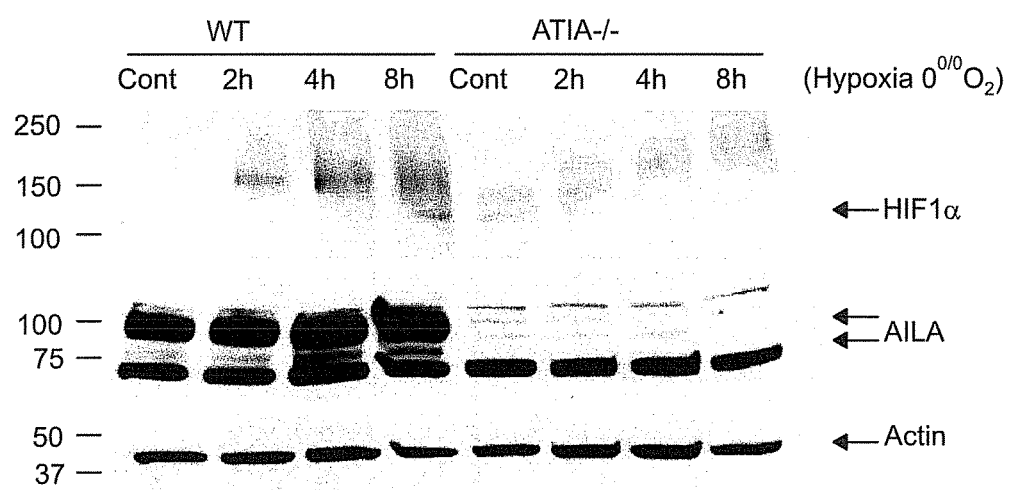
FIG. 24 is a Western blot that shows ATIA is induced under hypoxia conditions.

In a further set of experiments, it was shown that ATIA is a hypoxia-inducible gene. FIG. 23 shows that ATIA is induced following $CoCl_2$ treatment. In FIG. 23, $CoCl_2$ is a hypoxia mimic, which induced hypoxia in treated cells. ATIA protein expression, particularly in the lower band (the mitochondrial ATIA), is considerably increased. Hypoxia-Inducible Factor (HIF)-I is a dimeric protein complex that plays an integral role in the body's response to hypoxia. HIF-I is a major regulator of oxygen homeostasis within cells. As a transcription factor, it affects and regulates the expression of dozens of genes involved in maintaining homeostasis as oxygen concentrations change ATIA promoter has two HIF responsive sites. FIG. 24 is a Western blot that shows ATIA is induced under hypoxia conditions.

Example 12

Knocking Down ATIA Sensitizes Cells to Hypoxic Conditions

Figure 25:
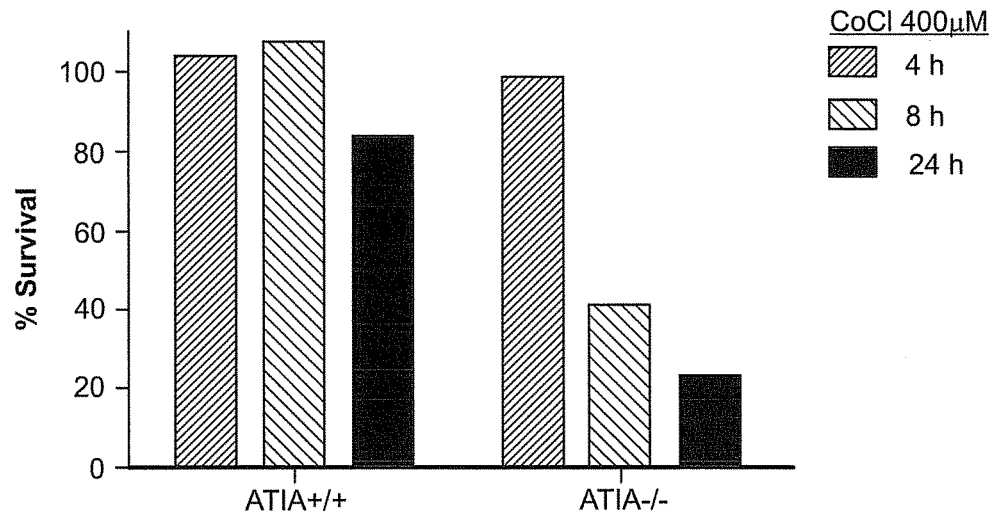
FIG. 25 is a graph that shows increased sensitivity to $CoCl_2$ induced Hypoxia in ATIA KO MEFs. Wt and ATIA−/− MEFs are treated with $CoCl_2$ and cell death is detected at different time points as indicated in the figure. ATIA−/− MEFs are much more sensitive to $CoCl_2$ -induced cell death.
Figure 26:
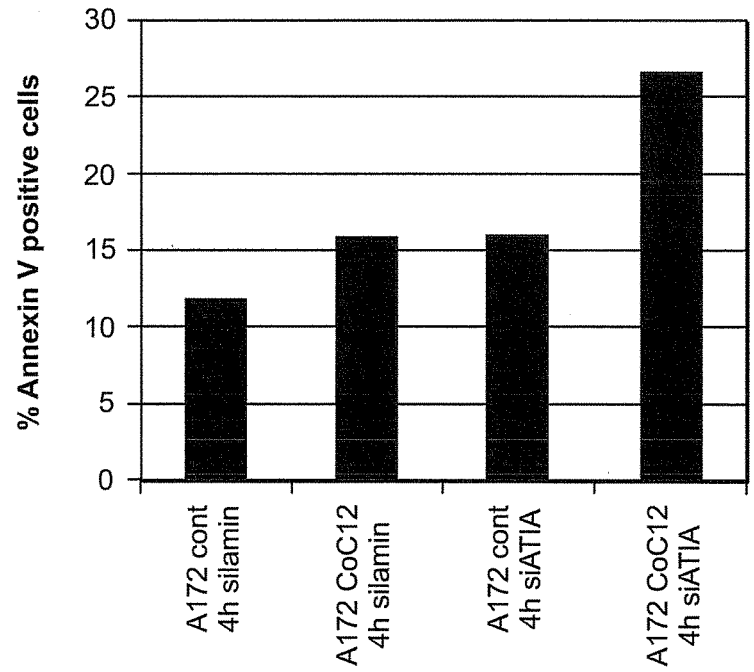
FIG. 26 is a graph that shows increased sensitivity of A172 cells to $CoCl_2$ treatment when ATIA is knocked down. Human glioblastoma A172 cells are transfected with siRNAs of lamin or ATIA and then treated with $CoCl_2$. ATIA knock down renders cells more sensitive to $CoCl_2$ induced cell death.
Figure 27:
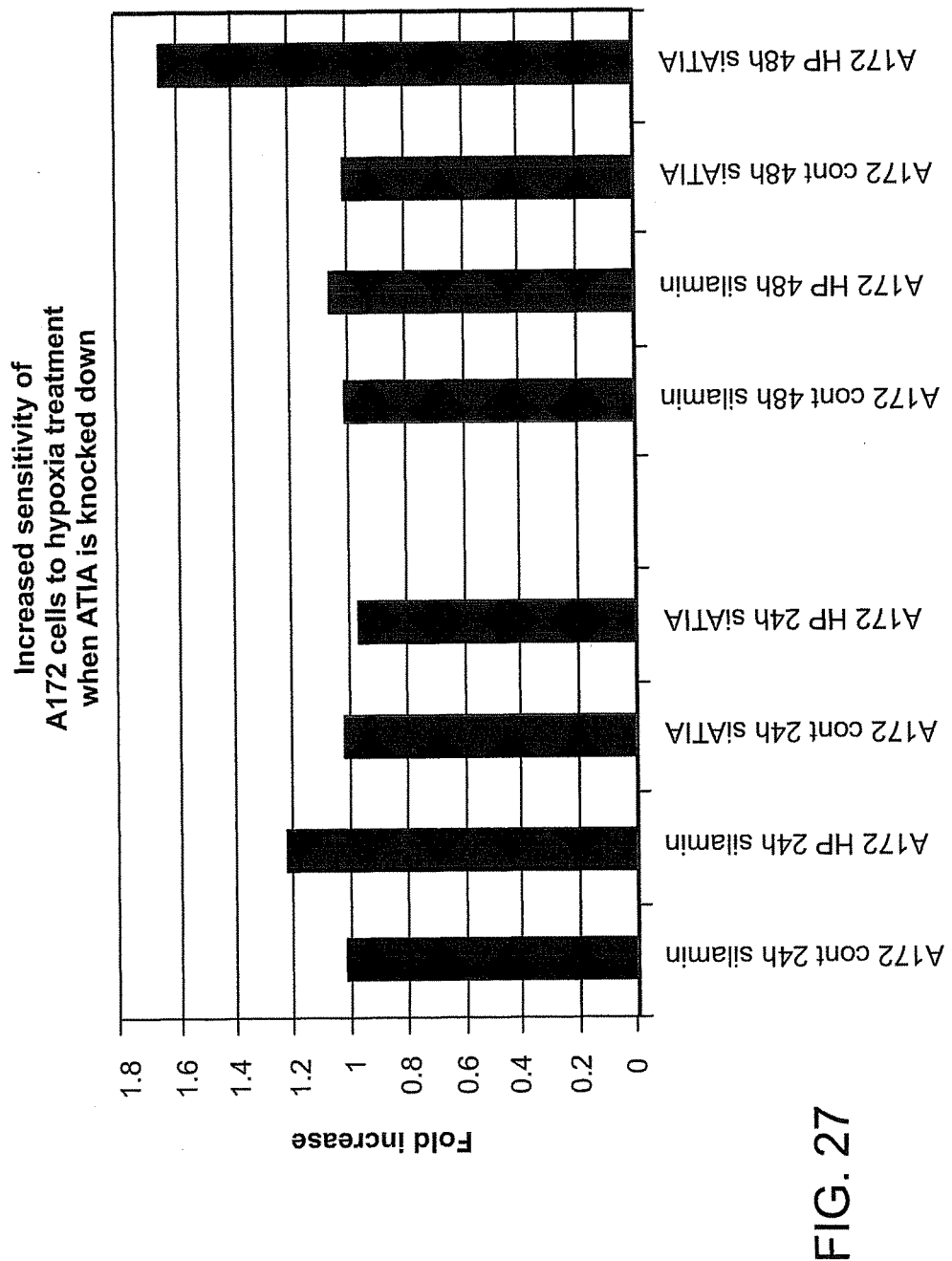
FIG. 27 is a graph that shows increased sensitivity of A172 cells to hypoxia treatment when ATIA is knocked down. A172 cells were transfected with siRNA targeting lamin or ATIA for o/n, cells were then subjected to 24 h and 48 h of hypoxia (0% Oxygen). Cell death was determined using Annexin V/PI staining method and analyzed using flow cytometry.

FIG. 25 is a graph that shows increased sensitivity to $CoCl_2$ induced Hypoxia in ATIA KO MEFs. In these experiments, wild type (Wt) and ATIA knockout (ATIA−/−) MEFs are treated with $CoCl_2$ and cell death is detected at different time points as indicated in the figure. The results shown in FIG. 25 demonstrate that ATIA−/− MEFs are much more sensitive to $CoCl_2$-induced cell death. Further, FIG. 26 is a graph that shows increased sensitivity of A172 glioblastoma cells to $CoCl_2$ treatment when ATIA is knocked down. Human glioblastoma A172 cells are transfected with siRNAs of lamin or ATIA and then treated with $CoCl_2$. ATIA knock down renders cells more sensitive to $CoCl_2$ induced cell death. As shown in FIG. 27, A172 cells were transfected with siRNA targeting lamin or ATIA for o/n, and were then subjected to 24h and 48h of hypoxia (0% Oxygen). Cell death was determined using Annexin V/PI staining method and analyzed using flow cytometry. These results show increased sensitivity of A172 cells to hypoxia treatment when ATIA is knocked down. Accordingly, these findings demonstrate that ATIA is important for cancer cells to survive through protecting hypoxia-induced cell death.

Example 13

Treatment with Small Chemical Molecules Reduces ATIA in Cancer Cells

Figure 28:
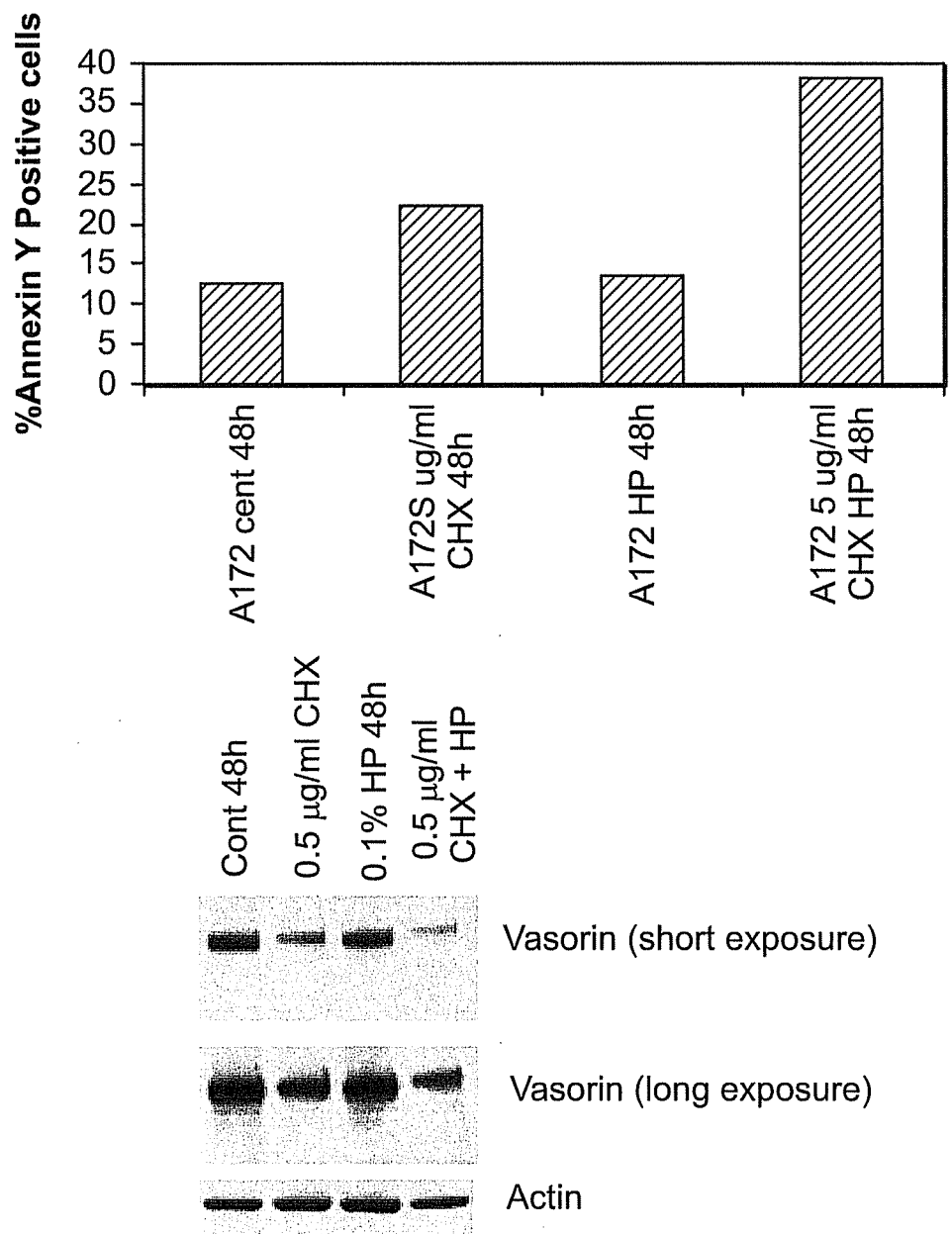
FIG. 28 is two panels that show the effect of cyclohexamide on ATIA stability and cell apoptosis. The top panel is a graph that shows the number of annexin positive cells after cyclohexamide treatment. The bottom panel is a blot that shows vasorin expression after cyclohexamide treatment.

Experiments were performed with small chemical molecules to reduce ATIA levels in cancer cells. Examples of small molecules that can be used include, but are not limited to, cyclohexamide. Cyclohexamide, at low levels (e.g. 0.1 μg-1.0 μg) reduces ATIA levels in tumor cells. Preferably, cyclohexamine is administered locally to the tumor. Results of an experiment where tumors are treated with cyclohexamide (0.5 μg) are shown in FIG. 28. FIG. 28 is a graph that shows the effect of cyclohexamide on ATIA stability and cell apoptosis. As shown n FIG. 28, 0.5 ug of cycloheximide causes the decrease of ATIA in A172 Cells. Hypoxia induces A172 cells undergo apoptosis in the presence of CHX.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

The following specific references, also incorporated by reference, are indicated above by corresponding reference number.

1. Tracey, K. J., and Cerami, A. (1993). Tumor necrosis factor, other cytokines and disease. Annu. Rev. Cell Biol. 9, 317-343.
2. Liu, Z-G and Han, J. (2001) Cellular Response to Tumor Necrosis Factor (TNF). Current Issues in Molecular Biology, 3, 79-90.
3. Locksley, R. M., Killeen, N. & Lenardo M. L. The TNF and TNF receptor superfamilies: integrating mammalian biology. Cell 104, 487-501 (2001).
4. Carswell, E. A., Old, L. J., Kassel, R. L., Green, S., Fiore, N., and Williamson, B. (1975). An endotoxin-induced serum factor that causes necrosis of tumors. Proc Natl Acad Sci USA 72, 3666-3670.
5. Sugarman, B. J., Aggarwal, B. B., Hass, P. E., Figari, I. S., Palladino, M. A., and Shepard, H. M. (1985). Recombinant human tumor necrosis factor-alpha: effects on proliferation of normal and transformed cells in vitro. Science 230, 943-5.
6. Beutler, B. and Cerami, A. (1988). Tumor necrosis, cachexia, shock, and inflammation: A common mediator. Ann. Rev. Biochem. 57, 505-518.
7. Tartaglia, L. A., and Goeddel, D. V. (1992). Two TNF receptors. Immunol. Today 13, 151-153.
8. Lewis, M., Tartaglia, L. A., Lee, A., Bennett, G. L., Rice, G. C., Wong, G. H., Chen, E. Y., Goeddel, D. V. (1991). Cloning and expression of cDNAs for two distinct murine tumor necrosis factor receptors demonstrate one receptor is species specific. Proc. Natl. Acad. Sci. USA 88, 2830-2834.
9. Vandenabeele, P., Declercq, W., Beyaert, R., and Fiers, W. (1995). Two tumor necrosis factor receptors: structure and function. Trends Cell Biol. 5, 392-399.
10. Smith, C. A., Farrah, T., and Goodwin, R. G. (1994). The TNF Receptor superfamily of cellular and viral proteins: activation, costimulation and death. Cell 76, 959-962.
11. Liu, Z G. And Han, J. (2001) Cellular responses to Tumor Necrosis Factor (TNF). Current Issues in Molecular Biology 3, 79-90.
12. Baud, V. & Karin, M. Signal transduction by tumor necrosis factor and its relatives. Trends Cell Biol. 11, 372-7 (2001).
13. Chen, G. & Goeddel, D. V. TNF-R1 signaling: a beautiful pathway. Science 296, 1634-1635 (2002).
14. Wajant, H., Pfizenmaier, K. & Scheurich, P. Tumor necrosis factor signaling. Cell Death Differ. 10, 45-65 (2003).
15. Nagata, S, and Golstein P. (1995). The Fas death factor. Science 267, 1449-1456.
16. Nagata, S. (1997) Apoptosis by death factor. Cell 88, 355-365.
17. Ashkenazi, A. and Dixit, V. M. (1998). Death receptors: Signaling and modulation. Science 281, 1305-1308.
18. Van Antwerp, D. J., Martin, S. J., Verma, I. M., and Green, D. R. (1998). Inhibition of TNF-induced apoptosis by NF-KB. Trends Cell Biol 8, 107-111
19. Wang, C. Y., Mayo, M. W., Korneluk, R. G., Goeddel, D. V., and Baldwin, A. S. Jr. (1998). NF-xB antiapoptosis: induction of TRAF1 and TRAF2 and c-IAP1 and c-IAP2 to suppress caspase-8 activation. Science 281, 1680-1683.
20. Wu, M. X., Ao, Z., Prasad, K. V., Wu, R., and Schlossman, S. F. (1998). IEX-1L, an apoptosis inhibitor involved in NF-KB-mediated cell survival. Science 281, 998-1001
21. Kreuz S, Siegmund D, Scheurich P, Wajant H. (2001) NF-kappaB inducers upregulate cFLIP, a cycloheximide-sensitive inhibitor of death receptor signaling. Mol Cell Biol. 21, 3964-73.
22. Yeh, W. C., Shahinian, A., Speiser, D., Kraunus, J., Billia, F., Wakcham, A., de la Pompa J. L., Ferrick, I)., Hum, B., Iscove, N., Ohashi, P., Rothe, M., Goeddel, D. V., and Mak, T. W. (1997). Early lethality, functional NF-kappaB activation, and increased sensitivity to TNF-induced cell death in TRAF2-deficient mice. Immunity 7, 715-25.
23. Lin Y, Ryan J, Lewis J, Wani M A, Lingrel J B, Liu Z G. (2003) TRAF2 exerts its antiapoptotic effect by regulating the expression of Kruppel-like factor LKLF. Mol Cell Biol. 23, 5849-56.
24. Ikeda Y, Imai Y, Kumagai H, Nosaka T, Morikawa Y, Hisaoka T, Manabe I, Maemura K, Nakaoka T, Imamura T, Miyazono K, Komuro I, Nagai R, Kitamura T. (2004) Vasorin, a transforming growth factor beta-binding protein expressed in vascular smooth muscle cells, modulates the arterial response to injury in vivo. Proc Natl Acad Sci 101, 10732-7.
25. Yeh, W. C., Shahinian, A., Speiser, D., Kraunus, J., Billia, F., Wakeharn, A., de la Pompa J. L., Ferrick, D., Hum, B., Iscove, N., Ohashi, P., Rothe, M., Goeddel, D. V., and Mak, T. W. (1997). Early lethality, functional NF-kappaB activation, and increased sensitivity to TNF-induced cell death in TRAF2-deficient mice. Immunity 7, 715-25.
26. Tiegs, G., Wolter, M. & Wendel, A. Tumor necrosis factor is a terminal mediator in galactosamine/endotoxin-induced hepatitis in mice. Biochem. Pharmacol. 38, 627-31 (1989).
27. Decker, K. & Keppler, D. (1974) Galactosamine hepatitis: key role of the nucleotide deficiency period in the pathogenesis of cell injury and cell death. Rev. Physiol. Biochem. Pharmaco. 77-106.
28. Masutani H, Ueda S, Yodoi J. (2005) The thioredoxin system in retroviral infection and apoptosis. Cell Death Differ. 12 Suppl 1, 991-998.
29. Tanaka T, Hosoi F, Yamaguchi-Iwai Y, Nakamura H, Masutani H, Ueda S, Nishiyama A, Takeda S, Wada H, Spyrou G, Yodoi J. (2002) Thioredoxin-2 (TRX-2) is an essential gene regulating mitochondria-dependent apoptosis. EMBO J. 21, 1695-1703.
30. Nonn L, Williams R R, Erickson R P, Powis G. (2003) The absence of mitochondrial thioredoxin 2 causes massive apoptosis, exencephaly, and early embryonic lethality in homozygous mice. Mol Cell Biol. 23, 916-922

31. Liu, H. T., and Yung B. Y. M. (1999) In vivo interaction of nucleophosmin/B23 and protein C23 during cell cycle progression in HeLa cells. Cancer Letters, 144, 45-54.
32. Hansen J M, Zhang H, Jones DP. (2006) Mitochondrial thioredoxin-2 has a key role in determining tumor necrosis factor-alpha-induced reactive oxygen species generation, NF-kappaB activation, and apoptosis. Toxicol Sci. 91, 643-50.
33. Spyrou G, Enmark E, Miranda-Vizuete A, Gustafsson J. (1997) Cloning and expression of a novel mammalian thioredoxin. J. Biol. Chem. 272, 2936-41
34. Ding I T, Roncari L, Shannon P, Wu X, Lau N, Karaskova J, Gutmann D H, Squire J A, Nagy A, Guha A. (2001) Astrocyte-specific expression of activated p21-ras results in malignant astrocytoma formation in a transgenic mouse model of human gliomas. Cancer Res. 61, 3826-36
35. Reilly K M, Loisel D A, Bronson R T, McLaughlin M E, Jacks T. (2000) Nf1; Trp53 mutant mice develop glioblastoma with evidence of strain-specific effects. Nat. Genet. 26,109-13.
36. Cichowski K, Jacks T. (2001) NH tumor suppressor gene function: narrowing the GAP. Cell 104, 593-604.
37. Hsu, H., Xiong, J., and Goeddel, D. V. (1995). The TNF receptor 1-associated protein TRADD signals cell death and NF-B activation. Cell 81, 495-504.
38. Rothe, M., Wong, S. C., Henzel, W. J., and Goeddel, D. V. (1994). A novel family of putative signal transducers associated with the cytoplasmic domain of the 75 kDa tumor necrosis factor receptor. Cell 78, 681-692.
39. Rothe, M., Sarma, V., Dixit, V. M., and Goeddel, D. V. (1995). TRAF2-mediated activation of NF-KB by TNF receptor 2 and CD40. Science 269, 1424-1427.
40. Stanger, B. Z., Leder, P., Lee, T. H., Kim, E., and Seed, B. (1995). RIP: a novel protein containing a death domain that interacts with Fas/APO-1 (CD95) in yeast and causes cell death. Cell 81, 513-523.
41. Ting, A. T., Pimentel-Muinos, F. X., and Seed, B. (1996). RIP mediates tumor necrosis factor receptor 1 activation of NF-KB but not Fas/APO-1-initiated apoptosis. EMBO J. 15, 6189-6196.
42. Siebenlist, U., Franzoso, G., and Brown, K. (1994). Structure, regulation and function of NF-KB. Annu Rev Cell Biol 10, 405-455.
43. Baeuerle, P. A. and Baltimore, D. (1996). NF-KB: ten years after. Cell 87, 13-20.
44. Karin, M., Liu, Z. G., and Zandi, E. (1997). AP-1 function and regulation. Curr. Opin. Cell Biol. 9, 240-246.
45. Hsu, H., Shu, H. B., Pan, M. P., and Goeddel, D. V. (1996a). TRADD-TRAF2 and TRADD-FADD interactions define two distinct TNF receptor-1 signal transduction pathways. Cell 84, 299-308.
46. Hsu, H., Huang, J., Shu, H. B., Baichwal, V., and Goeddel, D. V. (1996b). TNF-dependent recruitment of the protein kinase RIP to the TNF receptor-1 signaling complex. Immunity 4, 387-396.
47. Liu, Z. G, Hsu, H., Goeddel, D. V., and Karin, M. (1996). Dissection of TNF receptor 1 effector functions: JNK activation is not linked to apoptosis while NF-KB activation prevents cell death. Cell 87, 565-576.
48. Boldin, M. P., Varfolomeev, E. E., Pancer, Z., Mett, I. L., Camonis, J. H., and Wallach, D. (1995). A novel protein that interacts with the death domain of Ras/APO1 contains a sequence motif related to the death domain. J. Biol. Chem. 270, 7795-7798.
49. Chinnaiyan, A. M., O'Rourke, K., Tewari, M., and Dixit, V. M. (1995). FADD, a novel death domain-containing protein, interacts with the death domain of Fas and initiates apoptosis. Cell 81, 505-512.
50. Micheau, 0. & Tschopp, J. Induction of TNF receptor I-mediated apoptosis via two sequential signaling complexes. Cell 114, 181-190 (2003).
51. Kelliher, M. A., Grimm, S., Ishida, Y., Kuo, F., Stanger, B. Z., and Leder P. (1998). The death domain kinase RIP mediates the TNF-induced NF-kappaB signal. Immunity 8, 297-303.
52. Zhang, J., D. Cado, A. Chen, N. H. Kabra, and A. Winoto. (1998). Fas-mediated apoptosis and activation-induced T-cell proliferation are defective in mice lacking FADD/Mortl. Nature 392, 296-300.
53. Devin, A. Lin, Y., and Liu, Z G (2003) The role of the death domain kinase RIP in tumor-nerosis-factor-induced activation of mitogen-activated protein kinases. EMBO reports, 4, 623-627.
54. Devin, A., Cook, A., Lin, Y., Rodriguez, Y., Kelliher, M., and Liu, Zg. (2000) The distinct roles of TRAF2 and RIP in IKK activation by TNF-R1: TRAF2 recruits IKK to TNF-R1 while RIP mediates IKK activation. Immunity 12, 419-429
55. Holler, N, Zaru, R., Micheau, 0., Thome, M., Attinger, A., Valitutti, S., Bodmer, J. L., Schneider, P., Seed, B and Tschopp, J. (2000) Fas triggers an alternative, caspase-8-independent cell death pathway using the kinase RIP as effector molecule. Nat. Immunol. 1, 489-95.
56. Lin Y., Choksi S., Shen H. M., Yang Q. F., Hur G. M., Kim Y. S., Tran J. H., Nedospasov S. A. & Liu Z. G (2004) Tumor necrosis factor-induced nonapoptotic cell death requires receptor-interacting protein-mediated cellular reactive oxygen species accumulation. J. Biol. Chem. 279, 10822-10828.
57. Kim, Y., Morgan, M. J., Choksi, S. & Liu, Z. G. (2007) TNF-Induced Activation of the Nox1 NADPH Oxidase and Its Role in the Induction of Necrotic Cell Death. Mol. Cell. 26, 769-771.
58. Jin, Z. & El-Deiry, W. S. (2006) Distinct signaling pathways in TRAIL-versus tumor necrosis factor-induced apoptosis. Mol Cell Biol. 26, 8136-48.
59. Zheng, L., Bidere, N., Staudt, D., Cubre, A., Orenstein, J., Chan, F. K. & Lenardo, M. (2006) Competetive Control of independent programs of tumor necrosis factor-induced cell death by TRADD and RIP1. Mol. Cell. Biol. 26, 3505-3513.
60. Ashkenazi, A., and Dixit, V. M. (1998). Death receptors: signaling and modulation. Science 281, 1305-1308.
61. Wajant, H. (2003). Death receptors. Essays Biochem 39, 53-71.
62. Lavrik, I., Golks, A., and Krammer, P. H. (2005). Death receptor signaling. J Cell Sci 118, 265-267.
63. Peter, M. E. (2000). The TRAIL DISCussion: It is FADD and caspase-8! Cell Death Differ 7, 759-760.
64. Peter, M. E., and Krammer, P. H. (2003). The CD95 (APO-1/Fas) DISC and beyond. Cell Death Differ 10, 26-35.
65. Park, S. M., Schickel, R., and Peter, M. E. (2005). Nonapoptotic functions of FADD-binding death receptors and their signaling molecules. Curr Opin Cell Biol 17, 610-616.
66. Coussens L. M. & Werb Z. (2002). Inflammation and cancer. Nature 420, 860-867.
67. Li Q. & Verma I. M. NFKB regulation in the immune system. (2002). Nat. Rev. Immunol. 2, 725-734.
68. Baldwin A. S. Control of oncogenesis and cancer therapy resistance by the transcription factor NFKB. (2001). J. Clin. Invest. 107, 241-246.

69. Karin M., Cao Y., Greten F. R. & Li Z-W. NFKB in cancer: from innocent bystander to major culprit. (2002). Nat. Rev. Cancer 2, 301-310.
70. Lin A. & Karin M. NFKB in cancer: a marked target. (2003). Semin. Can. Biol. 13, 107-114.
71. Szlosarek P, Charles K A, Balkwill FR. (2006) Tumor necrosis factor-a as a tumor promoter. Eur. J. Cancer 42, 745-750.
72. Iwasaki A. & Medzhitov R. (2004) Toll-like receptor control of the adaptive immune responses. Nat. Immunol. 5, 987-995.
73. Akira S. & Takeda K. (2004) Toll-like receptor signaling. Nat. Rev. Immunol. 4, 499-509.
74. Huang B., Zhao J., Unkeless J. C., Feng Z. H. & Xiong H. (2008) TLR signaling by tumor and immune cells: a double-edged sward. Oncogene 27, 218-224.
75. Bodmer, J. L., Burns, K., Schneider, P., Hofmann, K., Steiner, V., Thome, M., Bornand, T., Hahne, M., Schroter, M., Becker, K., et al. (1997). TRAMP, a novel apoptosis-mediating receptor with sequence homology to tumor necrosis factor receptor 1 and Fas(Apo-1/CD95). Immunity 6, 79-88.
76. Chinnaiyan, A. M., O'Rourke, K., Yu, G. L., Lyons, R. H., Garg, M., Duan, D. R., Xing, L., Gentz, R., Ni, J., and Dixit, V. M. (1996). Signal transduction by DR3, a death domain-containing receptor related to TNFR-1 and CD95. Science 274, 990-992.
77. Kitson, J., Raven, T., Jiang, Y. P., Goeddel, D. V., Giles, K. M., Pun, K. T., Grinham, C. J., Brown, R., and Farrow, S. N. (1996). A death-domain-containing receptor that mediates apoptosis. Nature 384, 372-375.
78. Marsters, S. A., Sheridan, J. P., Donahue, C. J., Pitti, R. M., Gray, C. L., Goddard, A. D., Bauer, K. D., and Ashkenazi, A. (1996). Apo-3, a new member of the tumor necrosis factor receptor family, contains a death domain and activates apoptosis and NF-kappa B. Curr Biol 6, 1669-1676.
79. Screaton, G. R., Xu, X. N., Olsen, A. L., Cowper, A. E., Tan, R., McMichael, A. J., and Bell, J. I. (1997). LARD: a new lymphoid-specific death domain containing receptor regulated by alternative pre-mRNA splicing. Proc Natl Acad Sci USA 94, 4615-4619.
80. Migone, T. S., Zhang, J., Luo, X., Zhuang, L., Chen, C., Hu, B., Hong, J. S., Perry, J. W., Chen, S. F., Zhou, J. X., et al. (2002). TL1A is a TNF-like ligand for DR3 and TR6/DcR3 and functions as a T cell costimulator. Immunity 16, 479-492.
81. Wen, L., Zhuang, L., Luo, X., and Wei, P. (2003). TL1A-induced NF-kappaB activation and c-IAP2 production prevent DR3-mediated apoptosis in TF-1 cells. J Biol Chem 278, 39251-39258.
82. Wang, E. C., Them, A., Denzel, A., Kitson, J., Farrow, S. N., and Owen, M. J. (2001). DR3 regulates negative selection during thymocyte development. Mol Cell Biol 21, 3451-3461.
83. Su, W. B., Chang, Y. H., Lin, W. W., and Hsieh, S. L. (2006). Differential regulation of interleukin-8 gene transcription by death receptor 3 (DR3) and type I TNF receptor (TNFR1). Exp Cell Res 312, 266-277.
84. Papadakis, K. A., Zhu, D., Prehn, J. L., Landers, C., Avanesyan, A., Lafkas, G., and Targan, S. R. (2005). Dominant role for TL1A/DR3 pathway in IL-12 plus IL-18-induced IFN-gamma production by peripheral blood and mucosal CCR9+ T lymphocytes. J Immunol 174, 4985-4990.
85. Derosa, D. C., Ryan, P. J., Okragly, A., Witcher, D. R., and Benschop, R. J. (2008). Tumor-derived death receptor 6 modulates dendritic cell development. Cancer Immunol Immunother 57, 777-787.
86. Pan, G., Bauer, J. H., Haridas, V., Wang, S., Liu, D., Yu, G., Vincenz, C., Aggarwal, B. B., Ni, J., and Dixit, V. M. (1998). Identification and functional characterization of DR6, a novel death domain-containing TNF receptor. FEBS Lett 431, 351-356.
87. Kasof, G. M., Lu, J. J., Liu, D., Speer, B., Mongan, K. N., Gomes, B. C., and Lorenzi, M. V. (2001). Tumor necrosis factor-alpha induces the expression of DR6, a member of the TNF receptor family, through activation of NF-kappaB. Oncogene 20, 7965-7975.
88. Liu, J., Na, S., Glasebrook, A., Fox, N., Solenberg, P. J., Zhang, Q., Song, H. Y., and Yang, D. D. (2001). Enhanced CD4+ T cell proliferation and Th2 cytokine production in DR6-deficient mice. Immunity 15, 23-34.
89. Zhao, H., Yan, M., Wang, H., Erickson, S., Grewal, I. S., and Dixit, V. M. (2001). Impaired c-Jun amino terminal kinase activity and T cell differentiation in death receptor 6-deficient mice. J Exp Med 194, 1441-1448.
90. Schmidt, C. S., Liu, J., Zhang, T., Song, H. Y., Sandusky, G., Mintze, K., Benschop, R. J., Glasebrook, A., Yang, D. D., and Na, S. (2003). Enhanced B cell expansion, survival, and humoral responses by targeting death receptor 6. J Exp Med 197, 51-62.
91. Kischkel, F. C., Lawrence, D. A., Chuntharapai, A., Schow, P., Kim, K. J., and Ashkenazi, A. (2000). Apo2L/TRAIL-dependent recruitment of endogenous FADD and caspase-8 to death receptors 4 and 5. Immunity 12, 611-620.
92. Schneider, P., Thome, M., Burns, K., Bodmer, J. L., Hofmann, K., Kataoka, T., Holler, N., and Tschopp, J. (1997). TRAIL receptors 1 (DR4) and 2 (DR5) signal FADD-dependent apoptosis and activate NF-kappaB. Immunity 7, 831-836.
93. Chaudhary, P. M., Eby, M., Jasmin, A., Bookwalter, A., Murray. J., and Hood, L. (1997). Death receptor 5, a new member of the TNFR family, and DR4 induce FADD-dependent apoptosis and activate the NF-kappaB pathway. Immunity 7, 821-830.
94. Lin, Y., Devin, A., Cook, A., Keane, M. M., Kelliher, M., Lipkowitz, S., and Liu, Z. G. (2000). The death domain kinase RIP is essential for TRAIL (Apo2L)-induced activation of IkappaB kinase and c-Jun N-terminal kinase. Mol Cell Biol 20, 6638-6645.
95. Meurette, 0., Rebillard, A., Huc, L., Le Moigne, G., Merino, D., Micheau, 0., Lagadic-Gossmann, D., and Dimanche-Boitrel, M. T. (2007). TRAIL induces receptor-interacting protein 1-dependent and caspase-dependent necrosis-like cell death under acidic extracellular conditions. Cancer Res 67, 218-226.
96. Nykjaer, A., Willnow, T. E., and Petersen, C. M. (2005). p75NTR—live or let die. Curr Opin Neurobiol 15, 49-57.
97. Liepinsh, E., Ilag, L. L., Otting, G., and Ibanez, C. F. (1997). NMR structure of the death domain of the p75 neurotrophin receptor. EMBO J. 16, 4999-5005.
98. Coulson, E. J., Reid, K., Barrett, G. L., and Bartlett, P. F. (1999). p75 neurotrophin receptor-mediated neuronal death is promoted by Bcl-2 and prevented by Bcl-xL. J Biol Chem 274, 16387-16391.
99. El Yazidi-Belkoura, I., Adriaenssens, E., Dolle, L., Descamps, S., and Hondermarck, H. (2003). Tumor necrosis factor receptor-associated death domain protein is involved in the neurotrophin receptor-mediated antiapoptotic activity of nerve growth factor in breast cancer cells. J Biol Chem 278, 16952-16956.
100. Llovet J. M., Burroughs A. & Bruix J. (2003) Hepatocellular carcinoma. Lancet 362, 1907-1917.
101. Maeda S., Kamata H., Luo J-L., Leffert H. & Karin M. (2005). IKKl3 couples hepatocyte death to cytokine-driven compensatory proliferation that promotes chemical hepatocarcinogenesis. Cell 121, 977-990.
102. Pikarsky E, Porat R M, Stein I, Abramovitch R, Amit S, Kasem S, Gutkovich-Pyest F, Urieli-Shoval S, Galun E, Ben-Neriah Y. (2004) NF-KB functions as a tumor promoter in inflammation-associated cancer. Nature 431, 461-466.
103. Mauad T H, Carin M. J. van Nieuwkerk, Koert P. Dingemans, Jaap J. M. Smit, Alfred H. Schinkel, Robbert G. E. Notenboom, Marius A. van den Bergh Weerman, Ronald P. Verkruisen, Albert K. Groen, Ronald P. J. Oude Elferink, Martin A. van der Valk, Piet Borst, and G. Johan A. Offerhaus (1994) Mice with homozygous disruption of the mdr2 P-glycoprotein gene. A novel animal model for studies of nonsuppurative inflammatory cholangitis and hepatocarcinogenesis. Am. J. Pathol. 145, 1237-1245.
104. Verna L., Whysner J, Williams GM. (1996) N-nitroso-diethylamine mechanistic data and risk assessment: bioactivation, DNA-adduct formation, mutagenicity, and tumor initiation. Pharmacol. Ther. 71, 57-81.
105. Mueller M. M. (2006) Inflammation in epithelial skin tumors: old stories and new ideas. Eur. J. Can. 42, 735-744.
106. Moore R. J., Owens D M, Stamp G, Arnott C, Burke F, East N, Holdsworth H, Turner L, Rollins B, Pasparakis M, Kollias G, Balkwill F (1999) Mice deficient in tumor necrosis factor-a are resistant to skin carcinogenesis. Nat. Med. 5, 828-831.
107. Swann J. B., Vesely M D, Silva A, Sharkey J, Akira S, Schreiber $R^D$, Smyth MJ. (2008) Demonstration of inflammation-induced cancer and cancer immunoediting during primary tumorigenesis. PNAS 105, 652-656.
108. Voortman J. et al. TRAIL therapy in non-small cell lung cancer cells: sensitization to death receptor-mediated apoptosis by proteasome inhibitor bortezomib Mol Cancer Ther Jul. 1, 2007 6, 2103.
109. Carlo-Stella et al. Targeting TRAIL agonistic receptors for cancer therapy. Clin Cancer Res. 2007 Apr. 15;13(8): 2313-7.

What is claimed is:

1. A method of diagnosing and treating a brain glioblastoma, astrocytoma, or a pancreatic tumor in a subject, the method comprising
   detecting the level of expression of an anti-TNF Induced Apoptosis (ATIA) polypeptide in a brain or pancreas tissue sample from the subject by contacting the brain or pancreas tissue sample with an ATIA antibody and detecting binding between ATIA polypeptide and the ATIA antibody,
   comparing the level of expression of the ATIA polypeptide in the brain or pancreas tissue sample from the subject to a level of expression of ATIA polypeptide in normal brain or pancreas tissue, respectively, wherein the ATIA polypeptide comprises SEQ ID NO: 9 or SEQ ID NO: 10,
   detecting an increase level of expression of ATIA polypeptide in the sample relative to the level of expression of ATIA polypeptide in a tissue-matched normal control reference, wherein an increased level of ATIA polypeptide indicates that the subject has a brain glioblastoma, astrocytoma, or a pancreatic tumor, and
   diagnosing the subject with a brain glioblastoma, astrocytoma, or a pancreatic tumor, and
   reducing the level of expression of ATIA polypeptide in the diagnosed subject, and
   administering an effective treatment to the subject after the level of expression of the ATIA polypeptide is reduced.

2. The method of claim 1, wherein the ATIA polypeptide consists of a sequence selected from the group consisting of: SEQ ID NO: 2, SEQ ID NO: 6, SEQ ID NO: 9 and SEQ ID NO: 10.

3. The method of claim 1, wherein the level of expression is determined in an immunological assay, enzyme-linked immunosorbent assay (ELISA), or immunohistochemical assay.

4. The method of claim 3, wherein the ELISA is used to detect the extracellular portion of ATIA.

5. The method of claim 4, wherein the extracellular portion comprises a sequence selected from the group consisting of: SEQ ID NO: 9 and SEQ ID NO: 10.

6. A method of diagnosing and treating a brain glioblastoma, astrocytoma, or a pancreatic tumor in a subject, the method comprising
   detecting the level of expression of an anti-TNF Induced Apoptosis (ATIA) polypeptide in a brain or pancreas tissue sample from the subject,
   comparing the level of expression of the ATIA polypeptide in the brain or pancreas tissue sample from the subject to a level of expression of ATIA polypeptide in normal brain or pancreas tissue, respectively, wherein the ATIA polypeptide comprises SEQ ID NO: 9 or SEQ ID NO: 10,
   detecting an increase level of expression of ATIA polypeptide in the sample relative to the level of expression of ATIA polypeptide in a tissue-matched normal control reference, wherein an increase level of ATIA polypeptide indicates that the subject has a brain glioblastoma, astrocytoma, or a pancreatic tumor,
   diagnosing the subject with a brain glioblastoma, astrocytoma, or a pancreatic tumor,
   reducing the level of expression of ATIA poltpeptide in the diagnosed subject, and
   administering an effective treatment to the subject after the level of expression of the ATIA polypeptide is reduced.

7. A method of diagnosing a brain glioblastoma, astrocytoma, or a pancreatic tumor in a subject, the method comprising
   detecting the level of expression of an ATIA polypeptide in a biological fluid sample from the subject by contacting the biological fluid sample with an ATIA antibody and detecting binding between ATIA and the ATIA antibody,
   comparing the level of expression of the ATIA polypeptide in the biological fluid sample from the subject to a level of expression of ATIA polypeptide in a matched normal control biological fluid sample, wherein the ATIA polypeptide comprises SEQ ID NO: 9 or SEQ ID NO: 10,
   detecting an increased level of expression of ATIA polypeptide in the biological fluid. sample from the subject relative to the level of expression of ATIA polypeptide in the biological fluid matched normal control reference, wherein an increased level of ATIA polypeptide indicates that the subject has a brain glioblastoma, astrocytoma, or a pancreatic tumor,
   diagnosing the subject with the a brain glioblastoma, astrocytoma, or a pancreatic tumor, and
   reducing the level of expression of ATIA polypeptide in the diagnosed subject to render the tumor more sensitive to a chemotherapeutic agent,
   wherein the biological fluid is blood, blood plasma, serum, or cerebrospinal fluid.

8. The method of claim 7, wherein said ATIA polypeptide is a soluble ATIA polypeptide.

9. The method of claim 7, wherein the biological fluid sample is serum.

10. The method of claim 7, wherein the method further comprises administering an effective treatment after the level of expression of the ATIA polypeptide is reduced.

11. A method of diagnosing a brain glioblastoma, astrocytoma, or a pancreatic tumor in a subject, the method comprising:
   detecting the level of expression of an anti-TNF Induced Apoptosis (ATIA) polypeptide in a blood sample by contacting said blood sample with an ATIA antibody and detecting binding between ATIA polypeptide and the ATIA antibody,
   comparing the level of expression of the ATIA polypeptide in the blood sample from the subject to a level of expression of ATIA polypeptide in a blood sample from a healthy subject, respectively, wherein the ATIA polypeptide comprises SEQ ID NO: 9 or SEQ ID NO: 10,
   detecting an increase level of expression of ATIA polypeptide in the blood sample from the subject relative to the level of expression of ATIA polypeptide in a blood sample from a healthy subject, wherein an increase level of ATIA polypeptide indicates that the subject has a brain glioblastoma, astrocytoma, or a pancreatic tumor,
   diagnosing the subject with a brain glioblastoma, astrocytoma, or a pancreatic tumor, and
   reducing the level of expression of ATIA polypeptide in the diagnosed subject, thereby making the tumor more sensitive to chemotherapeutic agents.

12. The method of claim 11, wherein the method further comprises administering an effective treatment after the level of expression of the ATIA polypeptide is reduced.

* * * * *